US008568690B2

(12) United States Patent
Lu et al.

(10) Patent No.: US 8,568,690 B2
(45) **Date of Patent: *Oct. 29, 2013**

(54) MRI CONTRAST AGENTS AND HIGH-THROUGHPUT SCREENING BY MRI

(75) Inventors: Yi Lu, Champaign, IL (US); Mehmet Veysel Yigit, Malden, MA (US); Debapriya Mazumdar, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1322 days.

This patent is subject to a terminal disclaimer.

(21) Appl. No.: 12/182,018

(22) Filed: Jul. 29, 2008

(65) Prior Publication Data

US 2009/0098550 A1 Apr. 16, 2009

Related U.S. Application Data

(60) Provisional application No. 60/953,193, filed on Jul. 31, 2007, provisional application No. 61/020,659, filed on Jan. 11, 2008.

(51) Int. Cl.
*A61B 5/055* (2006.01)
*A61K 49/00* (2006.01)

(52) U.S. Cl.
USPC .......................................... 424/9.1; 424/9.32

(58) Field of Classification Search
USPC ........................................................ 424/9.32
See application file for complete search history.

(56) References Cited

U.S. PATENT DOCUMENTS

| | | | | |
|---|---|---|---|---|
| 4,362,603 | A | 12/1982 | Presson et al. | |
| 4,703,017 | A | 10/1987 | Campbell et al. | |
| 4,746,631 | A | 5/1988 | Clagett | |
| 4,855,240 | A | 8/1989 | Rosenstein et al. | |
| 4,857,319 | A | 8/1989 | Crowe et al. | |
| 5,008,109 | A | 4/1991 | Tin | |
| 5,459,040 | A | 10/1995 | Hammock et al. | |
| 5,472,881 | A | 12/1995 | Beebe et al. | |
| 5,580,967 | A | 12/1996 | Joyce | |
| 5,593,835 | A | 1/1997 | Rando et al. | |
| 5,631,148 | A | 5/1997 | Urdea | |
| 5,663,064 | A | 9/1997 | Burke et al. | |
| 5,807,718 | A | 9/1998 | Joyce et al. | |
| 5,807,967 | A | 9/1998 | Snow et al. | |
| 5,910,408 | A | 6/1999 | Szostak et al. | |
| 5,989,813 | A | 11/1999 | Gerdes | |
| 6,040,138 | A | 3/2000 | Lockhart et al. | |
| 6,110,462 | A | 8/2000 | Barbas et al. | |
| 6,159,347 | A | 12/2000 | Sumner, Jr. et al. | |
| 6,287,765 | B1 | 9/2001 | Cubicciotti | |
| 6,316,194 | B1 | 11/2001 | Karn et al. | |
| 6,326,508 | B1 | 12/2001 | Godbole et al. | |
| 6,361,944 | B1 | 3/2002 | Mirkin et al. | |
| 6,387,617 | B1 | 5/2002 | Asher et al. | |
| 6,426,335 | B1 | 7/2002 | Janjic et al. | |
| 6,451,535 | B1 | 9/2002 | Jenne et al. | |
| 6,485,982 | B1 | 11/2002 | Charlton | |
| 6,541,617 | B1 | 4/2003 | Bamdad et al. | |
| 6,630,306 | B1 | 10/2003 | Breaker | |
| 6,706,474 | B1 | 3/2004 | Lu et al. | |
| 6,818,455 | B2 | 11/2004 | May et al. | |
| 6,843,890 | B1 | 1/2005 | Godbole | |
| 6,849,414 | B2 | 2/2005 | Guan et al. | |
| 6,890,719 | B2 | 5/2005 | Lu et al. | |
| 7,109,165 | B2 | 9/2006 | Matulic-Adamic et al. | |
| 7,192,708 | B2 | 3/2007 | Lu et al. | |
| 7,332,283 | B2 | 2/2008 | Lu et al. | |
| 7,459,145 | B2 * | 12/2008 | Bao et al. | 424/9.32 |
| 7,485,419 | B2 | 2/2009 | Lu et al. | |
| 7,534,560 | B2 * | 5/2009 | Lu et al. | 435/6.12 |
| 7,612,185 | B2 | 11/2009 | Lu et al. | |
| 7,799,554 | B2 | 9/2010 | Mazumdar et al. | |
| 7,829,350 | B2 * | 11/2010 | Josephson et al. | 436/526 |
| 7,892,734 | B2 | 2/2011 | Lu et al. | |
| 7,902,353 | B2 | 3/2011 | Lu et al. | |
| 7,906,320 | B2 | 3/2011 | Lu et al. | |
| 2003/0149257 | A1 | 8/2003 | Sorge et al. | |
| 2003/0215810 | A1 | 11/2003 | Lu et al. | |
| 2003/0235611 | A1 | 12/2003 | Ehringer et al. | |
| 2004/0018515 | A1 | 1/2004 | Diener et al. | |
| 2004/0110167 | A1 | 6/2004 | Gerdes et al. | |
| 2004/0126882 | A1 | 7/2004 | Ellington et al. | |
| 2004/0158051 | A1 | 8/2004 | Ozkan et al. | |
| 2004/0175693 | A1 | 9/2004 | Lu et al. | |
| 2005/0037075 | A1 | 2/2005 | Farokhzad et al. | |
| 2005/0136500 | A1 | 6/2005 | Yang et al. | |
| 2005/0282186 | A1 | 12/2005 | Lu et al. | |
| 2006/0019406 | A1 | 1/2006 | Wei et al. | |
| 2006/0040408 | A1 | 2/2006 | Jones et al. | |
| 2006/0045910 | A1 | 3/2006 | Ehringer | |
| 2006/0094026 | A1 | 5/2006 | Lu et al. | |
| 2006/0166222 | A1 | 7/2006 | Lu et al. | |
| 2007/0037171 | A1 | 2/2007 | Lu et al. | |
| 2007/0269821 | A1 | 11/2007 | Mazumdar et al. | |
| 2008/0176228 | A1 | 7/2008 | Lu et al. | |
| 2009/0011402 | A1 | 1/2009 | Lu et al. | |
| 2009/0029874 | A1 | 1/2009 | Lu et al. | |
| 2009/0197261 | A1 | 8/2009 | Lu et al. | |
| 2010/0105039 | A1 | 4/2010 | Lu et al. | |

(Continued)

FOREIGN PATENT DOCUMENTS

| | | |
|---|---|---|
| EP | 121970 | 10/1984 |
| EP | 1219708 | 7/2002 |

(Continued)

OTHER PUBLICATIONS

Paborsky et al. (J. Biol. Chem. 1993, 268, 20808-20811).*

(Continued)

*Primary Examiner* — Michael G Hartley
*Assistant Examiner* — Melissa Perreira
(74) *Attorney, Agent, or Firm* — Klarquist Sparkman, LLP

(57) ABSTRACT

The present invention provides an MRI contrast agent, comprising: MRI contrast agent particles, and oligonucleotides, attached to the particles.

29 Claims, 17 Drawing Sheets

(56) References Cited

U.S. PATENT DOCUMENTS

| | | |
|---|---|---|
| 2010/0151579 A1 | 6/2010 | Wang et al. |
| 2010/0166842 A1 | 7/2010 | Lu et al. |
| 2011/0123982 A1 | 5/2011 | Lu et al. |
| 2011/0171635 A1 | 7/2011 | Lu et al. |

FOREIGN PATENT DOCUMENTS

| | | |
|---|---|---|
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2003/094838 | 11/2003 |
| WO | WO 2004/046687 | 6/2004 |
| WO | WO 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/020786 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Huizegna et al. (Biochem. 1995, 34, 656-665).*
Carlson (Biotech. Healthcare 2007, 31-36).*
Hamaguchi et al. (Analyt. Biochem. 2001, 294, 126-131).*
Lu et al. (Angew. Chem. Int. Ed. 2006, 45, 90-94).*
International Search Report dated Mar. 4, 2009 for PCT application No. PCT/US2008/070177.
International Search Report dated Apr. 17, 2009 for PCT application No. PCT/US2008/051185.
International Search Report dated Aug. 13, 2009 for PCT application No. PCT/US2008/072327.
Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).
Stadler, B. et al., "Micropatterning of DNA-tagged vesicles", Langmuir, vol. 20, No. 26, pp. 11348-11354, (2004).
Pfeiffer, I. et al., "Bivalent cholesterol-Based coupling of oligonucletides to lipid membrane assemblies", Journal of the American Chemical Society, vol. 126, No. 33, pp. 10224-10225, (2004).
Shin, J. et al., "Acid-triggered release via dePEGylation of DOPE liposomes containing acid-labile vinyl ether PEG-lipids", Journal of Controlled Release, vol. 91, issues 1-2, pp. 187-200, (2003).
Cram, D.J. et al., "Organic Chemistry", Mcgraw-Hill, pp. 560-569, (1959).
Rusconi, C.P. et al., "Antidote-mediated control of an anticoagulant aptamer in vivo", Nature Biotechnology Letters, vol. 22, No. 11, pp. 1423-1428, (2004).
Willis M.C. et al., "Liposome-anchored vascular endothelial growth factor aptamers", Bioconjugate Chem., vol. 9, No. 5, pp. 573-582, (1998).
Healy, J.M. et al., "Pharmacokinetics and biodistribution of novel aptamer compositions", Pharm. Research, vol. 21, No. 12, pp. 2234-2246, (2004).
Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).
Farokhzad, O.C. et al., "Nanopartide-aptamer bioconjugates: A new approach for targeting prostate cancer cells", Cancer Research, vol. 64, pp. 7668-7672, (2004).
American Cancer Society Statistics for 2006. http://www.cancer.org/docroot/stt/stt_0.asp 2006.
Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).
Park, J.W. et al., "Tumor targeting using anti-her2 immunoliposomes", Journal of Controlled Release, vol. 74, pp. 95-113, (2001).
Kallab, V. et al., "HER2/EGFR internalization: a novel biomarker for ErbB-targeted therapeutics", Breast Cancer Research Treat., vol. 88, pp. S126-S127, (2004).
Wilson, K.S. et al., "Differential gene expression patterns in HER2/neu-positive and -negative breast cancer cell lines and tissues", American Journal of Pathology, vol. 161, No. 4, pp. 1171-1185, (2002).
Weigelt, B. et al., "Breast cancer metastasis: Markers and models", Nature Reviews, Cancer, vol. 5, pp. 591-602, (2005).
Pegram, M.D. et al., "Rational combinations of trastuzumab with chemotherapeutic drugs used in the treatment of breast cancer", Journal of the National Cancer Institute, vol. 96, No. 10, pp. 739-749, (2004).
Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).
Cheng, C. et al., "Formulation of Functionalized PLGA-PEG Nanoparticles for in Vivo Targeted Drug Delivery", Biomaterials, vol. 28, issue 5, pp. 869-876, (2007).
Bass, B.L. et al., "Specific interaction between the self-splicing RNA of Tetrahymena and its guanosine substrate: implications for biological catalysis by RNA", Nature, vol. 308, pp. 820-826, (1984).
Ellington, A.D. et al., "Combinatorial methods: aptamers and aptazymes", Part of the SPIE Conference on Advanced Materials and Opitical Systems for Chemical and Biological Detection, SPIE, vol. 3858, pp. 126-134, (1999).
Robertson, M.P. et al., "Aptazymes as generalized signal transducers", Nucleic Acids Symp. Ser., vol. 41, pp. 1-3, (1999).
Pagratis, N. C. et al., "Potent 2'-amino-, and 2'-fluoro-2'-deoxyribonucleotide RNA inhibitors of keratinocyte growth factor", Nature Biotechnology, vol. 15, pp. 68-73, (1997).
Lupold, S.E. et al., "Identification and characterization of nuclease-stabilized RNA molecules that bind human prostate cancer cells via the prostate-specific membrane antigen", Cancer research, vol. 62, pp. 4029-4033, (2002).
Jenison, R.D. et al., "Oligonucleotide inhibitors of P-selectin-dependent neutrophil-platelet adhesion", Antisense Nucleic Acid Drug Dev., vol. 8, pp. 265-279, (1998).
Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).

(56) References Cited

OTHER PUBLICATIONS

O'Connell, D. et al., "Calcium-dependent oligonucleotide antagonists specific for L-selectin", Proceedings of the National Academy of Science, U.S.A., vol. 93, pp. 5883-5887, (1996).
Soukup, G.A. et al., "Design of allosteric hammerhead ribozymes activated by ligand-induced structure stabilization", Structure, vol. 7, pp. 783-791, (1999).
Straubinger, R.M. et al., "Preparation and characterization of taxane-containing liposomes", Methods in Enzymology, vol. 391, pp. 97-117, (2005).
Rivera, E. "Liposomal anthracyclines in metastatic breast cancer: Clinical update", The Oncologist, vol. 8, supplement 2, pp. 3-9, (2003).
Kornblith, P. et al., "Breast cancer—Response rates to chemotherapeutic agents studied in vitro", Anticancer Research, vol. 23, pp. 3405-3411, (2003).
Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).
Allen, T.M. et al., "Therapeutic opportunities for targeted liposomal drug delivery", Advanced Drug Delivery Reviews, vol. 21, pp. 117-133, (1996).
Hofheinz, R.D. et al., "Liposomal encapsulated anti-cancer drugs", Anti-Cancer Drugs, vol. 16, pp. 691-707, (2005).
Schluep, T. et al., "Preclinical efficacy of the camptothecin-polymer conjugate IT-101 in multiple cancer models", Clinical Cancer Research, vol. 12, No. 5, pp. 1606-1614, (2006).
Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).
Cheng, J. et al., "Antitumor Activity of beta-Cyclodextrin Polymer-Camptothecin Conjugates", Molecular Pharmaceutics, vol. 1, No. 3, pp. 183-193, (2004).
Cheng, J. et al., "Synthesis of linear, beta-cyclodextrin-based polymers and their camptothecin conjugates", Bioconjugate Chem., vol. 14, pp. 1007-1017, (2003).
Guo, X. et al., "Steric stabilization of fusogenic liposomes by a low-pH sensitive PEG-diortho ester-lipid conjugate", Bioconjugate Chem., vol. 12, pp. 291-300, (2001).
Gerasimov, O.V. et al., "Cytosolic drug delivery using pH- and light-sensitive liposomes", Advanced Drug Delivery Reviews., vol. 38, pp. 317-338, (1999).
Rovira-Bru, M. et al., "Size and structure of spontaneously forming liposomes in lipid/PEG-lipid mixtures", Biophysical Journal, vol. 83, pp. 2419-2439, (2002).
Liu, J. et al., "Proofreading and error removal in a nanomaterial assembly", Angewandte Chemie, International Edition, vol. 44, pp. 7290-7293, (2005).
Liu, J. et al., "Design of asymmetric DNAzymes for dynamic control of nanoparticle aggregation states in response to chemical stimuli", Organic & Biomolecular Chemistry, vol. 4, pp. 3435-3441, (2006).
Cho, H.S. et al., "Structure of the extracellular region of HER2 alone and in complex with the Herceptin Fab", Nature, vol. 421, pp. 756-760, (2003).
Leahy, D.J. et al., "A Mammalian Expression Vector for Expression and Purification of Secreted Proteins for Structural Studies", Protein Expression and Purification, vol. 20, pp. 500-506, (2000).
Bartel, D.P. et al., "Isolation of new ribozymes from a large pool of random sequences", Science, vol. 261, pp. 1411-1418, (1993).
Jellinek, D. et al., "Inhibition of receptor binding by high-affinity RNA ligands to vascular endothelial growth factor", Biochemistry, vol. 33, pp. 10450-10456, (1994).
Jellinek, D. et al., "Potent 2'-Amino-2'-deoxypyrimidine RNA Inhibitors of Basic Fibroblast Growth Factor", Biochemistry, vol. 34, pp. 11363-11372, (1995).
Green, L.S. et al., "Inhibitory DNA Ligands to Platelet-Derived Growth Factor B-Chain", Biochemistry, vol. 35, pp. 14413-14424, (1996).
Lee, T.C. et al., "Overexpression of RRE-derived sequences inhibits HIV-1 replication in CEM cells", New Biologist, vol. 4, p. 66, (1992).
Andresen, T.L. et al., "Advanced strategies in liposomal cancer therapy: Problems and prospects of active and tumor specific drug release", Progress in Lipid Research, vol. 44, pp. 68-97, (2005).
Woodle, M.C. et al., "Sterically Stabilized Liposomes—Reduction in electrophoretic mobility but not electrostatic surface potential", Biophysical Journal, vol. 61, pp. 902-910, (1992).
Zalipsky, S. et al., "Long Circulating, Cationic Liposomes Containing Amino-Peg-Phosphatidylethanolamine", FEBS Letters, vol. 353, pp. 71-74, (1994).
Morrison, W., "A fast, simple and reliable method for the microdetermination of phosphorus in biological materials", Analytical Biochemistry, vol. 7, issue 2, pp. 218-224, (1964).
Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).
Klibanov, A.L. et al., "Activity of Amphipathic Poly(Ethylene Glycol)-5000 to Prolong the Circulation Time of Liposomes Depends on the Liposome Size and Is Unfavorable for Immunoliposome Binding to Target", Biochim. Biophys. Acta, vol. 1062, pp. 142-148, (1991).
Park, J.W. et al., "Development of Anti-P185$^{HER2}$ Immunoliposomes for Cancer-Therapy", Proceedings of the National Academy of Science U.S.A., vol. 92, pp. 1327-1331, (1995).
Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).
Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).
Gillies, E.R. et al., "A new approach towards acid sensitive copolymer micelles for drug delivery", Chemical Communications, Issue 14, pp. 1640-1641, (2003).
Joensuu, O.I., "Fossil Fuels as a Source of Mercury Pollution", Science, vol. 172, No. 3987, pp. 1027-1028, (1971).
Malm, O., "Gold mining as a source of mercury exposure in the Brazilian Amazon", Environmental Research, vol. 77, No. 2, pp. 73-78, (1998).
Tchounwou, P.B. et al., "Environmental exposure to mercury and its toxicopathologic implications for public health", Environmental Toxicology, vol. 18, No. 3,pp. 149-175, (2003).
Yoon, S. et al., "A bright and specific fluorescent sensor for mercury in water, cells, and tissue", Angewandte Chemie International Edition, vol. 46, No. 35, pp. 6658-6661, (2007).
Liu, X.F. et al., "Optical detection of mercury(II) in aqueous solutions by using conjugated polymers and label-free oligonucleotides", Advanced Materials, vol. 19, No. 11, p. 1471, (2007).
Chiang, C.K. et al., "Oligonucleotide-based fluorescence probe for sensitive and selective detection of mercury (II) in aqueous solution", Analytical Chemistry, vol. 80, No. 10, pp. 3716-3721, (2008).
Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).
Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).
Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).
Liu, C.W. et al., "Detection of mercury(II) based on Hg2+-DNA complexes inducing the aggregation of gold nanoparticles", Chemical Communications, vol. 19, pp. 2242-2244, (2008).
Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).
Wang, L. et al., "Gold nanoparticle-based optical probes for target-responsive DNA structures", Gold Bulletin, vol. 41, No. 1, pp. 37-41, (2008).

(56) References Cited

OTHER PUBLICATIONS

Clarkson, T.W. et al., "Mercury—Major Issues in Environmental-Health", Environmental Health Perspectives, vol. 100, pp. 31-38, (1993).
Wren, C.D. "A Review of Metal Accumulation and Toxicity in Wild Mammals, 1 Mercury", Environmental Research, vol. 40, No. 1, pp. 210-244, (1986).
Koos, B.J. et al., "Mercury Toxicity in Pregnant Woman, Fetus, and Newborn-Infant-Review", American Journal of Obstetrics and Gynecology, vol. 126, No. 3, pp. 390-409, (1976).
Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).
Braman, R.S., "Membrane Probe—Spectral Emission Type Detection System for Mercury in Water", Analytical Chemistry, vol. 43, No. 11, pp. 1462-1467, (1971).
Wernette, D.P. et al., "Surface immobilization of catalytic beacons based on ratiometric fluorescent DNAzyme sensors: a systematic study", Langmuir, vol. 23, No. 18, pp. 9513-9521, (2007).
Wang, Z. et al., "Highly sensitive "turn-on" fluorescent sensor for Hg2+ in aqueous solution based on structure-switching DNA", Chemical Communications, pp. 6005-6007, (2008).
Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).
Turner, A. P. F., "Biochemistry: Biosensors—Sense and Sensitivity", Science, vol. 290, No. 5495, pp. 1315-1317, (2000).
Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).
Arnez, J. G. et al., "Crystal structure of unmodified $tRNA^{Gin}$ complexed with glutaminyl-tRNA synthetase and ATP suggests a possible role for pseudo-uridines in stabilization of RNA structure", Biochemistry, vol. 33, pp. 7560-7567, (1994).
Blake, R. C., II, et al., "Novel monoclonal antibodies with specificity for chelated uranium (VI): isolation and binding properties", Bioconjug. Chem. , vol. 15, pp. 1125-1136, (2004).
Boomer, D. W., et al, "Determination of uranium in environmental samples using inductively coupled plasma mass spectrometry", Anal. Chem., vol. 59, pp. 2810-2813, (1987).
Breaker, R. R., "Natural and engineered nucleic acids as tools to explore biology", Nature, vol. 432, pp. 838-845, (2004).
Brina, R. et al., "Direct detection of trace levels of uranium by laser-induced kinetic phosphorimetry", Anal. Chem., vol. 64, pp. 1413-1418, (1992).
Chung N. et al., "Selective extraction of gold(III) in the presences of Pd(II) and Pt(IV) by saltin-out of the mixture of 2-propanal and water", Talanta, vol. 58, pp. 927-933, (2002).
Craft, E. et al., "Depleted and natural uranium: chemistry and toxicological effects", J. Toxicol. Environ. Health, Part B, vol. 7, pp. 297-317, (2004).
Demers, L. M. et al., "Thermal desorption behavior and binding properties of DNA bases and nucleosides on gold", J. Am. Chem. Soc. vol. 124, pp. 11248-11249, (2002).
Frankforter G. et al., "Equilibria in the systems of the higher alcohols, water and salts", J. Am. Chem. Soc., vol. 37, pp. 2697-2716 (1915).
Frankforter G., et al., "Equilibria in the systems, water, acetone and inorganic salts", J. Am. Chem. Soc., vol. 36, pp. 1103-1134, (1914).
Frankforter G., et al., "Equilibria in systems containing alcohols, salts and water, including a new method of alcohol analysis", J. Phys. Chem., vol. 17, pp. 402-473, (1913).
Ginnings, P. et al., "Ternary systems: water, tertiary butanol and salts at 30 ° C", J. Am. Chem. Soc., vol. 52, pp. 2282-2286, (1930).
Gongalsky, K., "Impact of pollution caused by uranium production on soil macrofauna", Environ. Monit. Assess., vol. 89, pp. 197-219, (2003).
Homola, J. et al., "Surface Plasmon Resonance (SPR) Sensors", Springer Series on Chemical Sensors and Biosensors, vol. 4, pp. 45-67, (2006).
US EPA, "Drinking water contaminants", found at http://www.epa.gov/safewater/contaminants/index.html, pp. 1-17, printed on Nov. 23, 2009.
Jones, L. A., et al., "Extraction of phenol and its metabolites from aqueous solution", J. Agric. Food Chem., vol. 41, pp. 735-741, (1993).
Katz, E. et al., "Integrated nanoparticle-biomolecule hybrid systems: sythesis, properties, and applications"Angew. Chem. Int. Ed., vol. 43, pp. 6042-6108, (2004).
Kobe, K. A. et al., "The ternary systems ethylene glycol-potassium carbonate-water and dioxane-potassium carbonate-water", J. Phys. Chem., vol. 446, pp. 629-633, (1940).
Laromaine, A. et al., "Protease-triggered dispersion of nanoparticle assemblies", J. Am. Chem. Soc., vol. 129, pp. 4156-4157, (2007).
Lazarova, Z. et al., "Solvent extraction of lactic acid from aqueous solution", Journal of Biotechnology, vol. 32, pp. 75-82, (1994).
Lee, J. H. et al., "Site-specific control of distances between gold nanoparticles using phosphorothioate anchors on DNA and short bifunctional molecular fastener", Angew. Chem. Int. Ed., vol. 46, pp. 9006-9010, (2007).
Leggett, D. C. et al., "Salting-out solvent extraction for preconcentration of neutral polar organic solutes from water", Anal. Chem., vol. 62, pp. 1355-1356, (1990).
Leinonen, H., "Stress corrosion cracking and life prediction evaluation of austenitic stainless steels in calcium choloride solution", Corrosion Science, vol. 52, No. 5, pp. 337-346 (1996).
Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).
Li, H. et al., "Detection of specific sequences in rna using differential adsorption of single-stranded oligonucletiode on gold nanoparticles", Anal. Chem., vol. 77, No. 19, pp. 6229-6233, (2005).
Li, H. et al., "Colorimetric detection of dna sequences based on electrostatic interactions with unmodified gold nanoparticles", Proc. Natl. Acad. Sci. U.S.A. vol. 101, pp. 14036-14039, (2004).
Li, H. et al., "Label-free colorimetric detection of specific sequences in genomic dna amplified by the polymerase chain reaction", J. Am. Chem. Soc., vol. 126, pp. 10958-10961, (2004).
Likidis, Z. et al., "Recovery of penicillin G from fermentation broth with reactive extraction in a mixer-settler" , Biotechnology Letters, vol. 9, No. 4, pp. 229-232, (1987).
Lim, I. et al., "Homocysteine-mediated reactivity and assembly of gold nanoparticles", Langmuir, vol. 23, pp. 826-833, (2007).
Lu, Y. et al., "Functional DNA nanotechnology:emerging applications of DNAzymes and aptamers", Curr. Opion. Biotech., vol. 17, pp. 580-588, (2006).
Long, F. A., et al., "Activity coefficients of nonelectrolyte solutes in aqueous salt solutions", Chem. Rev., vol. 51, pp. 119-169, (1952).
Lu, X. et al., "Salting-out separation and liquid-liquid equilibrium of tertiary butanol aqueous solution", Chemical Engineering Journal, vol. 78, pp. 165-171, (2000).
Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).
Mlakar, M. et al., "Stripping voltammetric determination of trace levels of uranium by synergic adsorptions", Analytica Chimica Acta, vol. 221, pp. 279-287, (1989).
Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).
Pierotti, R. A., "A scaled particle theory of aqueous and nonaqueous solutions", Chemical Reviews, vol. 76, No. 6, pp. 717-726, (1976).

(56) References Cited

OTHER PUBLICATIONS

Centers for Disease Control, "Preventing lead poisoning in young children", U.S. Department of Health and Human Services, Public Health Service, Centers for Disease Control: Atlanta, GA, (1991).
Public Law 102-550; Residential Lead-Based Paint Hazard Reduction Act of the housing and Community Development Act of 1992; 28 pages, (1992).
Qiang, Z. et al., "Potentiometric determination of acid dissociation constants ($pK_a$) for human and veterinary antibiotics", Water Research, vol. 38, pp. 2874-2890, (2004).
Rohwer, H. et al., "Interactions of uranium and thorium with arsenazo III in an aqueous medium", Analytica Chimica Acta, vol. 341, pp. 263-268, (1997).
Safavi, A. et al., "A novel optical sensor for uranium determination", Analytica Chimica Acta vol. 530, pp. 55-60, (2005).
Sato, K. et al., "Rapid aggregation of gold nanoparticles induced by non-cross-linking DNA hybridization", J. Am. Chem. Soc., vol. 125, pp. 8102-8103, (2003).
Schenk, F. J. et. al., "Comparison of magnesium sulfate and sodium sulfate for removal of water from pesticide extracts of foods", J. AOAC International, vol. 85, No. 5, pp. 1177-1180, (2002).
Sessler, J. L. et al., "Hexaphyrin (1.0.1.0.0.0). a new colorimetric actinide sensor", Tetrahedron, vol. 60, pp. 11089-11097, (2004).
Shafer-Peltier, K. E. et al., "Toward a glucose biosensor based on surface-enhanced raman scattering", J. Am. Chem. Soc., vol. 125, pp. 588-593, (2003).
Sharma, J. et al., "DNA-templated self-assembly of two-dimensional and periodical gold nanoparticle arrays", Angew. Chem. Int. Ed., vol. 45, pp. 730-735, (2006).
Si, S. Et al., "pH-controlled reversible assembly of peptide-functionalized gold nanoparticles", Langmuir, vol. 23, pp. 190-195, (2007).
Simard, J. et al., "Formation and pH-controlled assembly of amphiphilic gold nanoparticles", Chemical Commun., pp. 1943-1944, (2000).
Singleton, V. L., "An extraction technique for recovery of flavors, pigments, and other constituents from wines and other aqueous solutions", Am. J. Enol. Vitic., vol. 12, pp. 1-8, (1961).
Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).
Rao, D.S. et al., "Extraction of acetonitrile from aqueous solutions. 2. ternary liquid equilibria", Journal of Chemical and Engineering Data, vol. 24, No. 3, pp. 241-244, (1979).
Tabata, M. et al., "Ion-pair extraction of metalloporphyrins into acetonitrile for determination of copper(II)", Analytical Chemistry, vol. 68, No. 5, pp. 758-762, (1996).
Tabata, M. et al., "Chemical properties of water-miscible solvents separated by salting-out and their application to solvent extraction", Analytical sciences, vol. 10, pp. 383-388, (1994).
Van der Wal, Sj., "Low viscosity organic modifiers in reversed-phase HPLC", Chromatographia, vol. 20, No. 5, pp. 274-278, (1985).
Wang, J. et al., "A gold nanoparticle-based aptamer target binding readout for ATP assay", Adv. Mater., vol. 19, pp. 3943-3946, (2007).
Wang, L. et al., "Unmodified gold nanoparticles as a colorimetric probe for potassium DNA aptamers", Chem. Comm., vol. 36, 3780-3782, (2006).
Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).
Warren, K. W., Reduction of corrosion through improvements in desalting, Benelux Refinery Symposium. Lanaken, Belgium, 11 pages, (1995).
Wei, H. et al., "Simple and sensitive aptamer-based colorimetric sensing of protein using unmodified gold nanoparticle probes", Chem. Comm., vol. 36, pp. 3735-3737, (2007).
Wernette, D. P. et al., "Surface immobilization of catalytic beacons based on ratiometric fluorescent DNAzyme sensors: A systematic study", Langmuir, vol. 23, pp. 9513-9521, (2007).
Willner, I. et al., "Electronic aptamer-based sensors", Angew. Chem., Int. Ed., vol. 46, pp. 6408-6418, (2007).
Wu, Y. G., et al., "An extended Johnson-Furter equation to salting-out phase separation of aqueous solution of water-miscible organic solvents", Fluid Phase Equilibria, vol. 192, pp. 1-12, (2001).
Yan, H., "Nucleic acid nanotechnology", Science, vol. 306, pp. 2048-2049, (2004).
Yang, W. H. et al., "Discrete dipole approximation for calculating extinction and raman intensities for small particles with arbitrary shapes", J. Chem. Phys., vol. 103, pp. 869-875, (1995).
Deng, Z. et al., "DNA-Encoded self-assembly of gold nanoparticles into one-dimensional arrays", Angew. Chem. Int. Ed., vol. 44, pp. 3582-3585, (2005).
Zhao, W. et al., "Simple and rapid colorimetric biosensors based on DNA aptamer and noncrosslinking gold naoparticle aggregation", ChemBioChem, vol. 8, pp. 727-731, (2007).
Zhao, W. et al., "Highly stabilized nucleotide-capped small gold nanoparticles with tunable size", Advanced Materials, vol. 19, pp. 1766-1771, (2007).
Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).
Zhao, W. et al., "DNA aptamer folding on gold nanoparticles: from colloid chemistry to bionsenors", J. Am. Chem. Soc., vol. 130, (11), pp. 3610-3618, (2008).
Zhou, P. et al., "Extraction of oxidized and reduced forms of uranium from contaminated soils: effects of carbonate concentration pH", Environmental Science Technology, vol. 39, No. 12, pp. 4435-4440, (2005).
Jacoby, M., "Sensitive, selective mercury sensor nanoparticle-based colorimetric method detects part-per-billion levels of mercury", Chemical & Engineering News, pp. 1-3, May 2, 2007.
Cruz, R.P.G. et al., supplemental to "Dinucleotide junction cleavage versatility of 8-17 deoxyribozyme", Chemistry & Biology, vol. 11, pp. 57-67, (pp. 1-8) (2004).
Saleh, O. A. et al., "Direct detection of antibody-antigen binding using an on-chip artificial pore", Proceedings of the National Academy of Science, vol. 100, No. 3, pp. 820-824, (2003).
Han, C. et al., "Highly selective and sensitive colorimetric probes for $Yb^{3+}$ ions based on supramolecular aggregates assembled from B-cyclodextrin-4,4'-dipyridine inclusion complex modified silver nanoparticles", Chem. Commun., pp. 3545-3547, (2009).
Abstract of Joyce, G., "Design and catalytic activity of enzyumic DNA molecules"., (1998).
Aggarwal, S.K., et al., "Determination of lead in urine and whole blood by stable isotope dilution gas chromatography-mass spectrometry"., Clinical Chemistry, vol. 40, No. 8, pp. 1494-1502, (1994).
Alivisatos, A.P., et al., "Organization of "nanocrystal molecules" using DNA"., Nature, vol. 382, pp. 609-611, (1996).
Allara, D. et al., "Spontaneously organized molecular assemblies. 1.Formation, dynamics and physical properties of n-alkanoic acids adsorbed from solution on an oxidized aluminum surface", Langmuir, vol. 1, No. 1, pp. 45-52, (1985).
Andreola, M-L., et al., "DNA aptamers selected against the HIV-1 RNase H display in vitro antiviral activity"., Biochemistry, vol. 40, No. 34, pp. 10087-10094, (2001).
Bain, C. D., et al., "Modeling organic surfaces with self-assembled monolayers"., Angew. Chem. Int. Ed. Engl., vol. 28, No. 4, pp. 506-512, (1989).
Bannon, D.I., et al., "Graphite furnace atomic absorption spectroscopic measurement of blood lead in matrix-matched standards"., Clinical Chemistry, vol. 40, No. 9, pp. 1730-1734, (1994).
Been, M.D., et al., "Self-cleaving ribozymes of hepatitis delta virus RNA"., Eur. J. Biochem., vol. 247, pp. 741-753, (1997).
Berens, C., et al., "A tetracycline-binding RNA aptamer"., Bioorganic & Medicinal Chemistry, vol. 9, pp. 2549-2556, (2001).
Biroccio, A., et al., "Selection of RNA aptamers that are specific and high-affinity ligands of the hepatitis C virus RNA-dependent RNA polymerase"., Journal of Virology, vol. 76, No. 8, pp. 3688-3696, (2002).
Blake, D.A., et al., "Antibody-based sensors for heavy metal ions"., Biosensors & Bioelectronics, vol. 16, pp. 799-809, (2001).

(56) References Cited

OTHER PUBLICATIONS

Blank, M., et al., "Systematic evolution of a DNA aptamer binding to rat brain tumor microvessels. Selective targeting of endothelial regulatory protein pigpen"., Journal of Biological Chemistry, vol. 276, No. 19, pp. 16464- 16468, (2001).
Bock, L.C., et al., "Selection of single-stranded DNA molecules that bind and inhibit human thrombin"., Nature, vol. 355, pp. 564-566, (1992).
Bogden, J.D., et al., "Soil contamination from lead in paint chips"., Bulletin of Environmental Contamination & Toxicology, vol. 14, No. 3, pp. 289-294, (1975).
Boiziau, C., et al., "DNA aptamers selected against the HIV-1 trans-activation-responsive RNA element form RNA-DNA kissing complexes"., Journal of Biological Chemistry, vol. 274, No. 18, pp. 12730-12737, (1999).
Bowins, R.J., et al., "Electrothermal isotope dilution inductively coupled plasma mass spectrometry method for the determination of sub-ng $ml^{-1}$ levels of lead in human plasma"., Journal of Analytical Atomic Spectrometry, vol. 9, pp. 1233-1236, (1994).
Breaker, R.R., "Catalytic DNA: in training and seeking employment"., Nature Biotechnology, vol. 17, pp. 422-423, (1999).
Breaker, R.R., "DNA aptamers and DNA enzymes" Current Opinion in Chemical Biology, vol. 1, pp. 26-31, (1997).
Breaker, R.R., "DNA enzymes"., Nature Biotechnology, vol. 15, pp. 427-431, (1997).
Breaker, R.R., "Molecular Biology: Making Catalytic DNAs"., Science, vol. 290, issue 5499, pp. 2095-2096, (2000).
Breaker, R.R., et al., "A DNA enzyme that cleaves RNA"., Chemistry & Biology, vol. 1, No. 4, pp. 223-229, (1994).
Breaker, R.R., et al., "A DNA enzyme with $Mg^{2+}$-dependent RNA phosphoesterase activity"., Chemistry & Biology, vol. 2, No. 10, pp. 655-660, (1995).
Breaker, R.R., et al., "Engineered allosteric ribozymes as biosensor components"., Current Opinion in Biotechnology, vol. 13, pp. 31-39, (2002).
Brody, E.N., et al., "Aptamers as therapeutic and diagnostic agents"., Reviews in Molecular Biotechnology, vol. 74, pp. 5-13, (2000).
Broude, N.E., "Stem-loop oligonucleotides: a robust tool for molecular biology and biotechnology", Trends in Biotechnology, vol. 20, No. 6, pp. 249-256, (2002).
Brown, A.K., et al., "A lead-dependent DNAzyme with a two-step mechanism"., Biochemistry, vol. 42, No. 23, pp. 7152-7161, (2003).
Bruesehoff, P.J., et al., "Improving metal ion specificity during in Vitro selection of catalytic DNA"., Combinatorial Chemistry & High Throughput Screening, vol. 5, pp. 327-335, (2002).
Bruno, J.G., et al., "In vitro selection of DNA aptamers to anthrax spores with electrochemiluminescence detection"., Biosensors & Bioelectronics, vol. 14, pp. 457-464, (1999).
Bruno, J.G., et al., "Use of magnetic beads in selection and detection of biotoxin aptamers by electrochemiluminescence and enzymatic methods"., BioTechniques, vol. 32, No. 1, pp. 178-180, pp. 182-183, (2002).
Brust, M., et al., "Novel gold-dithiol nano-networks with non-metallic electronic properties"., Advanced Materials, vol. 7, No. 9, pp. 795-797, (1995).
Burdette, S.C., et al., "Fluorescent Sensors for $Zn^{2+}$ Based on a Fluorescein Platform: Synthesis, Properties and Intracellular Distribution"., J. Am. Chem. Soc., vol. 123, No. 32, pp. 7831-7841, (2001).
Burgstaller, P., et al., "Isolation of RNA aptamers for biological cofactors by in vitro selection"., Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding"., Nucleic Acids Research, vol. 23, No. 23, pp. 4769-4776, (1995).
Burke, D.H., et al., "A Novel Acidophilic RNA Motif That Recognizes Coenzyme A"., Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX"., Nucleic Acids Research, vol. 25, No. 10, pp. 2020-2024, (1997).
Burke, D.H., et al., "RNA aptamers to the peptidyl transferase inhibitor chloramphenicol"., Chemistry & Biology, vol. 4, No. 11, pp. 833-843, (1997).
Burmeister, J., et al., "Cofactor-assisted self-cleavage in DNA libraries with a 3'- 5'-phosphoramidate bond"., Angew. Chem. Int. Ed. Engl., vol. 36, No. 12, pp. 1321-1324, (1997).
Burwell Jr., R.L., "Modified silica gels as adsorbents and catalysts"., Chemical Technology, 4, pp. 370-377, (1974).
Cadwell, R.C., et al., "Mutagenic PCR"., PCR Methods and Applications, vol. 3, pp. S136-S140, (1994).
Cadwell, R.C., et al., "Randomization of genes by PCR mutagenesis"., PCR Methods and Applications, vol. 2, pp, 28-33, (1992).
Cake, K.M., et al., "In vivo x-ray fluorescence of bone lead in the study of human lead metabolism: serum lead, whole blood lead, bone lead, and cumulative exposure"., Advances in X-Ray Analysis, vol. 38, pp. 601-606, (1995).
Camara Rica, C., et al., "Determination of trace concentrations of lead and nickel in human milk by electrothermal atomisation atomic absorption spectrophotometry and inductively coupled plasma emission spectroscopy"., The Science of the Total Environment, vol. 22, pp. 193-201, (1982).
Cao, Y.W., et al., "DNA-modified core-shell Ag/Au nanoparticles"., J. Am. Chem. Soc., vol. 123, No. 32, pp. 7961-7962, (2001).
Carmi, N., et al., "Cleaving DNA with DNA"., Proc. Natl. Acad. Sci. USA, vol. 95, pp. 2233-2237, (1998).
Carmi, N., et al., "In vitro selection of self-cleaving DNAs"., Chemistry & Biology, vol. 3, No. 12, pp. 1039-1046, (1996).
Cech, T.R., "Structure and mechanism of the large catalytic RNAs: group I and group II introns and ribonuclease P"., The RNA World, pp. 239-269, Cold Spring Harbor Laboratory Press, Cold Spring Harbor, New York, (1993).
Cech, T.R., et al., "Group I ribozymes: substrate recognition, catalytic strategies, and comparative mechanistic analysis"., Nucleic Acids and Molecular Biology, vol. 10, pp. 1-17, (1996).
Chaloin, L., et al., "Endogenous expression of a high-affinity pseudoknot RNA aptamer suppresses replication of HIV-1"., Nucleic Acids Research, vol. 30, No. 18, pp. 4001-4008, (2002).
Chapman, K.B., et al., "In vitro selection of catalytic RNAs"., Current Opinion in Structural Biology, vol. 4, pp. 618-622, (1994).
Chartrand, P., et al., "Effect of structural modifications on the activity of the leadzyme"., Biochemistry, vol. 36, No. 11, pp. 3145-3150, (1997).
Chen, J., et al., "Synthesis from DNA of a molecule with the connectivity of a cube"., Nature, vol. 350, pp. 631-633, (1991).
Chen, C-T., et al., "A highly selective fluorescent chemosensor for lead ions"., J. Am. Chem. Soc., vol. 124, pp. 6246-6247, (2002).
Chen, J-H., et al., "A specific quadrilateral synthesized from DNA branched junctions"., J. Am. Chem. Soc., vol. 111, No. 16, pp. 6402-6407, (1989).
Chen, L., et al., "Crystal structure of a four-stranded intercalated DNA: $d(C_4)$"., Biochemistry, vol. 33, No. 46, pp. 13540-13546, (1994).
Chinnapen, D.J.F., et al., "Hemin-stimulated docking of cytochrome c to a hemin—DNA aptamer complex"., Biochemistry, vol. 41, No. 16, pp. 5202-5212, (2002).
Ciesiolka, J., et al., "Selection of an RNA domain that binds $Zn^{2+}$"., RNA, vol. 1, pp. 538-550, (1995).
Ciesiolka, J., et al., "Small RNA-divalent domains"., RNA, vol. 2, pp. 785-793, (1996).
Conaty, J., et al., "Selected classes of minimised hammerhead ribozyme have very high cleavage rates at low $Mg^{2+}$ concentration"., Nucleic Acids Research, vol. 27, No. 11, pp. 2400-2407, (1999).
Conn, M.M., et al., "Porphyrin Metalation Catalyzed by a Small RNA Molecule"., J. Am. Chem. Soc, vol. 118, No. 29, pp. 7012-7013, (1996).
Connell, G.J., et al., "RNAs with dual specificity and dual RNAs with similar specificity"., Science, New Series, vol. 264, issue 5162, pp. 1137-1141, (1994).

(56) References Cited

OTHER PUBLICATIONS

Connell, G.J., et al., “Three small ribooligonucleotides with specific arginine sites”., Biochemistry, vol. 32, No. 21, pp. 5497-5502, (1993).
Cuenoud, B., et al., “A DNA metalloenzyme with DNA ligase activity”., Nature, vol. 375, pp. 611-614, (1995).
Czarnik, A.W., “Desperately seeking sensors”., Chemistry & Biology, vol. 2, No. 7, pp. 423-428, (1995).
Dai, X., et al., “Cleavage of an amide bond by a ribozyme”., Science, New Series, vol. 267, issue 5195, pp. 237-240, (1995).
Davis, J.H., et al., “Isolation of high-affinity GTP aptamers from partially structured RNA libraries”., Proc. Natl. Acad. Sci. USA, vol. 99, No. 18, pp. 11616-11621, (2002).
Davis, K.A., et al., “Staining of cell surface human CD4 with 2'-F-pyrimidine-containing RNA aptamers for flow cytometry”., Nucleic Acids Research, vol. 26, No. 17, pp. 3915-3924, (1998).
Definition of the word “ion” printed from Merriam-Webster online dictionary (www.m-w.com) on Jun. 30, 2004.
Definition of the word “particle” printed from Merriam-Webster online dictionary (www.m-w.com) on Jun. 29, 2004.
Deo, S., et al., A Selective, Ratiometric Fluorescent Sensor for $Pb^{2+}$ J. Am. Chem. Soc., vol. 122, No. 1, pp. 174-175, (2000).
Derose, V.J., “Two Decades of RNA Catalysis”., Chemistry & Biology, vol. 9, pp. 961-969, (2002).
Didenko, V.V., “DNA probes using fluorescence resonance energy transfer (FRET): Designs and applications”., BioTechniques, vol. 31, pp. 1106-1121, (2001). We have reference, but we are missing pp. 1119-1121.
Doudna, J.A., et al., “The Chemical Repertoire of Natural Ribozymes”., Nature, vol. 418, pp. 222-228, (2002).
Dubois, L.H., et al., “Synthesis, structure, and properties of model organic surfaces”., Annu. Rev. Phys. Chem., vol. 43, pp. 437-463, (1992).
Earnshaw, D.J., et al., “Modified oligoribonucleotides as site-specific probes of RNA structure and function”., Biopolymers (Nucleic Acid Sciences), vol. 48, pp. 39-55, (1998).
Ekland, E.H., et al., “RNA-catalysed RNA polymerization using nucleoside triphosphates”., Nature, vol. 382, pp. 373-376, (1996).
Ekland, E.H., et al., “Structurally complex and highly active RNA ligases derived from random RNA sequences”., Science, vol. 269, issue 5222, pp. 364-370, (1995).
Elghanian, R., et al., “Selective colorimetric detection of polynucleotides based on the distance-dependent optical properties of gold nanoparticles”., Science, vol. 277, pp. 1078-1081, (1997).
Ellington, A.D., et al., “Aptamers as potential nucleic acid pharmaceuticals”., Biotechnology Annual Review, vol. 1, pp. 185-214, (1995).
Ellington, A.D., et al., “In vitro selection of RNA molecules that bind specific ligands”., Nature, vol. 346, pp. 818-822, (1990).
Ellington, A.D., et al., “Selection in vitro of single-stranded DNA molecules that fold into specific ligand-binding structures”., Nature, vol. 355, pp. 850-852, (1992).
Famulok, M., “Molecular Recognition of Amino Acids by RNA-Aptamers: An L-Citrulline Binding RNA Motif and Its Evolution into an L-Arginine Binder”., J. Am. Chem. Soc., vol. 116, No. 5, pp. 1698-1706, (1994).
Famulok, M., “Oligonucleotide aptamers that recognize small molecules”, Current Opinion in Structural Biology, vol. 9, pp. 324-329, (1999).
Famulok, M., et al., “In Vitro Selection Analysis of Neomycin Binding RNAs with a Mutagenized Pool of Variants of the 16S rRNA Decoding Region”., Biochemistry, vol. 35, No. 14, pp. 4265-4270, (1996).
Famulok, M., et al., “Stereospecific recognition of tryptophan agarose by in vitro selected RNA”., J. Am. Chem. Soc., vol. 114, No. 10, pp. 3990-3991, (1992).
Faulhammer, D., et al., “Characterization and Divalent Metal-ion Dependence of in Vitro Selected Deoxyribozymes which Cleave DNA/RNA Chimeric Oligonucleotides”., J. Mol. Biol., vol. 269, pp. 188-202, (1997).
Faulhammer, D., et al., “The $Ca^{2+}$ ion as a cofactor for a novel RNA-cleaving deoxyribozyme”., Angew. Chem., Int. Ed. Engl., vol. 35, No. 23/24, pp. 2837-2841, (1996).
Feldman, B.J., et al., “Determination of lead in blood by square wave anodic stripping voltammetry at a carbon disk ultramicroelectrode”., Analytical Chemistry, vol. 66, No. 13, pp. 1983-1987, (1994).
Ferguson, A., et al., “A novel strategy for selection of allosteric ribozymes yields riboreporter™ sensors for caffeine and aspartame”., Nucleic Acids Research, vol. 32, No. 5, pp. 1756-1766, (2004).
Fodor, S.P.A., et al., “Light-directed, spatially addressable parallel chemical synthesis”., Science, New Series, vol. 251, issue 4995, pp. 767-773, (1991).
Frank, D.N., et al., “In vitro selection for altered divalent metal specificity in the RNase P RNA”., Proc. Natl. Acad. Sci. USA, vol. 94, pp. 14355-14360, (1997).
Frens, G., et al., “Controlled Nucleation for the regulation of the particle size in monodisperse gold suspensions”., Nature Physical Science, vol. 241, pp. 20-22, (1973).
Fukusaki, E-I., et al., “DNA aptamers that bind to chitin”., Bioorganic & Medicinal Chemistry letters, vol. 10, pp. 423-425, (2000).
Geiger, A., et al., “RNA aptamers that bind L-arginine with sub-micromolar dissociation constants and high enantioselectivity”., Nucleic Acids Research, vol. 24, No. 6, pp. 1029-1036, (1996).
Geyer, C.R., et al., “Evidence for the metal-cofactor independence of an RNA phosphodiester-cleaving DNA enzyme”., Chemistry & Biology, vol. 4, No. 8, pp. 579-593, (1997).
Geyer, C.R., et al., “Lanthanide Probes for a Phosphodiester-cleaving, Lead-dependent, DNAzyme”, J. Mol. Biol., vol. 275, pp. 483-489, (1998).
Giver, L., et al., “Selection and design of high-affinity RNA ligands for HIV-1 Rev”., Gene, vol. 137, pp. 19-24, (1993).
Giver, L., et al., “Selective optimization of the Rev-binding element of HIV-1”.,Nucleic Acids Research, vol. 21, No. 23, pp. 5509-5516, (1993).
Godwin, H.A., et al., “A Flourescent Zinc Probe Based on Metal-Induced Peptide Folding”., J. Am. Chem. Soc., vol. 118, pp. 6514-6515, (1996).
Grabar, K., et al., “Preparation and characterization of Au colloid Monolayers”., Analytical chemistry, vol. 67, No. 4, pp. 735-743, (1995).
Granadillo, V.A., et al., “The influence of the blood levels of lead, aluminum and vanadium upon the arterial hypertension”., Clinica Chimica Acta, vol. 233, pp. 47-59, (1995).
Grate, D., et al., “Laser-mediated, site-specific inactivation of RNA transcripts”., Proc. Natl. Acad. Sci. USA, vol. 96, pp. 6131-6136, (1999).
Guschin, D., et al., “Manual manufacturing of oligonucleotide, DNA, and protein microchips”., Analytical Biochemistry, vol. 250, pp. 203-211, (1997).
Haller, A.A., et al., “In vitro selection of a 7-methyl-guanosine binding RNA that inhibits translation of capped mRNA molecules”., Proc. Natl. Acad. Sci. USA, vol. 94, pp. 8521-8526, (1997).
Harada, K., et al., “Identification of two novel arginine binding DNAs”., The EMBO Journal, vol. 14, No. 23, pp. 5798-5811, (1995).
Hartig, J.S., et al., “Reporter ribozymes for real-time analysis of domain-specific interactions in biomolecules: HIV-1 reverse transcriptase and the primer-template complex”., Angew. Chem. Int. Ed., vol. 41, No. 22, pp. 4263-4266, (2002).
He, X-x., et al., “Bioconjugated nanoparticles for DNA protection from cleavage”., J. Am. Chem. Soc., vol. 125, No. 24, pp. 7168-7169, (2003).
Hennrich, G., et al., “Redox switchable fluorescent probe selective for either Hg(II) or Cd(II) and Zn(II)” J. Am. Chem. Soc., vol. 121, No. 21, pp. 5073-5074, (1999).
Hesselberth, J., et al., “In vitro selection of nucleic acids for diagnostic applications”., Reviews in Molecular Biotechnology, vol. 74, pp. 15-25, (2000).
Hesselberth, J.R., et al., “Simultaneous detection of diverse analytes with an aptazyme ligase array”, Analytical Biochemistry vol. 312, pp. 106-112, (2003).

(56) References Cited

OTHER PUBLICATIONS

Ho, H-A., et al., "Optical sensors based on hybrid aptamer/conjugated polymer complexes"., J. Am. Chem. Soc., vol. 126, No. 5, pp. 1384-1387, (2004).
Hock, B., "Antibodies for immunosensors, A review"., Analytica Chimica Acta, vol. 347, pp. 177-186, (1997).
Hofmann, H.P., et al., "$Ni^{2+}$-binding RNA motifs with an asymmetric purine-rich internal loop and a G-A base pair"., RNA, vol. 3, pp. 1289-1300, (1997).
Holeman, L.A., et al., "Isolation and characterization of fluorophore-binding RNA aptamers"., Folding & Design, vol. 3, pp. 423-431, (1998).
Hoogstraten, C.G., et al., "NMR solution structure of the lead-dependent ribozyme: Evidence for dynamics in RNA catalysis"., J. Mol. Biol., vol. 284, pp. 337-350, (1998).
Hoogstraten, C.G., et al., "Structural analysis of metal ion ligation to nucleotides and nucleic acids using pulsed EPR spectroscopy"., J. Am. Chem. Soc., vol. 124, No. 5, pp. 834-842, (2002).
Huizenga, D.E., et al., "A DNA aptamer that binds adenosine and ATP"., Biochemistry, vol. 34, No. 2, pp. 656-665, (1995).
Iler, R.K., "The Chemistry of Silica: Solubility, Polymerization, Colloid and Surface Properties, and Biochemistry, Chapter 6, The surface chemistry of silica"., pp. 622-729, A Wiley-Interscience Publication, New York, (1979).
Illangasekare, M., et al., "Small-molecule-substrate interactions with a self-aminoacylating ribozyme"., J. Mol. Biol., vol. 268, pp. 631-639, (1997).
Imperiali, B., et al., "Peptide platforms for metal ion sensing"., Proc. SPIE-The international society for optical engineering, vol. 3858, pp. 135-143, (1999).
International Search Report dated Jan. 15, 2003 for PCT application No. PCT/US01/20557.
International Search Report dated Aug. 1, 2003 for PCT application No. PCT/US03/08483.
Iqbal, S.S., et al., "A review of molecular recognition technologies for detection of biological threat agents"., Biosensors & Bioelectronics, vol. 15, pp. 549-578, (2000).
Abstract of: Iwasaki, K., Mizota, T., Kenkyu Hokoku—Kanagawa-ken Kogyo Shikensho 1991, 62, 57.
Jagner, D., et al., "Determination of lead in microliter amounts of whole blood by stripping potentiometry"., Electroanalysis, vol. 6, pp. 285-291, (1994).
Jayasena, S.D., "Aptamers: an emerging class of molecules that rival antibodies in diagnostics"., Clinical Chemistry, vol. 45, No. 9, pp. 1628-1650, (1999).
Jenison, R., et al., "Interference-based detection of nucleic acid targets on optically coated silicon", Nature Biotechnology, vol. 19, pp. 62-65, (2001).
Jenison, R.D., et al., "High-resolution molecular discrimination by RNA"., Science, vol. 263, pp. 1425-1429, (1994).
Jenne, A., et al., "Rapid Identification and Characterization of Hammerhead-Ribozyme Inhibitors Using Fluorescence-Based Technology"., Nature Biotechnology, vol. 19, pp. 56-61, (2001).
Jenne, A., et al., "Real-time Characterization of Ribozymes by Fluorescence Resonance Energy Transfer (FRET)"., Angewandte Chemie. International Edition, vol. 38, No. 9, pp. 1300-1303, (1999).
Jhaveri, S., et al., "In vitro selection of signaling aptamers"., Nature Biotechnology, vol. 18, pp. 1293-1297, (2000).
Jhaveri, S.D., et al., "Designed signaling aptamers that transduce molecular recognition to changes in fluorescence intensity"., J. Am. Chem. Soc., vol. 122, No. 11, pp. 2469-2473, (2000).
Jin, R., et al., "What controls the melting properties of DNA-linked gold nanoparticle assemblies?"., J. Am. Chem. Soc., vol. 125, No. 6, pp. 1643-1654, (2003).
Joos, B., et al., "Covalent attachment of hybridizable oligonucleotides to glass supports"., Analytical Biochemistry, vol. 247, pp. 96-101, (1997).
Josephson, L., et al., "Magnetic nanosensors for the detection of oligonucleotide sequences"., Angewandte Chemie. International Edition, vol. 40, No. 17, pp. 3204-3206, (2001).
Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).
Joyce, G.F., "In vitro evolution of nucleic acids"., Current Opinion in Structural Biology, vol. 4, pp. 331-336, (1994).
Katahira, M., et al., "Two metal-binding sites in a lead ribozyme bound to competitively by $Pb^{2+}$ and $Mg^{2+}$: Induced structural changes as revealed by NMR"., European Journal of Biochemistry, vol. 255, pp. 727-733, (1998).
Kato, T., et al., "In vitro selection of DNA aptamers which bind to cholic acid"., Biochimica et Biophysica Acta, vol. 1493, pp. 12-18, (2000).
Kawakami, J., et al., "In vitro selection of aptamers that act with $Zn^{2+}$"., Journal of Inorganic Biochemistry, vol. 82, pp. 197-206, (2000).
Khan, R., et al., "Interaction of retroviral nucleocapsid proteins with transfer $RNA^{Phe}$: a lead ribozyme and $^1H$ NMR study"., Nucleic Acids Research, vol. 24, No. 18, pp. 3568-3575, (1996).
Khosraviani, M., et al., "Detection of heavy metals by immunoassay: Optimization and validation of a rapid, portable assay for ionic cadmium"., Environ. Sci. Technol., vol. 32, No. 1, pp. 137-142, (1998).
Kiga, D., et al., "An RNA aptamer to the xanthine/guanine base with a distinctive mode of purine recognition"., Nucleic Acids Research, vol. 26, No. 7, pp. 1755-1760, (1998).
Kim, M.H., et al., "Activation and repression of the activity of a lead ribozyme by the combination of $Pb^{2+}$ and $Mg^{2+1}$"., J. Biochem., vol. 122, No. 5, pp. 1062-1067, (1997).
Kluβmann, S., et al., "Mirror-image RNA that binds D-adenosine"., Nature Biotechnology, vol. 14, pp. 1112-1115, (1996).
Kohama, T., et al., "Molecular Cloning and Functional Characterization of Murine Sphingosine Kinase", The Journal of Biological Chemistry, vol. 273, No. 37, pp. 23722-23728, (1998).
Koizumi, M., et al., "Allosteric selection of ribozymes that respond to the second messengers cGMP and cAMP"., Nature Structural Biology, vol. 6, No. 11, pp. 1062-1071, (1999).
Koizumi, M., et al., "Molecular Recognition of cAMP by an RNA Aptamer"., Biochemistry, vol. 39, No. 30, pp. 8983-8992, (2000).
Koizumi, M., et al., "Allosteric ribozymes sensitive to the second messengers cAMP and cGMP"., Nucleic Acids Symposium Series, No. 42, pp. 275-276, (1999).
Kruger, K., et al., "Self-splicing RNA: autoexcision and autocyclization of the ribosomal RNA intervening sequence of the Tetrahymena"., Cell, vol. 31, pp. 147-157, (1982).
Lato, S.M., et al., "In vitro selection of RNA lectins: Using combinatorial chemistry to interpret ribozyme evolution"., Chemistry & Biology, vol. 2, No. 5, pp. 291-303, (1995).
Lauhon, C.T., et al., "RNA aptamers that bind flavin and nicotinamide redox cofactors"., J. Am. Chem. Soc., vol. 117, No. 4, pp. 1246-1257, (1995).
Lebruska, L.L., "Selection and Characterization of an RNA Decoy for Transcription Factor NF-kB"., Biochemistry, vol. 38, No. 10, pp. 3168-3174, (1999).
Lee, M., et al., "A fiber-optic microarray biosensor using aptamers as receptors"., Analytical Biochemistry, vol. 282, pp. 142-146, (2000).
Lee, S-W., et al., "Ordering of quantum dots using genetically engineered viruses"., Science, vol. 296, pp. 892-895, (2002).
Legault, P., et al., "Order, dynamics and metal-binding in the lead-dependent ribozyme"., J. Mol. Biol., vol. 284, pp. 325-335, (1998).
Lehman, N., et al., "Evolution in vitro of an RNA enzyme with altered metal dependence"., Nature, vol. 361, pp. 182-185, (1993).
Lemieux, S., et al., "Modeling active RNA structures using the intersection of conformational space: application to the lead-activated ribozyme"., RNA, vol. 4, pp. 739-749, (1998).
Levy, M., et al., "ATP-Dependent Allosteric DNA Enzymes"., Chemistry & Biology, vol. 9, pp. 417-426, (2002).
Li, J., et al., "A highly sensitive and selective catalytic DNA biosensor for lead ions"., J. Am. Chem. Soc., vol. 122, No. 42, pp. 10466-10467, (2000).
Li, J., et al., "In vitro selection and characterization of a highly efficient Zn(II)-dependent Rna-cleaving deoxyribozyme"., Nucleic Acids Research, vol. 28, No. 2, pp. 481-488, (2000).

(56) References Cited

OTHER PUBLICATIONS

Li, J.J., et al., "Using molecular beacons as a sensitive fluorescence assay for enzymatic cleavage of single-stranded DNA"., Nucleic Acids Research, vol. 28, No. 11, e52, pp. i-vi, (2000).
Li, Y., et al., "A catalytic DNA for porphyrin metallation"., Nature Structural Biology, vol. 3, No. 9, pp. 743-747, (1996).
Li, Y., et al., "Capping DNA with DNA"., Biochemistry, vol. 19, No. 11, pp. 3106-3114, (2000).
Li, Y., et al., "Deoxyribozymes: new players in the ancient game of biocatalysis"., Current Opinion in Structural Biology, vol. 9, pp. 315-323, (1999).
Li, Y., et al., "Phosphorylating DNA with DNA"., Proc. Natl. Acad. Sci. USA, vol. 96, pp. 2746-2751, (1999).
Link, S., et al., "Alloy formation of gold-silver nanoparticles and the dependence of the plasmon absorption on their composition"., J. Phys. Chem. B, vol. 103, No. 18, pp. 3529-3533, (1999).
Liu, H-W., et al., "Determination of cadmium, mercury and lead in seawater by electrothermal vaporization isotope dilution inductively coupled plasma mass spectrometry"., Spectrochimica Acta Part B Atomic Spectroscopy 54, pp. 1367-1375, (1999).
Liu, J., et al., "A colorimetric lead biosensor using DNAzyme-directed assembly of gold nanoparticles", J. Am. Chem. Soc., vol. 125, No. 22, pp. 6642-6643, (2003).
Liu, J., et al., "Accelerated color change of gold nanoparticles assembled by DNAzymes for simple and fast colorimetric $Pb^{2+}$ detection"., J. Am. Chem. Soc., vol. 126, No. 39, pp. 12298-12305, (2004).
Liu, J., et al., "Adenosine-dependent assembly of aptazyme-functionalized gold nanoparticles and its application as a colorimetric biosensor"., Analytical Chemistry, vol. 76, No. 6, pp. 1627-1632, (2004).
Liu, J., et al., "Colorimetric biosensors based on DNAzyme-assembled gold nanoparticles"., Journal of Fluorescence, vol. 14, No. 4, pp. 343-354, (2004).
Liu, J., et al., "Highly dispersible molecular sieve carbon nanoparticles"., Chem. Mater., vol. 16, No. 22, pp. 4205-4207, (2004).
Liu, X., et al., "A fiber-optic evanescent wave DNA biosensor based on novel molecular beacons"., Analytical Chemistry, vol. 71, No. 22, pp. 5054-5059, (1999).
Liu, Z., et al., "Assemblage of signaling DNA enzymes with intriguing metal-ion specificities and pH dependences"., J. Am. Chem. Soc., vol. 125, No. 25, pp. 7539-7545, (2003).
Lohse, P.A., et al., "Ribozyme-catalysed amino-acid transfer reactions"., Nature, vol. 381, pp. 442-444, (1996).
Lorsch, J.R., et al., "In vitro evolution of new ribozymes with polynudeotide kinase activity"., Nature, vol. 371, pp. 31-36, (1994).
Lorsch, J.R., et al., "In vitro selection of RNA aptamers specific for cyanocobalamin"., Biochemistry, vol. 33, No. 4, pp. 973-982, (1994).
Lott, W.B., et al., "A two-metal ion mechanism operates in the hammerhead ribozyme-mediated cleavage of an RNA substrate"., Proc. Natl. Acad. Sci. USA, vol. 95, pp. 542-547, (1998).
Lu, Y., "New transition-metal-dependent DNAzymes as efficient endonucleases and as selective metal biosensors"., Chem. Eur. J., vol. 8, No. 20, pp. 4588-4596, (2002).
Lu, Y., et al., "New fluorescent and colorimetric DNAzyme biosensors for metal ions", Journal of Inorganic Biochemistry, vol. 96, issue 1, pp. 30, Abstract of the $11^{th}$ International Conference on Biological Inorganic Chemistry; (Jul. 15, 2003).
Majerfeld, I., et al., "An RNA pocket for an aliphatic hydrophobe"., Structural Biology, vol. 1, No. 5, pp. 287-292, (1994).
Majerfeld, I., et al., "Isoleucine:RNA sites with associated coding sequences"., RNA, vol. 4, pp. 471-478, (1998).
Mannironi, C., et al., "In vitro selection of dopamine RNA ligands"., Biochemistry, vol. 36, No. 32, pp. 9726-9734, (1997).
Maoz, R., et al., "Penetration-controlled reactions in organized monolayer assemblies. 1. Aqueous permanganate interaction with monolayer and multilayer films of long-chain surfactants"., Langmuir, vol. 3, No. 6, pp. 1034-1044, (1987).
Marcus, A.H., et al., "Estimating the contribution of lead based paint to soil lead, dust lead, and childhood blood lead"., American Society for Testing and Materials Spec. STP 1226, pp. 12-23, (1995).
Marsh, T.C., et al., "A new DNA nanostructure, the G-wire, imaged by scanning probe microscopy"., Nucleic Acids Research, vol. 23, No. 4, pp. 696-700, (1995).
Matteucci, M.D., et al., "Synthesis of Deoxyoligonudeotides on a polymer support"., J. Am. Chem. Soc., vol. 103, No. 11, pp. 3185-3191, (1981).
Mecklenburg, M., et al., "A strategy for the broad range detection of compounds with affinity for nucleic acids"., Analytica Chimica Acta, vol. 347, pp. 79-86, (1997).
Mei, S.H.J., et al., "An efficient RNA-cleaving DNA enzyme that synchronizes catalysis with fluorescence signaling"., J. Am. Chem. Soc., vol. 125, No. 2, pp. 412-420, (2003).
Meli, M., et al., "Adenine-aptamer complexes: A bipartite RNA site that binds the adenine nucleic base"., The Journal of Biological Chemistry, vol. 277, No. 3, pp. 2104-2111, (2002).
Mirkin, C.A., et al., "A DNA-based method for rationally assembling nanoparticles into macroscopic materials"., Nature, vol. 382, pp. 607-609, (1996).
Mirkin, S.M., et al., "H-DNA and related structures"., Annu. Rev. Biophys. Biomol. Struct., vol. 23, pp. 541-576, (1994).
Miyawaki, A., et al. "Fluorescent indicators for $Ca^{2+}$ based on green fluorescent proteins and calmodulin"., Nature, vol. 388, pp. 882-887, (1997).
Mucic, R.C., et al., "Synthesis and characterization of DNA with ferrocenyl groups attached to their 5'-termini: electrochemical characterization of a redox-active nucleotide monolayer"., Chem. Commun., pp. 555-557, (1996).
Mullah, B., et al., "Automated synthesis of double dye-labeled oligonucleotides using tetramethylrhodamine (TAMRA) solid supports"., Tetrahedron Letters, vol. 38, No. 33, pp. 5751-5754, (1997).
Nazarenko, I.A., et al., "A closed tube format for amplification and detection of DNA based on energy transfer"., Nucleic Acids Research, vol. 26, No. 12, pp. 2516-2521, (1997).
Nazarenko, I.A., et al., "Defining a Smaller RNA Substrate for Elongation Factor Tu"., Biochemistry, vol. 34, No. 8, pp. 2545-2552, (1995).
Niemeyer, C.M., "Nanoparticles, proteins, and nucleic acids: Biotechnology meets materials science"., Angew. Chem. Int. Edition, vol. 40, pp. 4128-4158, (2001).
Nieuwlandt, D., et al., "In Vitro Selection of RNA Ligands to Substance P"., Biochemistry, vol. 34, No. 16, pp. 5651-5659, (1995).
Nissen, P., et al., "The structural basis of ribosome activity in peptide bond synthesis"., Science, vol. 289, pp. 920-930, (2000).
Nolte, A., et al., "Mirror-design of L-oligonucleotide ligands binding to L-arginine"., Nature Biotechnology, vol. 14, pp. 1116-1119, (1996).
Nutiu, R., et al., "Structure-switching signaling aptamers"., J. Am. Chem. Soc., vol. 125, No. 16, pp. 4771-4778, (2003).
Nuzzo, R.G., et al., "Spontaneously organized molecular assemblies. 3. Preparation and properties of solution adsorbed monolayers of organic disulfides on gold surfaces"., J. Am. Chem. Soc., vol. 109, No. 8, pp. 2358-2368, (1987).
O'Donnell, M.J., et al., "High-Density, Covalent Attachment of DNA to Silicon Wafers for Analysis by MALDI-TOF Mass Spectrometry"., Analytical Chemistry, vol. 69, No. 13, pp. 2438-2443, (1997).
Oehme, I., et al., "Optical sensors for determination of heavy metal ions"., Mikrochim. Acta, vol. 126, pp. 177-192, (1997).
Ohmichi, T., et al., "Role of $Nd^{3+}$ and $Pb^{2+}$ on the RNA cleavage reaction by a small ribozyme"., Biochemistry, vol. 36, No. 12, pp. 3514-3521, (1997).
Ohmichi, T., et al., "Effect of substrate RNA sequence on the cleavage reaction by a short ribozyme"., Nucleic Acids Research, vol. 26, No. 24, pp. 5655-5661, (1998).
Okazawa, A., et al., "In vitro selection of hematoporphyrin binding DNA aptamers"., Bioorganic & Medicinal Chemistry, Letters 10, pp. 2653-2656, (2000).
Ota, N., et al., "Effects of helical structures formed by the binding arms of DNAzymes and their substrates on catalytic activity"., Nucleic Acids Research, vol. 26, No. 14, pp. 3385-3391, (1998).

(56) References Cited

OTHER PUBLICATIONS

Pan, T., et al., "A small metalloribozyme with a two-step mechanism"., Nature, vol. 358, pp. 560-563, (1992).
Pan, T., et al., "In vitro selection of RNAs that undergo autolytic cleavage with $Pb^{2+}$"., Biochemistry, vol. 31, No. 16, pp. 3887-3895, (1992).
Pan, T., et al., "Properties of an in vitro selected $Pb^{2+}$ cleavage motif"., Biochemistry, vol. 33, No. 32, pp. 9561-9565, (1994).
Pan, W., et al., "Isolation of virus-neutralizing RNAs from a large pool of random sequences"., Proc. Natl. Acad, Sci. USA, vol. 92, pp. 11509-11513, (1995).
Park, S-J., et al., "Array-based electrical detection of DNA with nanoparticle probes"., Science, vol. 295, pp. 1503-1506, (2002).
Parsons, P.J., et al., "A rapid Zeeman graphite furnace atomic absorption spectrometric method for the determination of lead in blood"., Spectrochimica Acta, vol. 48B, No. 6/7, pp. 925-939, (1993).
Pavlov, A.R., et al., "Determination of lead in environmental water samples by a rapid and portable immunoassay"., ANYL, Book of Abstracts, 219th ACS National Meeting, San Francisco, CA, Mar. 26-30, 2000.
Pavlov, V., et al., "Aptamer-functionalized Au nanoparticles for the amplified optical detection of thrombin"., J. Am. Chem. Soc., vol. 126, No. 38, pp. 11768-11769, (2004).
Pearce, D.A., et al., "Peptidyl chemosensors incorporating a FRET mechanism for detection of Ni(II)"., Bioorganic & Medicinal Chemistry, Letters 8, pp. 1963-1968, (1998).
Pease, A.C., et al., "Light-generated oligonucleotide arrays for rapid DNA sequence analysis"., Proc. Natl. Acad. Sci. USA, vol. 91, pp. 5022-5026, (1994).
Piccirilli, J.A., et al., "Aminoacyl esterase activity of the tetrahymena ribozyme"., Science, New Series, vol. 256, issue 5062, pp. 1420-1424, (1992).
Pley, H.W., et al., "Three-dimensional structure of a hammerhead ribozyme"., Nature, vol. 372, pp. 68-74, (1994).
Potyrailo, R.A., et al., "Adapting selected nucleic acid ligands (aptamers) to biosensors"., Analytical Chemistry, vol. 70, No. 16, pp. 3419-3425, (1998).
Prudent, J.R., et al., "Expanding the scope of RNA catalysis"., Science, New Series, vol. 264, issue 5167, pp. 1924-1927, (1994).
Qiao, H., et al., "Transferability of blood lead determinations by furnace atomic absorption spectrophotometry and continuum background correction"., Clinical Chemistry, vol. 41, No. 10, pp. 1451-1454, (1995).
Rabinowitz, M., et al., "Home refinishing, lead paint, and infant blood lead levels"., American Journal of Public Health, vol. 75, No. 4, pp. 403-404, (1985).
Rajendran, M., et al., "Selecting nucleic acids for biosensor applications"., Combinatorial Chemistry and High Throughput Screening, vol. 5, No. 4, pp. 263-270, (2002).
Rakow, N.A., et al., "A colorimetric sensor array for odour visualization"., Nature, vol. 406, pp. 710-713, (2000).
Rink, S.M., et al., "Creation of RNA molecules that recognize the oxidative lesion 7,8-dihydro-8-hydroxy-2'-deoxyguanosine (8-oxodG) in DNA"., Proc. Natl. Acad. Sci. USA, vol. 95, pp. 11619-11624, (1998).
Robertson, M.P., et al., "Design and optimization of effector-activated ribozyme ligases"., Nucleic Acids Research, vol. 28, No. 8, pp. 1751-1759, (2000).
Robertson, M.P., et al., "In vitro selection of an allosteric ribozyme that transduces analytes to amplicons"., Nature Biotechnology, vol. 17, pp. 62-66, (1999).
Roth, A., et al., "An amino acid as a cofactor for a catalytic polynucleotide"., Proc. Natl. Acad. Sci. USA, vol. 95, pp. 6027-6031, (1998).
Roychowdhury-Saha, M., et al., "Flavin Recognition by an RNA Aptamer Targeted toward FAD"., Biochemistry, vol. 41, No. 8, pp. 2492-2499, (2002).
Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain"., The Journal of Biological Chemistry, vol. 273, No. 32, pp. 20556-20567, (1998).
Rurack, K., et al., "A selective and sensitive fluoroionophore for $Hg^{II}$, $Ag^{I}$, and $Cu^{II}$ with virtually decoupled fluorophore and receptor units"., J. Am. Chem. Soc., vol. 122, No. 5, pp. 968-969, (2000).
Rusconi, C.P., et al., "RNA aptamers as reversible antagonists of coagulation factor Ixa"., Nature, vol. 419, pp. 90-94, (2002).
Sabanayagam, C.R., et al., "Oligonucleotide immobilization on micropatterened streptavidin surfaces"., Nucleic Acids Research, vol. 28, No. 8, e33, pp. i-iv, (2000).
Santoro, S.W. et al., "Mechanism and utility of an RNA-cleaving DNA enzyme"., Biochemistry, vol. 37, No. 38, pp. 13330-13342, (1998).
Santoro, S.W., et al., "A general purpose RNA-cleaving DNA enzyme"., Proc. Natl. Acad. Sci. USA, vol. 94, pp. 4262-4266, (1997).
Santoro, S.W., et al., "RNA Cleavage by a DNA Enzyme with Extended Chemical Functionality"., J. Am. Chem. Soc., vol. 122, No. 11, pp. 2433-2439, (2000).
Sassanfar, M., et al., "An RNA motif that binds ATP"., Nature, vol. 364, pp. 550-553, (1993).
Schwartz, J., et al., "The risk of lead toxicity in homes with lead paint hazard"., Environmental Research, vol. 54, No. 1, pp. 1-7, (1991).
Scott, W.G., et al., "The crystal structure of an all-RNA hammerhead ribozyme: A proposed mechanism for RNA catalytic cleavage"., Cell, vol. 81, pp. 991-1002, (1995).
Scott, W.G., "RNA catalysis"., Current Opinion in Structural Biology, vol. 8, pp. 720-726, (1998).
Search results of key word search of medline, Mar. 26, 2000.
Search results of key word search on Chemical Abstracts, Mar. 24, 2000.
Search results of key word search from various databases, Mar. 24, 2000.
Seeman, N.C., et al., "Synthetic DNA knots and catenanes"., New Journal of Chemistry, vol. 17, pp. 739-755, (1993).
Seeman, N.C., et al., "Emulating biology: Building nanostructures from the bottom up"., Proc. Natl. Acad. Sci., vol. 99, suppl. 2, pp. 6451-6455, (2002).
Seeman, N.C., "DNA in a material world"., Nature, vol. 421, pp. 427-431, (2003).
Seetharaman, S., et al., "Immobilized RNA switches for the analysis of complex chemical and biological mixtures"., Nature Biotechnology, vol. 19, pp. 336-341, (2001).
Sen, D., et al., "DNA enzymes"., Current Opinion in Chemical Biology, vol. 2, pp. 680-687, (1998).
Shaiu, W-L., et al., "Atomic force microscopy of oriented linear DNA molecules labeled with 5nm gold spheres"., Nucleic Acids Research, vol. 21, No. 1, pp. 99-103, (1993).
Shaw, S.Y., et al., "Knotting of a DNA chain during ring closure"., Science, New Series, vol. 260, issue 5107, pp. 533-536, (1993).
Shekhtman, E.M., et al., "Stereostructure of replicative DNA catenanes from eukaryotic cells"., New Journal of Chemistry, vol. 17, pp. 757-763, (1993).
Sigurdsson, S.T., et al., "Small ribozymes"., RNA Structure and Function, Cold Spring Harbor Laboratory Press (Monograph 35), pp. 339-375, (1998).
Singh, K.K., et al., "Fluorescence Polarization for Monitoring Ribozyme Reactions in Real-Time"., Biotechniques, vol. 29, No. 2, pp. 344-351, (2000).
Smith, F.W., et al., "Quadruplex structure of oxytricha telomeric DNA oligonucleotides"., Nature, vol. 356, pp. 164-168, (1992).
Smith, J.O., et al., "Molecular recognition of PNA-containing hybrids: Spontaneous assembly of helical cyanine dye aggregates on PNA templates"., J. Am. Chem. Soc., vol. 121, No. 12, pp. 2686-2695, (1999).
Soriaga, M.P., et al., "Determination of the orientation of aromatic molecules adsorbed on platinum electrodes: The effect of solute concentration"., J. Am. Chem. Soc., vol. 104, No. 14, pp. 3937-3945, (1982).
Soukup, G.A., et al., "Engineering precision RNA molecular switches"., Proc. Natl. Acad. Sci. USA, vol. 96, pp. 3584-3589, (1999).

(56) References Cited

OTHER PUBLICATIONS

Soukup, G.A., et al., "Allosteric nucleic acid catalysts"., Current Opinion in Structural Biology, vol. 10, pp. 318-325, (2000).
Srisawat, C., et al., "Sephadex-binding RNA ligands: rapid affinity purification of RNA from complex RNA mixtures"., Nucleic Acids Research, vol. 29, No. 2 e4, pp. 1-5, (2001).
Stage-Zimmermann, T.K., et al., "Hammerhead ribozyme kinetics"., RNA, vol. 4, pp. 875-889, (1998).
Stojanovic, M.N., et al., "Aptamer-based colorimetric probe for cocaine"., J. Am. Chem. Soc., vol. 124, No. 33, pp. 9678-9679, (2002).
Stojanovic, M.N., et al., "Aptamer-based folding fluorescent sensor for cocaine"., Journal of the American Chemical Society, vol. 123, No. 21, pp. 4928-4931, (2001).
Stojanovic, M.N., et al., "Fluorescent sensors based on aptamer self-assembly"., Journal of the American Chemical Society, vol. 122, No. 46, pp. 11547-11548, (2000).
Storhoff, J.J., et al., "Programmed materials synthesis with DNA"., Chem. Rev., vol. 99, No. 7, pp. 1849-1862, (1999).
Storhoff, J.J., et al., "Facile colorimetric detection of polynucleotides based on gold nanoparticle probes"., Proceedings of the 1998 ERDEC Scientific Conference on Chemical and Biological Defense Research, Nov. 17-20, 1998, Aberdeen Proving Ground, pp. 221-226, (1999).
Storhoff, J.J., et al., "What Controls the Optical Properties of DNA-Linked Gold Nanoparticle Assemblies?"., J. Am. Chem. Soc., vol. 122, No. 19, pp. 4640-4650, (2000).
Storhoff, J.J., et al., "One-pot colorimetric differentiation of polynucleotides with single base imperfections using gold nanoparticle probes"., Journal of the American Chemical Society, vol. 120, No. 9, pp. 1959-1964, (1998).
Streicher, B., et al., "Lead cleavage site in the core structure of group I intron-RNA"., Nucleic Acids Research, vol. 21, No. 2, pp. 311-317, (1993).
Sugimoto, N., et al., "Site-specific cleavage reaction catalyzed by leadzyme is enhanced by combined effect of lead and rare earth ions"., FEBS Letters, vol. 393, pp. 97-100, (1996).
Sun, L.Q., et al., "Catalytic nucleic acids: From lab to applications"., Pharmacological Reviews, vol. 52, pp. 325-347, (2000).
Tahan, J.E., et al., "Electrothermal atomic absorption spectrometric determination of Al, Cu, Ge, Pb, V and Zn in clinical samples and in certified environmental reference materials"., Analytica Chimica Acta, vol. 295, pp. 187-197, (1994).
Takagi, Y., et al., "Survey and Summary: Recent advances in the elucidation of the mechanisms of action of ribozymes"., Nucleic Acids Research, vol. 29, No. 9, pp. 1815-1834, (2001).
Tang, J., et al., "Rational design of allosteric ribozymes"., Chemistry & Biology, vol. 4, No. 6, pp. 453-459, (1997).
Tang, J., et al., "Structural diversity of self-cleaving ribozymes"., Proc. Natl. Acad. Sci. USA, vol. 97, No. 11, pp. 5784-5789, (2000).
Tanner, N.K., "Biochemistry of hepatitis delta virus catalytic RNAs"., Ribozymes in the Gene Therapy of Cancer, Chapter 3, pp. 23-38, (1998).
Tao, J., et al., "Arginine-Binding RNAs Resembling TAR Identified by in Vitro Selection".,Biochemistry, vol. 35, No. 7, pp. 2229-2238, (1996).
Tarasow, T.M., et al., "RNA-catalysed carbon-carbon bond formation"., Nature, vol. 389, pp. 54-57, (1997).
Telting-Diaz, M., et al., "Mass-produced ionophore-based fluorescent microspheres for trace level determination of lead ions"., Analytical Chemistry, vol. 74, No. 20, pp. 5251-5256, (2002).
Thompson, R.B., et al., "Determination of Picomolar Concentrations of Metal Ions Using Fluorescence Anisotropy: Biosensing with a "Reagentless" Enzyme Transducer"., Analytical Chemistry, vol. 70, No. 22, pp. 4717-4723, (1998).
Timmons, C.O., et al., "Investigation of Fatty Acid Monolayers on Metals by Contact Potential Measurements", Journal of Physical Chemistry, vol. 69, No. 3, pp. 984-990, (1965).
Tompkins, H.G., et al., "The study of the gas-solid interaction of acetic acid with a cuprous oxide surface using reflection-absorption spectroscopy"., Journal of Colloid and Interface Science, vol. 49, No. 3, pp. 410-421, (1974).
Travascio, P., et al., "A ribozyme and a catalytic DNA with peroxidase activity: active sites versus cofactor-binding sites"., Chemistry & Biology, vol. 6, No. 11, pp. 779-787, (1999).
Tsang, J., et al., "In vitro evolution of randomized ribozymes"., Methods in Enzymology, vol. 267, pp. 410-426, (1996).
Tsien, R.Y., "Fluorescent and photochemical probes of dynamic biochemical signals inside living cells"., Fluorescent Chemosensors for Ion and Molecule Recognition, (ed. Czarnik, A. W.), chapter 9, pp. 130-146, American Chemical Society, (1993).
Tuerk, C., et al., "RNA pseudoknots that inhibit human immunodeficiency virus type 1 reverse transcriptase"., Proc. Natl. Acad. Sci. USA, vol. 89, pp. 6988-6992, (1992).
Tuerk, C., et al., "Systematic evolution of ligands by exponential enrichment: RNA ligands to bacteriophage T4 DNA polymerase"., Science, New Series, vol. 249, issue 4968, pp. 505-510, (1990).
Tyagi, S., et al., "Molecular Beacons: Probes that fluoresce upon hybridization"., Nature Biotechnology, vol. 14, pp. 303-308, (1996).
Tyagi, S., et al., "Multicolor molecular beacons for allele discrimination"., Nature Biotechnology, vol. 16, pp. 49-53, (1998).
Tyagi, S., et al., "Wavelength-shifting molecular beacons"., Nature Biotechnology, vol. 18, pp. 1191-1196, (2000).
Ueyama, H., "A novel potassium sensing in aqueous media with a synthetic oligonucleotide derivative. Fluorescence resonance energy transfer associated with guanine quartet-potassium ion complex formation"., J. Am. Chem. Soc., vol. 124, No. 48, pp. 14286-14287, (2002).
Uphoff, K.W., et al., "In vitro selection of aptamers: the dearth of pure reason"., Current Opinion in Structural Biology, vol. 6, pp. 281-288, (1996).
Vaish, N.K., et al., "In vitro selection of a purine nucleotide-specific hammerhead-like ribozyme"., Proc. Natl. Acad. Sci. USA, vol. 95, pp. 2158-2162, (1998).
Valadkhan, S., et al., "Splicing-related catalysis by protein-free snRNAs"., Nature, vol. 413, pp. 701-707, (2001).
Vianini, E., et al., "In vitro selection of DNA aptamers that bind L-tyrosinamide"., Bioorganic & Medicinal Chemistry, vol. 9, pp. 2543-2548, (2001).
Walkup, G.K., et al., "Design and Evaluation of a Peptidyl Fluorescent Chemosensor for Divalent Zinc"., J. Am. Chem. Soc., vol. 118, No. 12, pp. 3053-3054, (1996).
Wallace, S.T., et al., In vitro selection and characterization of streptomycin-binding RNAs: recognition discrimination between antibiotics. RNA, vol. 4, pp. 112-123, (1998).
Wallis, M.G., et al., "A novel RNA motif for neomycin recognition"., Chemistry & Biology, vol. 2, No. 8, pp. 543-552, (1995).
Wallis, M.G., et al., "In vitro selection of a viomycin-binding RNA pseudoknot"., Chemistry & Biology, vol. 4, No. 5, pp. 357-366, (1997).
Walter, F., et al., "Folding of the four-way RNA junction of the hairpin ribozyme"., Biochemistry, vol. 37, No. 50, pp. 17629-17636, (1998).
Walter, N.G., et al., "The hairpin ribozyme: structure, assembly and catalysis"., Current Opinion in Chemical Biology, vol. 2, pp. 24-30, (1998).
Wang, D.Y., et al., "A general strategy for effector-mediated control of RNA-cleaving ribozymes and DNA enzymes"., J. Mol. Biol., vol. 318, pp. 33-43, (2002).
Wang, F., et al., "Sphingosine-1-phosphate Inhibits Motility of Human Breast Cancer Cells Independently of Cell Surface Receptors"., Cancer Research, vol. 59, pp. 6185-6191, (1999).
Wang, J., "Survey and Summary: From DNA biosensors to gene chips"., Nucleic Acids Research, vol. 28, No. 16, pp. 3011-3016, (2000).
Wang, K.Y., et al., "A DNA aptamer which binds to and inhibits thrombin exhibits a new structural motif for DNA"., Biochemistry, vol. 32, No. 8, pp. 1899-1904, (1993).
Wang, Y., et al., "Assembly and characterization of five-arm and six-arm DNA branched junctions"., Biochemistry, vol. 30, pp. 5667-5674, (1991).

(56) References Cited

OTHER PUBLICATIONS

Wang, Y., et al., "RNA molecules that specifically and stoichiometrically bind aminoglycoside antibiotics with high affinities"., Biochemistry, vol. 35, No. 38, pp. 12338-12346, (1996).
Wecker, M., et al., "In vitro selection of a novel catalytic RNA: characterization of a sulfur alkylation reaction and interaction with a small peptide"., RNA, vol. 2, pp. 982-994, (1996).
Wedekind, J.E., et al., "Crystal structure of a lead-dependent ribozyme revealing metal binding sites relevant to catalysis"., Nature Structural Biology, vol. 6, No. 3, pp. 261-268, (1999).
Wedekind, J.E., et al., "Crystal structure of the leadzyme at 1.8 Å Resolution: Metal ion binding and the implications for catalytic mechanism and allo site ion regulation"., Biochemistry, vol. 42, No. 32, pp. 9554-9563, (2003).
Wells, R.D., "Unusual DNA structures"., Journal of Biological Chemistry, vol. 263, No. 3, pp. 1095-1098, (1988).
Werstuck, G., et al., "Controlling gene expression in living cells through small molecule-RNA interactions"., Science, vol. 282, pp. 296-298, (1998).
Whaley, S.R., et al., "Selection of peptides with semiconductor binding specificity for directed nanocrystal assembly"., Nature, vol. 405, pp. 665-668, (2000).
Whitesides, G.M., et al., "Self-assembled monolayers and lithography"., Proceedings of the Robert A. Welch Foundation 39th Conference on Chemical Research on Nanophase Chemistry, pp. 109-121, Houston, TX, Oct. 23-24, 1995.
Wiegand, T.W., et al., "High-affinity oligonucleotide ligands to human IgE inhibit binding to Fc epsilon receptor I"., The Journal of Immunology, vol. 157, pp. 221-230, (1996).
Wiegand, T.W., et al., "Selection of RNA amide synthases"., Chemistry & Biology, vol. 4, No. 9, pp. 675-683, (1997).
Williams, K.P., et al., "Bioactive and nuclease-resistant L-DNA ligand of vasopressin"., Proc. Natl. Acad. Sci. USA, vol. 94, pp. 11285-11290, (1997).
Williams, K.P., et al., "Selection of novel $Mg^{2+}$-dependent self-cleaving ribozymes" The EMBO Journal, vol. 14, No. 18, pp. 4551-4557, (1995).
Wilson, C., et al., "Functional requirements for specific ligand recognition by a biotin-binding RNA Pseudoknot"., Biochemistry, vol. 37, No. 41, pp. 14410-14419, (1998).
Wilson, C., et al., "In vitro evolution of a self-alkylating ribozyme"., Nature, vol. 374, pp. 777-782, (1995).
Wilson, C., et al., "Isolation of a fluorophore-specific DNA aptamer with weak redox activity"., Chemistry & Biology, vol. 5, No. 11, pp. 609-617, (1998).
Wilson, D.S., et al., "In vitro selection of functional nucleic acids"., Annu. Rev. Biochem. vol. 68, pp. 611-647, (1999).
Winkler, J.D., et al., "Photodynamic Fluorescent Metal Ion Sensors with Parts per Billion Sensitivity"., J. Am. Chem. Soc., vol. 120, No. 13, pp. 3237-3242, (1998).
Wittmann, C., et al.,"Microbial and Enzyme sensors for environmental monitoring"., Handbook of Biosensors and Electronic Noses: Medicine, Food, and the Environment, pp. 299-332, (1997).
Xia, P., et al., "Activation of Sphingosine Kinase by Tumor Necrosis Factor-A Inhibits Apoptosis in Human Endothelial Cells"., Journal of Biological Chemistry, vol. 274, No. 48, pp. 34499-34505, (1999).
Yan, H., et al., "DNA-Templated self-assembly of protein arrays and highly conductive nanowires"., Science, vol. 301, pp. 1882-1884, (2003).
Yang, Q., et al., "DNA ligands that bind tightly and selectively to cellobiose"., Proc. Natl. Acad. Sci. USA, vol. 95, pp. 5462-5467, (1998).
English Translation of Yang, Y., et al., "Measurement of lead and magnesium in distilled spirits using inductively coupled plasma optical emission spectrometry viewed from the end"., Analytical Chemistry (Fenxi Huaxue), Chinese Journal of Analytical Chemistry, vol. 25, No. 9, pp. 1114-1117, (1997).
Yurke, B., et al., "A DNA-fuelled molecular machine made of DNA"., Nature, vol. 406, pp. 605-608, (2000).
Zhang, B., et al., "Peptide bond formation by in vitro selected ribozymes"., Nature, vol. 390, pp. 96-100, (1997).
Zhang, P., et al., "Design of a molecular beacon DNA probe with two fluorophores"., Angewandte Chemie International Edition, vol. 40, No. 2, pp. 402-405, (2001).
Zillmann, M., et al., "In vitro optimization of truncated stem-loop II variants of the hammerhead ribozyme for cleavage in low concentrations of magnesium under non-turnover conditions"., RNA, vol. 3, pp. 734-747, (1997).
Zimmerman, J.M., et al., "In vivo selection of spectinomycin-binding RNAs"., Nucleic Acids Research, vol. 30, No. 24, pp. 5425-5435, (2002).
Zimmermann, G.R., et al., "Molecular interactions and metal binding in the theophylline-binding core of an RNA aptamer"., RNA, vol. 6, pp. 659-667, (2000).
International Search Report dated Nov. 21, 2005 for PCT application No. PCT/US2005/001060.
Supplemental International Search Report dated Jan. 10, 2006 for PCT application No. PCT/US2005/001060.
Liu, J., et al., "Size control, metal substitution, and catalytic application of cryptomelane nanomaterials prepared using cross-linking reagents"., Chem. Mater., vol. 16, No. 2, pp. 276-285, (2004).
Cake, K.M., et al., "Partition of circulating lead between serum and red cells is different for internal and external sources of lead"., American Journal of Industrial Medicine, vol. 29, pp. 440-445, (1996).
International Search Report dated Aug. 31, 2004 for PCT application No. PCT/US2004/002946.
Hazarika, P., et al., "Reversible switching of DNA-Gold nanoparticle aggregation"., Angewandte Chemie International Edition, vol. 43, No. 47, pp. 6469-6471, (2004).
International Search Report dated May 29, 2006 for PCT application No. PCT/US2005/037896.
Liu, J., et al., "Improving fluorescent DNAzyme biosensors by combining Inter- and Intramolecular quenchers"., Analytical Chemistry, vol. 75, No. 23, pp. 6666-6672, (2003).
Liu, J., et al., "Stimuli-responsive disassembly of nanoparticle aggregates for light-up colorimetric sensing"., Journal of the American Chemical Society, vol. 127, No. 36, pp. 12677-12683, (2005).
European Search Report dated Jul. 10, 2006 for PCT application No. PCT/US2003/12576.
Tanner, F.C., et al., "Transfection of human endothelial cells"., Cardiovascular research, vol. 35, pp. 522-528, (1997).
International Search Report dated Nov. 17, 2006 for PCT application No. PCT/US2006/001627.
Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).
Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).
Levy, M., et al., "Exponential growth by cross-catalytic cleavage of deoxyribozymogens",PNAS, vol. 100, No. 11, pp. 6416-6421, (2003).
Beyer, S., et al., "A modular DNA signal translator for the controlled release of a protein by an aptamer", Nucleic Acids Research, vol. 34, No. 5, pp. 1581-1587, (2006).
Frauendorf, C., et al., "Detection of small organic analytes by fluorescing molecular switches", Bioorganic & Medicinal Chemistry, vol. 9, pp. 2521-2524, (2001).
Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).
Liu, J., et al., "Optimization of a $Pb^{2+}$ directed gold nanoparticle/DNAzyme assembly and its application as a colorimetric biosensor for $Pb^{2+}$", Chem. Mater., vol. 16, No. 17, pp. 3231-3238, (2004).
Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).

(56) References Cited

OTHER PUBLICATIONS

Product Description: Pall Corporation, "Immunochromatographic, lateral flow or strip tests development ideas", found at: http://www.pall.com/34445_4154.asp, 7 pages, (1998).
Liu, J., et al., "Fast colorimetric sensing of adenosine and cocaine based on a general sensor design involving aptamers and nanoparticles", Angew. Chem. Int. Ed., vol. 45, pp. 90-94, (2006).
Liu, J., et al., "A simple and sensitive "dipstick" test in serum based on lateral flow separation of aptamer-linked nanostructures", Angewandte Chemie International Edition, vol. 45, pp. 7955-7959, (2006).
Jiang, P. et al., "Fluorescent detection of zinc in biological systems: recent development on the design of chemosensors and biosensors", Coordination Chemistry Reviews, vol. 248, pp. 205-229, (2004).
Lim, M.H. et al., "Metal-based turn-on fluorescent probes for sensing nitric oxide", Accounts of Chemical Research, vol. 40, No. 1, pp. 41-51, (2007).
Yoon, S. et al., "Screening mercury levels in fish with a selective fluorescent chemosensor", Journal of the American Chemical Society, vol. 127, pp. 16030-16031, (2005).
Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).
He, Q. et al., "A selective fluorescent sensor for detecting lead in living cells", Journal of the American Chemical Society, vol. 128, pp. 9316-9317, (2006).
Zeng, L. et al., "A selective turn-on fluorescent sensor for imaging copper in living cells", Journal of the American Chemical Society, vol. 128, pp. 10-11, (2006).
Wegner, S.V. et al., "Design of an emission ratiometric biosensor from MerR family proteins: A sensitive and selective sensor for $Hg^{2+}$", Journal of the American Chemical Society, vol. 129, pp. 3474-3475, (2007).
Nolan, E.M. et al., "Turn-on and ratiometric mercury sensing in water with a red-emitting probe", Journal of the American Chemical Society, vol. 129, pp. 5910-5918, (2007).
Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).
Torrado, A. et al., "Exploiting polypeptide motifs for the design of selective Cu(II) ion chemosensors" Journal of the American Chemical Society, vol. 120, pp. 609-610, (1998).
Grandini, P. et al., "Exploiting the self-assembly strategy for the design of selective $Cu^{II}$ ion chemosensors", Angew. Chem. Int. Ed, vol. 38, No. 20, pp. 3061-3064, (1999).
Klein, G. et al., "A fluorescent metal sensor based on macrocyclic chelation", Chem. Comm., pp. 561-562, (2001).
Zheng, Y. et al., "A new fluorescent chemosensor for copper ions based on tripeptide glycyl-histidyl-lysine (GHK)", Organic Letters, vol. 3, No. 21, pp. 3277-3280, (2001).
Boiocchi, M. et al., "A two-channel molecular dosimeter for the optical detection of copper(II)" Chem. Comm, pp. 1812-1813, (2003).
Zheng, Y. et al., "Peptidyl fluorescent chemosensors for the detection of divalent copper", Analytical Chemistry, vol. 75, No. 7, pp. 1706-1712, (2003).
Zheng, Y. et al., "Development of fluorescent film sensors for the detection of divalent copper", Journal of the American Chemical Society, vol. 125, pp. 2680-2686, (2003).
Roy, B.C. et al., "Synthesis of new, pyrene-containing metal-chelating lipids and sensing of cupric ions", Organic Letters, vol. 5, No. 1, pp. 11-14, (2003).
Kaur, S. et al., "Photoactive chemosensors 4: a $Cu^{2+}$ protein cavity mimicking fluorescent chemosensor for selective $Cu^{2+}$ recognition", Tetrahedron Letters, vol. 45, pp. 5081-5085, (2004).
Mei, Y. et al., "A selective and sensitive chemosensor for $Cu^{2+}$ based on 8-hydroxyquinoline", Tetrahedron Letters, vol. 47, pp. 2447-2449, (2006).
Zhang, X-B. et al., "A highly selective fluorescent sensor for $Cu^{2+}$ based on 2-(2'-hydroxyphenyl) benzoxazole in a poly(vinyl chloride) matrix", Analytica Chimica Acta, vol. 567, pp. 189-195, (2006).
Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).
Kim, S. H. et al., "$Hg^{2+}$ selective off-on and $Cu^{2+}$-selective on-off type fluoroionophore based upon cyclam", Organic Letters, vol. 8, No. 3, pp. 371-374, (2006).
White, B. R. et al., "Fluorescent peptide sensor for the selective detection of $Cu^{2+}$", Talanta, vol. 71, pp. 2015-2020, (2007).
Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).
Dujols, V. et al., "A long-wavelength fluorescent chemodosimeter selective for Cu(II) ion in water", Journal of the American Chemical Society, vol. 119, pp. 7386-7387, (1997).
Yang, J-S. et al., "$Cu^{2+}$-induced blue shift of the pyrene excimer emission: a new signal transduction mode of pyrene probes", Organic Letters, vol. 3, No. 6, pp. 889-892, (2001).
Kaur, S. et al., "Photoactive chemosensors 3: a unique case of fluorescence enhancement with Cu(II)", Chem. Comm., pp. 2840-2841, (2002).
Wu, Q. et al., "Catalytic signal amplification using a heck reaction. An example in the fluorescence sensing of Cu(II)", Journal of the American Chemical Society, vol. 126, pp. 14682-14683, (2004).
Royzen, M. et al., "Ratiometric displacement approach to Cu(II) sensing by fluorescence", Journal of the American Chemical Society, vol. 127, pp. 1612-1613, (2005).
Xu, Z. et al., "Ratiometric and selective fluorescent sensor for $Cu^{II}$ based on internal charge transfer (ICT)", Organic Letters, vol. 7, No. 5, pp. 889-892, (2005).
Wen, Z-C. et al., "A highly selective charge transfer fluoroionophore for $Cu^{2+}$", Chem. Commun., pp. 106-108, (2006).
Yang, H. et al., "Highly selective ratiometric fluorescent sensor for Cu(II) with two urea groups", Tetrahedron Letters, vol. 47, pp. 2911-2914, (2006).
Martinez, R. et al., "2-aza-1,3-butadiene derivatives featuring an anthracene or pyrene unit: highly selective colorimetric and fluorescent signaling of $Cu^{2+}$ cation", Organic Letters, vol. 8, No. 15, pp. 3235-3238, (2006).
Navani, N.K. et al., "Nucleic acid aptamers and enzymes as sensors", Current Opinion in Chemical Biology, vol. 10, pp. 272-281, (2006).
Liu, J. et al., "A catalytic beacon sensor for uranium with parts-per-trillion sensitivity and millionfold selectivity", Proceedings of the National Academy of Science, vol. 104, No. 7, pp. 2056-2061, (2007).
Georgopoulos, P.G. et al., "Environmental copper: its dynamics and human exposure issues", Journal of Toxicology and Environmental Health, Part B, vol. 4, pp. 341-394, (2001).
Hertzberg, R.P. et al., "Cleavage of DNA with methidiumpropyl-EDTA-iron(II): reaction conditions and product analyses", Biochemistry, vol. 23, pp. 3934-3945, (1984).
Yazzie, M. et al., "Uranyl acetate causes DNA single strand breaks in vitro in the presence of ascorbate (Vitamin C)", Chem. Res. Toxicol., vol. 16, pp. 524-530, (2003).
Bolletta, F. et al., "A [$Ru^{II}$ (bipy)$_3$]-[1,9-diamino-3,7-diazanonane-4,6-dione] two-component system as an efficient on-off luminescent chemosensor for $Ni^{2+}$ and $Cu^{2+}$ in water, based on an ET (energy transfer) mechanism", Journal of the Chemical Society, Dalton Transactions, pp. 1381-1385, (1999).
Carmi, N. et al., "Characterization of a DNA-cleaving deoxyribozyme", Bioorganic & Medicinal Chemistry, vol. 9, issue 10, pp. 2589-2600, (2001).
Liu, J. et al., "A DNAzyme catalytic beacon sensor for paramagnetic $Cu^{2+}$ ions in aqueous solution with high sensitivity and selectivity", Journal of the American Chemical Society, 2 pages, (2007), ASAP Web Release Date: Jul. 24, 2007.
Tanaka, K. et al., "Programmable self-assembly of metal ions inside artificial DNA duplexes", Nature Nanotechnology, vol. 1, pp. 190-194, (2006).

(56) References Cited

OTHER PUBLICATIONS

Achenbach, J.C. et al., "DNAzymes: From creation in vitro to application in vivo", Current Pharmaceutical Biotechnology, vol. 5, pp. 321-336, (2004).
Balaji, T. et al., "Optical sensor for the visual detection of mercury using mesoporous silica anchoring porphyrin moiety", the Analyst, vol. 130, pp. 1162-1167, (2005).
Caballero, A. et al., "Highly selective chromogenic and redox or fluorescent sensors of $Hg^{2+}$ in aqueous environment based on 1,4-disubstituted azines", Journal of the American Chemical Society, vol. 127, pp. 15666- 15667, (2005).
Chan, W.H. et al., "Development of a mercury ion-selective optical sensor based on fluorescence quenching of 5,10,15, 20-tetraphenylporphyrin", Analytica Chimica Acta, vol. 444, pp. 261-269, (2001).
Chen, P. et al., "A general strategy to convert the merR family proteins into highly sensitive and selective fluorescent biosensors for metal ions", Journal of the American Chemical Society, vol. 126, pp. 728-729, (2004).
Chiuman, W. et al., "Efficient signaling platforms built from a small catalytic DNA and doubly labeled fluorogenic substrates", Nucleic Acids Research, vol. 35, No. 2, pp. 401-405, (2007).
Cruz, R.P.G. et al., "Dinucleotide junction cleavage versatility of 8-17 deoxyribozyme", Chemistry & Biology, vol. 11, pp. 57-67, (2004).
Frasco, M.F. et al., "Mechanisms of cholinesterase inhibition by inorganic mercury", the FEBS Journal, vol. 274, pp. 1849-1861, (2007).
Guo, X. et al., "A highly selective and sensitive fluorescent chemosensor for $Hg^{2+}$ in neutral buffer aqueous solution", The Jouranl of the American Chemical Society, vol. 126, pp. 2272-2273, (2004).
Harris, H.H. et al., "The chemical form of mercury in fish", Science, vol. 301, pp. 1203, (2003).
Ha-Thi, M-H. et al., "Highly selective and sensitive phosphane sulfide derivative for the detection of $Hg^{2+}$ in an organoaqueous medium", Organic Letters, vol. 9, No. 6, pp. 1133-1136, (2007).
Joyce, G.F. et al., "Directed evolution of nucleic acid enzymes", Annual Review Biochem., vol. 73, pp. 791-836, (2004).
Ko, S-K. et al., "In vivo monitoring of mercury ions using a rhodamine-based molecular probe", Journal of the American Chemical Society, vol. 128, pp. 14150-14155, (2006).
Kuswandi, B. et al., "Capillary optode: determination of mercury(II) in aqueous solution", Analytical Letters, vol. 32, No. 9. 4, pp. 649-664, (1999).
Kuswandi, B. et al., "Selective pool optode for mercury ion sensing in aqueous solution", Sensors and Actuators B, vol. 74, pp. 131-137, (2001).
Lee, J-S. et al., "Colorimetric detection of mercuric ion ($Hg^{2+}$ ) in aqueous media using DNA-functionalized gold nanoparticles", Angewandte Chemie International Edition, vol. 46, pp. 4093-4096, (2007).
Liu, B. et al., "A selective fluorescent ratiometric chemodosimeter for mercury ion", Chem. Communications, pp. 3156-3158, (2005).
Liu, J. et al., "Fluorescent DNAzyme biosensors for metal ions based on catalytic molecular beacons", Methods in Molecular Biology, vol. 335, pp. 275-288, (2006).
Matsushita, M. et al., "A blue fluorescent antibody-cofactor sensor for mercury", Organic Letters, vol. 7, No. 22, pp. 4943-4946, (2005).
Miyake, Y. et al., "$Mercury^{II}$-mediated formation of thymine-$Hg^{II}$-thymine base pairs in DNA duplexes", Journal of the American Chemical Society, vol. 128, No. 7, pp. 2172-2173, (2006).
Nolan, E.M. et al., "A "turn-on" fluorescent sensor for the selective detection of mercuric ion in aqueous media", Journal of the American Chemical Society, vol. 125, pp. 14270-14271, (2003).
Ono, A. et al., "highly selective oligonucleotide-based sensor for mercury (II) in aqueous solutions", Angew. Chem. Int. Ed., vol. 43, pp. 4300-4302, (2004).
Ostatna, V. et al., "Self-assembled monolayers of thiol-end-labeled DNA at mercury electrodes", Langmuir, vol. 22, pp. 6481-6484, (2006).
Prodi, L. et al., "An effective fluorescent achemosensor for mercury ions", Journal of the American Chemical Society, vol. 122, No. 28, pp. 6769-6770, (2000).
Silverman, S.K., "Survey and Summary: in vitro selection, characterization, and application of deoxyribozymes that cleave RNA", Nucleic Acids Research, vol. 33, No. 19, pp. 6151-6163, (2005).
Song, K.C. et al., "Fluorogenic $Hg^{2+}$-selective chemodosimeter derived from 8-hydroxyquinoline", Organic Letters, vol. 8, No. 16, pp. 3413-3416, (2006).
Szurdoki, F. et al., "A combinatorial approach to discover new chelators for optical metal ion sensing", Analytical Chemistry, vol. 72, No. 21, pp. 5250-5257, (2000).
Tanaka, Y. et al., "$^{15}N$-$^{15}N$ J-coupling across $Hg^{II}$: Direct observation of $Hg^{II}$-mediated T-T base pairs in a DNA duplex" Journal of the American Chemical Society, vol. 129, No. 2, pp. 244-245, (2007).
Jacoby, M. "Mercury Sensor—Analytical Chemistry: Colorimetric method is sensitive and selective", Chemical & Engineering News, pp. 15, May 7, 2007.
Vannela, R. et al., "In vitro selection of Hg (II) and as (V)-dependent RNA-cleaving DNAzymes", Environmental Engineering Science, vol. 24, No. 1, pp. 73-84, (2007).
Vaughan, A.A. et al., "Optical fibre reflectance sensors for the detection of heavy metal ions based on immobilized Br-PADAP", Snesors and Actuators B, vol. 51, pp. 368-376, (1998).
Virta, M. et al., "A luminescence-based mercury biosensor", Analytical Chemistry, vol. 67, No. 3, pp. 667-669, (1995).
Wang, J. et al., "Detecting $Hg^{2+}$ ions with an ICT fluorescent sensor molecule: Remarkable emission spectra shift and unique selectivity", Journal of Organic Chemistry, vol. 71, pp. 4308-4311, (2006).
Wang, J. et al., "A series of polyamide receptor based PET fluorescent sensor molecules: Positively cooperative $Hg^{2+}$ ion binding with high sensitivity", Organic Letters, vol. 8, No. 17, pp. 3721-3724, (2006).
Widmann, A. et al., "Mercury detection in seawater using a mercaptoacetic acid modified gold microwire electrode", Electroanalysis, vol. 17, No. 10, pp. 825-831, (2005).
Xiao, Y. et al., "Electrochemical detection of parts-per-billion lead via an electrode-bound DNAzyme assembly", Journal of the American Chemical Society, vol. 129, pp. 262-263, (2007).
Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).
Yang, Y-K. et al., "A rhodarnine-based fluorescent and colorimetric chemodosimeter for the rapid detection of Hg2+ ions in aqueous media", Journal of the American Chemical Society, vol. 127, pp. 16760-16761, (2005).
Zhang, X-B. et al "An optical fiber chemical sensor for mercury ions based on a porphyrin dimmer", Analytical Chemistry, vol. 74, No. 4, pp. 821-825, (2002).
Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).
Zhao, Y. et al., "Tuning the sensitivity of a foldamer-based mercury sensor by its folding energy", Journal of the American Chemical Society, vol. 128, No. 31, pp. 9988-9989, (2006).
Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).
Zuker, M., "Mfold web server for nucleic acid folding and hybridization prediction", Nucleic Acids Research, vol. 31, No. 13, pp. 3406-3415, (2003).
International Search Report dated May 10, 2007 for PCT application No. PCT/US2006/030617.
Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).
Liu, J. et al., "Smart nanomaterials responsive to multiple chemical stimuli with controllable cooperativity", Advanced Materials, vol. 18, No. 13, pp. 1667-1671, (2006).

(56) References Cited

OTHER PUBLICATIONS

Nutiu, R. et al., "Signaling aptamers for monitoring enzymatic activity and for inhibitor screening", Chembiochem—A European Journal of Chemical Biology, vol. 5, No. 8, pp. 1139-1144, (2004).
Nutiu, R. et al., "Structure-switching signaling aptamers: Transducing molecular recognition into fluorescence signaling", Chemistry—A European Journal, vol. 10, No. 8, pp. 1868-1876, (2004).
International Search Report dated Jul. 31, 2007 for PCT application No. PCT/US2007/064055.
Ahern, H., "Biochemical, reagent kits offer scientists good return on investment", The Scientist, vol. 9, No. 15, pp. 20-22, (1995).
Homann, M. et al., "Dissociation of long-chain duplex RNA can occur via strand displacement in vitro: biological implication", Nucleic Acids Research, vol. 24, No. 22, pp. 4395-4400, (1996).
Alivisatos, A.P. et al., "Quantum dots as cellular probes", Annual Review Biomed. Eng, vol. 7, pp. 55-76, (2005).
Dyadyusha, L et al., "Quenching of CdSe quantum dot emission, a new approach for biosensing", Chemical Communication, pp. 3201-3203, (2005).
Ellington, A.D. et al., "In vitro selection of RNA molecules that bind specific ligands", Nature, vol. 346, pp. 818-822, (1990).
Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).
Goldman, E.R. et al., "Multiplexed toxin analysis using four colors of quantum dot fluororeagents", Analytical Chemistry, vol. 76, No. 3, pp. 684-688, (2004).
Gueroui, Z. et al., "Single-molecule measurements of gold-quenched quantum dots", Physical Review Letters, vol. 93, No. 16, pp. 166108/1-166108/4, (2004).
Han, M. et al., "Quantum-dot-tagged microbeads for multiplexed optical coding of biomolecules", Nature Biotechnology, vol. 19, pp. 631-635, (2001).
Hansen, J.A. et al., "Quantum-dot/Aptamer-based ultrasensitive multi-analyte electrochemical biosensor", Journal of the American Chemical Society, vol. 128, No. 7, pp. 2228-2229, (2006).
Hartig, J.S. et al., "Protein-dependent ribozymes report molecular interactions in real time", Nature Biotechnology, vol. 20, pp. 717-722, (2002).
Herman, T. et al., "Adaptive recognition by nucleic acid aptamers", Science, vol. 287, pp. 820-825, (2000).
Kurreck, J., "Antisense technologies Improvement through novel chemical modifications", Eur. J. Biochem, vol. 270, pp. 1628-1644, (2003).
Lee, J.F. et al., "Aptamer database", Nucleic Acids Research, vol. 32, Database Issue, pp. D95-D100, (2004).
Levy, M. et al., "Quantum-dot aptamer beacons for the detection of proteins", ChemBioChem, vol. 6, pp. 2163-2166, (2005).
Liu, J. et al., "Smart nanomaterials responsive to multiple chemical stimuli with controllable cooperativity", Advanced Materials, vol. 18, pp. 1667-1671, (2006).
Liu, J. et al., "Preparation of aptamer-linked gold nanoparticle purple aggregates for colorimetric sensing of analytes", Nature Protocols, vol. 1, No. 1, pp. 246-252, (2006).
Medintz, I.L. et al., "Quantum dot bioconjugates for imaging, labeling and sensing", Nature Materials, vol. 4, pp. 435-446, (2005).
Miduturu, C. V. et al., "Modulation of DNA constraints that control macromolecular folding", Angew. Chem. Int. Ed., vol. 45, pp. 1918-1921, (2006).
Mitchell, G.P. et al., "Programmed assembly of DNA functionalized quantum dots", Journal of the American Chemical Society, vol. 121, No. 35, pp. 8122-8123, (1999).
Nutiu, R. et al., "Structure-switching signaling aptamers: Transducing molecular recognition into fluorescence signaling", Chem. Eur. J., vol. 10, pp. 1868-1876, (2004).
Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).
Rajendran, M. et al., "In vitro selection of molecular beacons", Nucleic Acids Research, vol. 31, No. 19, pp. 5700-5713, (2003).
Vet, J.A.M. et al., "Multiplex detection of four pathogenic retroviruses using molecular beacons", Proceedings of the National Academy of Science, USA., vol. 96, pp. 6394-6399, (1999).
Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).
Wilson, R. et al., "Encoded microcarriers for high-throughput multiplexed detection", Angewandte Chemie International Edition, vol. 45, pp. 6104-6117, (2006).
Winkler, W.C. et al., "Regulation of bacterial gene expression by riboswitches", The Annual Review of Microbiology, vol. 59, pp. 487-517, (2005).
Yang, C.J. et al., "Light-switching excimer probes for rapid protein monitoring in complex biological fluids", PNAS, vol. 102, No. 48, pp. 17278-17283, (2005).
Liu, J. et al., "Quantum dot encoding of aptamer-linked nanostructures for one-pot simultaneous detection of multiple analytes", Analytical Chemistry, vol. 79, No. 11, pp. 4120-4125, (2007).
Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).
Allen, M.J. et al., "Magnetic resonance contrast agents for medical and molecular imaging", Met. Ions Biol. Syst., vol. 42, pp. 1-38, (2004).
Artemov, D. et al., "MR molecular imaging of the Her-2/neu receptor in breast cancer cells using targeted iron oxide nanoparticles", Magnetic Resonance in Medicine, vol. 49, pp. 403-408, (2003).
Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).
Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).
Carr, D.H. et al., "Gadolinium-DTPA as a contrast agent in MRI: initial clinical experience in 20 patients", American Journal of Roentfenol., vol. 143, pp. 215-224, (1984).
Chen, Y. et al., "An autonomous DNA nanomotor powered by a DNA enzyme", Angew. Chem. Int. Ed., vol. 43, pp. 3554-3557, (2004).
Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).
Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).
Drolet, D.W. et al., "An enzyme-linked oligonucleotide assay", Nature Biotechnology, vol. 14, pp. 1021-1025, (1996).
Enochs, W.S. et al., "Improved delineation of human brain tumors on MR images using a long-circulating, superparamagnetic iron oxide agent", Journal of Magnetic Resonance Imaging, vol. 9, pp. 228-232, (1999).
Famulok, M. et al., "Nucleic acid aptamers-from selection in vitro to applications in vivo", Accounts of Chemical research, vol. 33, No. 9, pp. 591-599, (2000).
Fang, X. et al., "Molecular aptamer for real-time oncoprotein platelet-derived growth factor monitoring by fluorescence anisotropy", Analytical Chemistry, vol. 73, No. 23, pp. 5752-5757, (2001).
Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).
Hamaguchi, N. et al., "Aptamer beacons for the direct detection of proteins", Analytical Biochemistry, vol. 294, pp. 126-131, (2001).

(56) References Cited

OTHER PUBLICATIONS

Harisinghani, M.G. et al., "Noninvasive detection of clinically occult lymph-node metastases in prostate cancer", The New England Journal of Medicine, vol. 348, No. 25, pp. 2491-2499, (2003).
Hermann, T. et al., "Adaptive recognition by nucleic acid aptamers", Science, vol. 287, pp. 820-825, (2000).
Hoppe-Seyler, F. et al., "Peptide aptamers: Specific inhibitors of protein function", Current Molecular Medicine, vol. 4, pp. 529-538, (2004).
Huang, C-C. et al., "Aptamer-modified gold nanoparticles for colorimetric determination of platelet-derived growth factors and their receptors", Analytical Chemistry, vol. 77, No. 17, pp. 5735-5741, (2005).
Josephson, L. et al., "High-efficiency intracellular magnetic labeling with novel superparamagnetic-tat peptide conjugates", Bioconjugate Chem., vol. 10, No. 2, pp. 186-191, (1999).
Josephson, L. et al., "The effects of iron oxides on proton relaxivity", Magnetic Resonance Imaging, vol. 6, pp. 647-653, (1988).
Josephson, L. et al., "Magnetic nanosensors for the detection of oligonucleotide sequences", Angew. Chem. Int. Ed., vol. 40, No. 17, pp. 3204-3206, (2001).
Kabalka, G. et al., "Gadolinium-labeled liposomes: Targeted MR contrast agents for the liver and spleen", Radiology, vol. 163, pp. 255-258, (1987).
Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).
Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).
Lee, J. et al., "A steroid-conjugated contrast agent for magnetic resonance imaging of cell signaling", Journal of American Chemical Society, vol. 127, No. 38, pp. 13164-13166, (2005).
Lewin, M. et al., "Tat peptide-derivatized magnetic nanoparticles allow in vivo tracking and recovery of progenitor cells", Nature Biotechnology, vol. 18, pp. 410-414, (2000).
Li, J.J. et al., "Molecular aptamer beacons for real-time protein recognition", Biochemical and Biophysical Research Communications, vol. 292, No. 1, pp. 31-40, (2002).
Li, W-H. et al., "A calcium-sensitive magnetic resonance imaging contrast agent", Journal of the American Chemical Society, vol. 121, No. 6, pp. 1413-1414, (1999).
Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).
Liss, M. et al., "An aptamer-based quartz crystal protein biosensor", Analytical Chemistry, vol. 74, No. 17, pp. 4488-4495, (2002).
Liu, Y. et al., "Aptamer-directed self-assembly of protein arrays on a DNA nanostructure", Angew. Chem. Int. Ed., vol. 44, pp. 4333-4338, (2005).
Macaya, R.F. et al., "Thrombin-binding DNA aptamer forms a unimolecular quadruplex structure in solution", Proceedings of the National Academy of Science USA, vol. 90, pp. 3745-3749, (1993).
Nagel-Wolfrum, K. et al., "The interaction of specific peptide aptamers with the DNA binding domain and the dimerization domain of the transcription factor stat3-inhibits transactivation and induces apoptosis in tumor cells", Molecular Cancer Research, vol. 2, pp. 170-182, (2004).
Nitin, N. et al., "Functionalization and pepride-based delivery of magnetic nanoparticles as an intracellular MRI contrast agent", J. Biol. Inorg. Chem., vol. 9, pp. 706-712, (2004).
Nutiu, R. et al., "Engineering DNA aptamers and DNA enzymes with fluorescence-signaling properties", Pure Appl. Chem., vol. 76, Nos. 7-8, pp. 1547-1561, (2004).
Padmanabhan, K. et al., "The structure of a-thrombin inhibited by a 15-mer single-stranded DNA aptamer", The Journal of Biological Chemistry, vol. 268, No. 24, pp. 17651-17654, (1993).
Pavlov, V. et al., "Aptamer-functionalized au nanoparticles for the amplified optical detection of thrombin", The Journal of the American Chemical Society, vol. 126, No. 38, pp. 11768-11769, (2004).
Pendergrast, P.S. et al., "Nucleic acid aptamers for target validation and therapeutic applications", Journal of Biomolecular Techniques, vol. 16, issue 3, pp. 224-234, (2005).
Perez, J.M. et al., "Use of magnetic nanoparticles as nanosensors to probe for molecular interactions", ChemBioChem, vol. 5, pp. 261-264, (2004).
Perez, J.M. et al., "Viral-induced self-assembly of magnetic nanoparticles allows the detection of viral particles in biological media", Journal of the American Chemical Society, vol. 125, No. 34, pp. 10192-10193, (2003).
Radi, A-E. et al., "Reagentless, reusable, ultrasensitive electrochemical molecular beacon aptasensor", Journal of the American Chemical Society, vol. 128, No. 1, pp. 117-124, (2006).
Saeed, M. et al., "Occlusive and reperfused myocardial infarcts: differentiation with Mn-DPDP-enhanced MR imaging", Radiology, vol. 172, pp. 59-64, (1989).
Shen, T. et al., "Monocrystalline iron oxide nanocompounds (MION): Physicochemical properties", Magn. Reson. Med., vol. 29, pp. 599-604, (1993).
Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).
Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).
Soriaga, M.P. et al., "Determination of the orientation of aromatic molecules adsorbed on platinum electrodes: The effect of solute concentration", Journal of the American Chemical Society, vol. 104, pp. 3937-3945, (1982).
Sosnovik, D.E. et al., "Emerging concepts in molecular MRI", Current Opinion in Biotechnology, vol. 18, pp. 4-10, (2007).
Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).
Tasset, D.M. et al., "Oligonucleotide inhibitors of human thrombin that bind distinct epitopes", J. Mol. Biol., vol. 272, pp. 688-698, (1997).
Tian, Y. et al., "DNAzyme amplification of molecular beacon signal", Talanta, vol. 67, pp. 532-537, (2005).
Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).
Tsourkas, A. et al., "Magnetic relaxation switch immunosensors detect enantiomeric impurities", Angew. Chem. Int. Ed., vol. 43, pp. 2395-2399, (2004).
Wang, S. et al., "Core/shell quantum dots with high relaxivity and photoluminescence for multimodality imaging", Journal of the American Chemical Society, vol. 129, No. 13, pp. 3848-3856, (2007).
Weissleder, R. et al., "MR imaging of splenic metastases: Ferrite-enhanced detection in rats", American Journal Roentgenol., vol. 149, pp. 723-726, (1987).
Xiao, Y. et al., "Label-free electronic detection of thrombin in blood serum by using an aptamer-based sensor", Angew. Chem. Int. Ed., vol. 44, pp. 5456-5459, (2005).
Xiao, Y. et al., "A reagentless signal-on architecture for electronic, aptamer-based sensors via target-induced strand displacement", Journal of the American Chemical Society, vol. 127, No. 51, pp. 17990-17991, (2005).
Xu, D. et al., "Label-free electrochemical detection for aptamer-based array electrodes", Analytical Chemistry, vol. 77, No. 16, pp. 6218-6224, (2005).
Yamamoto, R. et al., "Molecular beacon aptamer fluoresces in the presence of Tat protein of HIV-1", Genes to Cells, vol. 5, pp. 389-396, (2000).

(56) References Cited

OTHER PUBLICATIONS

Zhao, M. et al., "Magnetic sensors for protease assays", Angew. Chem. Int. Ed., vol. 42, No. 12, pp. 1375-1378, (2003).
Zhao, M. et al., "Differential conjugation of tat peptide to superparamagnetic nanoparticles and its effect on cellular uptake", Bioconjugate Chem., vol. 13, pp. 840-844, (2002).
Liu, J. et al., "Colorimetric $Cu^{2+}$ detection with a ligation DNAzyme and nanoparticles", Chemical Communications, Advance Articles, DOI: 10.1039/b712421j, 6 pages, Oct. 24, 2007.
Liu, J. et al., "Non-Base pairing DNA provides a new dimension for controlling aptamer-linked nanoparticles and sensors", Journal of the American Chemical Society, vol. 129, No. 27, pp. 8634-8643, (2007).
Liu, J. et al. Supporting Information for "Colorimetric $Cu^{2+}$ detection with a ligation DNAzyme and nanoparticles", Chemical Communications, Advance Articles, 4 pages, Oct. 24, 2007.
Stratagene Catolog, "Gene Characterization Kits", 2 pages, (1988).
Fahlman, R.P. et al., "DNA conformational switches as sensitive electronic sensors of analytes", Journal of the American Chemical Society, vol. 124, 4610-4616, (2002).
Mayer, G. et al., "High-throughput-compatible assay for glmS riboswitch metabolite dependence", ChemBioChem, vol. 7, pp. 602-604, (2006).
Elowe, N., et al., "Small-molecule screening made simple for a difficult target with a signaling nucleic acid aptamer that reports on deaminase activity", Angew. Chem. Int. Ed., vol. 45, pp. 5648-5652, (2006).
Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).
Xu, D. et al., "Label-free electrochemical detection for aptamer-based array electrodes", Analytical Chemistry, vol. 77, No. 16, pp. 5107-5113, (2005).
Yigit, M et al., "MRI detection of thrombin with aptamer functionalized superparamagnetic iron oxide nanoparticles", Bioconjugate Chem., vol. 19, pp. 412-417, (2008).
"what wavelength goes with a color" from eosweb. larc. Nasa.gov. Printed on Jan. 7, 2011.
Cadmium sulfide from Wikipedia, the free encyclopedia. Printed on Jan. 7, 2011.
Yeh et al., Quantum dot-mediated biosensing assays for specific nucleic acid detection. Nanomedicine, 1, 115-121, 2005.

* cited by examiner

MRI CONTRAST AGENTS AND HIGH-THROUGHPUT SCREENING BY MRI

REFERENCE TO RELATED APPLICATIONS

This application claims the benefit of U.S. Provisional Applications Nos. 60/953,193 entitled "MRI Contrast Agents" filed Jul. 31, 2007; and 61/020,659 entitled "High-throughput Screening by MRI" filed Jan. 11, 2008, both of which are incorporated by reference in their entirety.

FEDERALLY SPONSORED RESEARCH OR DEVELOPMENT

The subject matter of this application may in part have been funded by the Department of Energy (DE-FG02-01ER63179) and the National Science Foundation (DMR-0117792, DMI-0328162 and CTS-0120978). The government may have certain rights in this invention.

BACKGROUND

Aptamers are single-stranded DNA or RNA molecules which can bind a variety of chemical and biological molecules with high affinity and selectivity. [1-4] They are isolated from a large random pool of DNA or RNA molecules using a combinatorial biology technique called systematic evolution of ligands by exponential enrichment (SELEX) [1,2]. They are often comparable to antibodies in their selective and sensitive binding to a broad range of molecules [5-8]. The major advantage of these molecules lies in the relative ease with which they can be selected for any target analyte and their stability against biodegradation and denaturation. Due to these properties aptamers are good candidates for making chemical and biological sensors in many fields such as medical diagnostics and environmental monitoring. Therefore, these aptamers have been converted into fluorescent [9-22], colorimetric [23-29] and electrochemical sensor [30-33].

For example, U.S. Publ. Pat. No. 20040175693 makes use of the discovery that the cleavage of a nucleic acid substrate by an aptazyme upon binding of an effector can be detected calorimetrically. In the presence of the effector, the substrate is cleaved and aggregated particles are dispersed, resulting in a color change. This system combines the benefit of elements that can recognize any molecule of choice with high sensitivity and ease-of-use provided by calorimetric detection.

While the above aptamer sensors have been widely explored in vitro (See, for example, U.S. Publ. Pat. No. 20030215810), their applications in vivo, particularly in humans, remain a significant challenge because of the difficulty light has in penetrating through skin and signal interference from cellular components.

Magnetic resonance imaging (MRI) is a powerful method for non-invasive three-dimensional imaging of cells and human bodies that is at the base of imaging techniques such as differential tensor imaging (DTI). One active area of research in this rapidly advancing field is development of novel MRI contrast agents, particularly smart agents that are responsive to small or biomolecular markers in cells or human bodies before cellular components or tissues display any MRI differences.

SUMMARY

In a first aspect, the invention provide an MRI contrast agent. The contrast agent comprises: (i) MRI contrast agent particles, and (ii) oligonucleotides, attached to the particles.

In a second aspect, the present invention provides a method of forming an MRI image of a sample with an MRI contrast agent. The contrast agent comprises: (i) MRI contrast agent particles, and (ii) oligonucleotides, attached to the particles. The method comprises: mixing the sample with the MRI contrast agent, and imaging the sample by MRI.

In a third aspect, the invention provides an MRI sensor system for screening a molecule against a test enzyme. The sensor system comprises: (i) MRI contrast agent particles, (ii) oligonucleotides, attached to the particles, wherein each oligonucleotide comprises an aptamer, and (iii) a test enzyme, wherein the test enzyme reacts with a corresponding substrate to form a product.

In a fourth aspect, the invention provides an MRI sensor system for screening a molecule against a test enzyme. The sensor system comprises: (i) MRI contrast agent particles, (ii) oligonucleotides, attached to the particles, (iii) bridges, hybridized to the oligonucleotides, and (iv) a test enzyme, wherein the particles, the oligonucleotides, and the bridges, together form aggregates, the bridges each comprise an aptamer that binds an effector, or the sensor system further comprises an assay enzyme and the bridges are cleaved by the assay enzyme in the presence of an effector, the test enzyme reacts with a corresponding substrate to form a product, and the corresponding substrate or the product is the effector.

In a fifth aspect, the invention provides an MRI sensor system for screening a molecule against a test enzyme. The sensor system comprises: (i) MRI contrast agent particles, (ii) oligonucleotides, attached to the particles, (iii) first and second substrates, hybridized to the oligonucleotides, (iv) an assay enzyme, and (v) a test enzyme, wherein the first and second substrates are ligated by the assay enzyme in the presence of an effector, the test enzyme reacts with a corresponding substrate to form a product, and the corresponding substrate or the product is the effector.

In a sixth aspect, the invention provides a method for screening a molecule against a test enzyme, comprising: forming a mixture comprising the molecule and an MRI sensor system that comprises: (i) MRI contrast agent particles, (ii) oligonucleotides, attached to the particles, wherein each oligonucleotide comprises an aptamer, and (iii) a test enzyme, wherein the test enzyme reacts with a corresponding substrate to form a product; and imaging the mixture by MRI.

In a seventh aspect, the invention provides a method for screening a molecule against a test enzyme, comprising: forming a mixture comprising the molecule and an MRI sensor system that comprises (i) MRI contrast agent particles, (ii) oligonucleotides, attached to the particles, (iii) bridges, hybridized to the oligonucleotides, and (iv) a test enzyme, wherein the particles, the oligonucleotides, and the bridges, together form aggregates, the bridges each comprise an aptamer that binds an effector, or the sensor system further comprises an assay enzyme and the bridges are cleaved by the assay enzyme in the presence of an effector, the test enzyme reacts with a corresponding substrate to form a product, and the corresponding substrate or the product is the effector; and imaging the mixture by MRI.

In an eighth aspect, the invention provides a method for screening a molecule against a test enzyme, comprising: forming a mixture comprising the molecule and an MRI sensor system that comprises: (i) MRI contrast agent particles, (ii) oligonucleotides, attached to the particles, (iii) first and second substrates, hybridized to the oligonucleotides, (iv) an assay enzyme, and (v) a test enzyme, wherein the first and second substrates are ligated by the assay enzyme in the presence of an effector, the test enzyme reacts with a corresponding substrate to form a product, and the corresponding substrate or the product is the effector; and imaging the mixture by MRI.

DEFINITIONS

Figure 1:
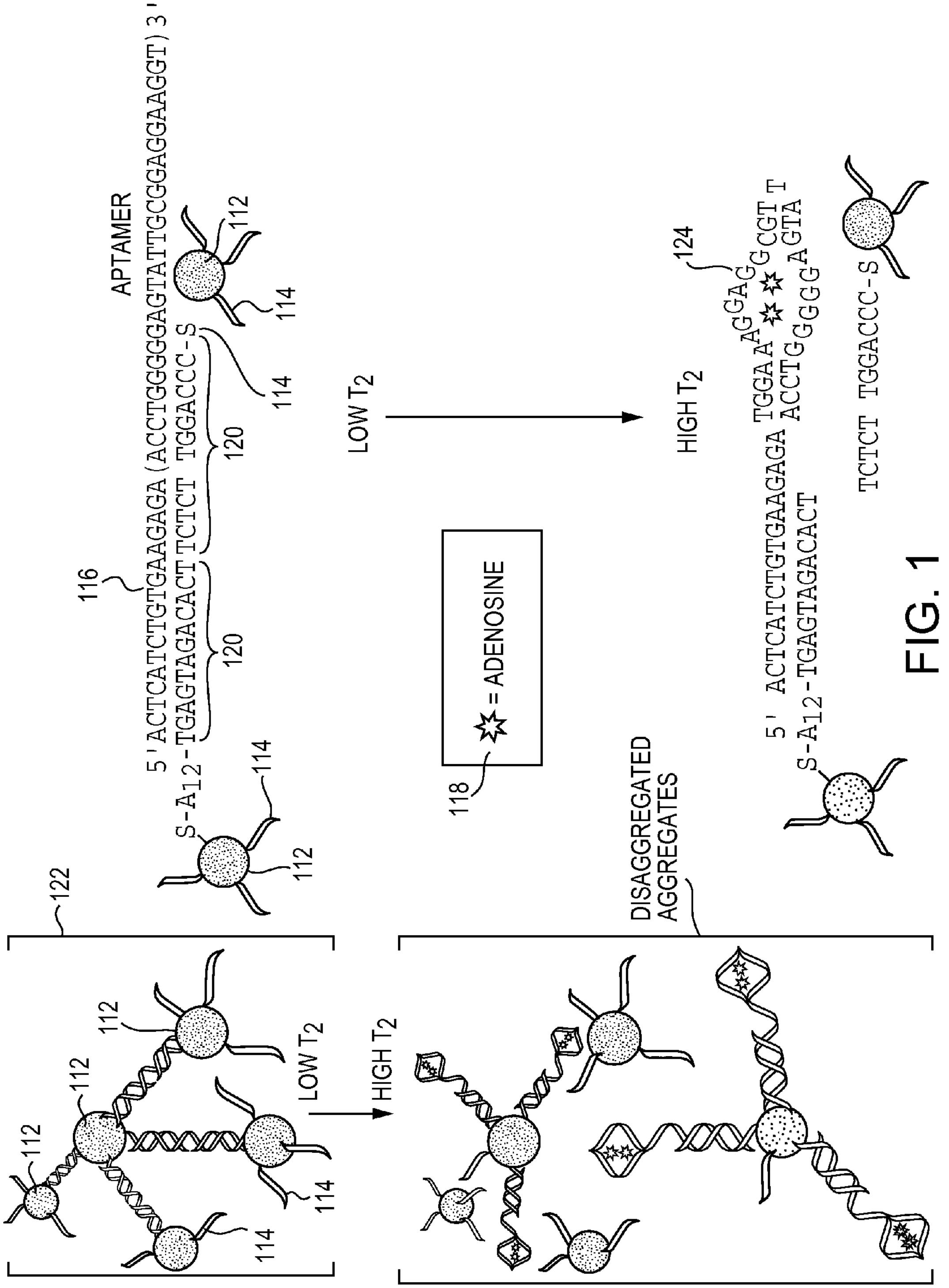
FIG. 1 illustrates an example of an aptamer system. Figure discloses SEQ ID NOS 3, 4, 3, 1 and 2, respectively, in order of appearance.

An "effector" is a molecule that, when bound to an enzyme having an effector binding site, can enhance or inhibit enzyme catalysis, or when bound to an aptamer, causes a conformational change. An "effector binding site" may be "specific," that is, binding only one effector molecule in the presence of other effector molecules. An example of effector binding site specificity is when only Zn(II) ions bind in the presence of many other ions, such as Mn(II), Mg(II) or Pb(II). Alternatively, an effector binding site may be "partially" specific (binding only a class of molecules), or "non-specific" (having molecular promiscuity). Examples of effectors include metal ions, cancer antigens, anthrax, small pox, pollutants (such as nitrogen fertilizers, toxic molecules, etc.), cocaine, human immuno-deficiency virus (HIV) and adenosine.

An "aptamer" is an oligonucleotide or peptide nucleic acid (PNA) molecule that binds a specific effector such as a molecule or ion. Aptamers are usually created by selecting them from a large random sequence pool, but natural aptamers also exist. Aptamers can be combined with nucleic acid enzymes to provide aptazymes that are active in the presence of the effector. Less preferably, a protein aptamer [98-101] may be used, for example in the multi-binding site effector system.

A "nucleic acid enzyme" is an enzyme that principally contains nucleic acids, such as ribozymes (RNAzymes), deoxyribozymes (DNAzymes), and aptazymes. PNAs are also included. A nucleic acid enzyme usually requires a metal "co-factor" for efficient substrate cleavage and/or specific effector binding. Common co-factors include Mg(II) and Pb(II). In the case of a nucleic acid enzyme that catalyzes a reaction only in the presence of an ion (such as Mg(II)), the term co-factor and effector may be used interchangeably. In the case of an aptazyme that catalyzes a reaction only in the presence of an ion (such as Mg(II)), and a second ion or molecule, the is only referred to as a co-factor, while the second ion or molecule (for which the aptamer portion of the aptazyme has a binding site) is referred to as an effector.

"Polynucleotide", "oligonucleotide" and "oligonucleic acid" are used interchangeably, and refer to a nucleic acid sequence having at least two or more nucleotides. Polynucleotides may contain naturally-occurring nucleotides, unnatural nucleotides and/or modified nucleotides. PNA molecules are also embraced by this term.

"Base-pairing" or "hybridization" refers to the ability of a polynucleotide to form at least one hydrogen bond with another polynucleotide under low stringency conditions. The hydrogen bonds form between complementary bases of the polynucleotides. When each polynucleotide contains a sequential sequence of nucleotides that can form hydrogen bonds to each other, these sequential sequences are referred to as being complementary to each other.

"MRI contrast agent" refers to an agent that increase the contrast between different parts of a sample, by altering the relaxation times during MRI. MRI contrast agents are classified by the different changes in relaxation times after their addition to a sample.

A first class of MRI contrast agents, referred to as positive contrast agents or T1 contrast agents, causes a reduction in the spin-lattice relaxation time, or T1. The class of MRI contrast agents known as negative contrast agents or T2 contrast agents cause a decrease in the spin-spin relaxation time, or T2.

DETAILED DESCRIPTION

The present invention makes use of the discovery that the formation of aggregates of MRI contrast agent particles, or the disaggregation of these aggregates, will change the T1 and/or T2 relaxation time of nearby atoms during MRI. Therefore, by causing the aggregates to form or disaggregate in specific locations within a sample or a subject, contrast in an MRI image may be enhanced. By coupling the formation or disaggregation of the aggregates, to a sensor system for detecting an effector, the MRI contrast agents of the present invention may be used to provide increased contrast in an MRI image corresponding to the location(s) of the effector in the sample.

The active contrast agents of the present invention contain at least three parts: (i) MRI contrast agent particles; (ii) oligonucleotides, attached to the particles; and (iii) bridges, which bridge together the oligonucleotides, to form aggregates of the MRI contrast agent particles, or (iii') first and second substrates, that can form bridges. Optionally, (iv) enzymes may be included. The enzymes catalyze the cleavage of the bridges, or the formation of the bridge from the first and second substrates.

There are three major systems of MRI contrast agents of the present invention:

(1) The Aptamer System: this system uses as the bridge a molecule that comprises an aptamer, specific for an effector. The oligonucleotides attached to the MRI contrast agent particles are selected so that free ends of the oligonucleotides will hybridize with the aptamer: the aptamer hybridizes with two oligonucleotides attached to different particles, thereby bridging the particles together, to form aggregates. When the aptamer binds to the effector, it undergoes a conformational change, which prevents hybridization with the oligonucleotides. This causes the aggregate of particles to disaggregate.

(2) The Enzyme System: this system uses as the bridge a substrate for an enzyme. The oligonucleotides attached to the MRI contrast agent particles are selected so that free ends of the oligonucleotides will hybridize with the substrate. Also present is an enzyme, for example a nucleic acid enzyme or aptazyme (also called allosteric nucleic acid enzymes), which will cleave the substrate when an effector is present. When the enzyme binds to the effector, it cleaves the substrate. This causes the aggregate of MRI contrast agent particles to disaggregate. This system may also be formed using a ligase as the enzyme; here the enzyme will ligate pre-bridge components (first and second substrates) to form the bridge; this will cause the aggregates to form in the presence of the effector.

(3) The Multi-Epitope Effector System: this system uses the effector as the bridge. The oligonucleotides attached to the MRI contrast agent particles are selected to each include one of at least two different aptamers for the effector, each aptamer binding to different sites, or epitopes, on the effector. When the effector is present, the oligonucleotides will attach to it, thereby bridging the particles together and forming the aggregates.

These systems combine the benefit of elements that can recognize any molecule with high sensitivity, selectivity and ease-of-use, with an MRI contrast agent, thereby providing novel contrast agents for the detection of pathologies, such as tumors in humans, animals and excised tissue samples. For example, the effector can be an antigen on the surface of cells in a tumor, such as prostate specific membrane antigen (PSMA), extracellular proteins found in tumor matrix such as tenasin-C, growth factors such as basic fibroplastic growth factor and platelet derived growth factor (PDGF), nucleic acid binding proteins such as nuclear factor kB and transcription factor E2F, and peptides such as gonadotropin-releasing hormone. Aptamers have also been developed for a variety of protein targets [68], any of which can be the effector for the MRI contrast agents.

Aptamer System

The aptamer system comprises:

(i) MRI contrast agent particles;

(ii) oligonucleotides, attached to the particles; and (iii) bridges, each comprising an aptamer for the effector.

FIG. 1 illustrates an aptamer system, featuring aptamers as the bridges. Particles 112 are attached to oligonucleotides 114, and the aptamers 116 are hybridized to the oligonucleotides 114. In the absence of the effector, for example adenosine 118, the complementary portions 120 of the oligonucleotides 114 are hybridized to the aptamer 116, thus resulting in the aggregation of the particles into aggregates 122. If the effector is present, its binds to the aptamer to form an aptamer-effector complex 124, which leads to structure switching of the aptamer, and the resulting dehybridization between the aptamer and the oligonucleotides leads to disaggregation of the aggregates. The presence of the effector thus results in disaggregation, causing the brightness change measured by MRI.

Accordingly, the presence of the effector can be detected by a change in brightness measured via MRI. Also, the concentration or the amount of the effector may be qualified by the amount of change in the brightness. For example, a low concentration of the effector will result in a small amount of cluster disaggregation, and thus a small change in brightness. On the other hand, a high concentration of the effector will result in a large amount of disaggregation and thus a large change in brightness.

The aptamer system can be used in an aptamer MRI sensor system for the high-throughput screening of enzyme inhibitors ("aptamer assaying system"). The aptamer assaying system comprises:

(i) MRI contrast agent particles;

(ii) oligonucleotides, attached to the particles;

(iii) bridges, comprising an aptamer;

(iv) test enzyme; and (v) a corresponding substrate for the test enzyme.

Figure 14:
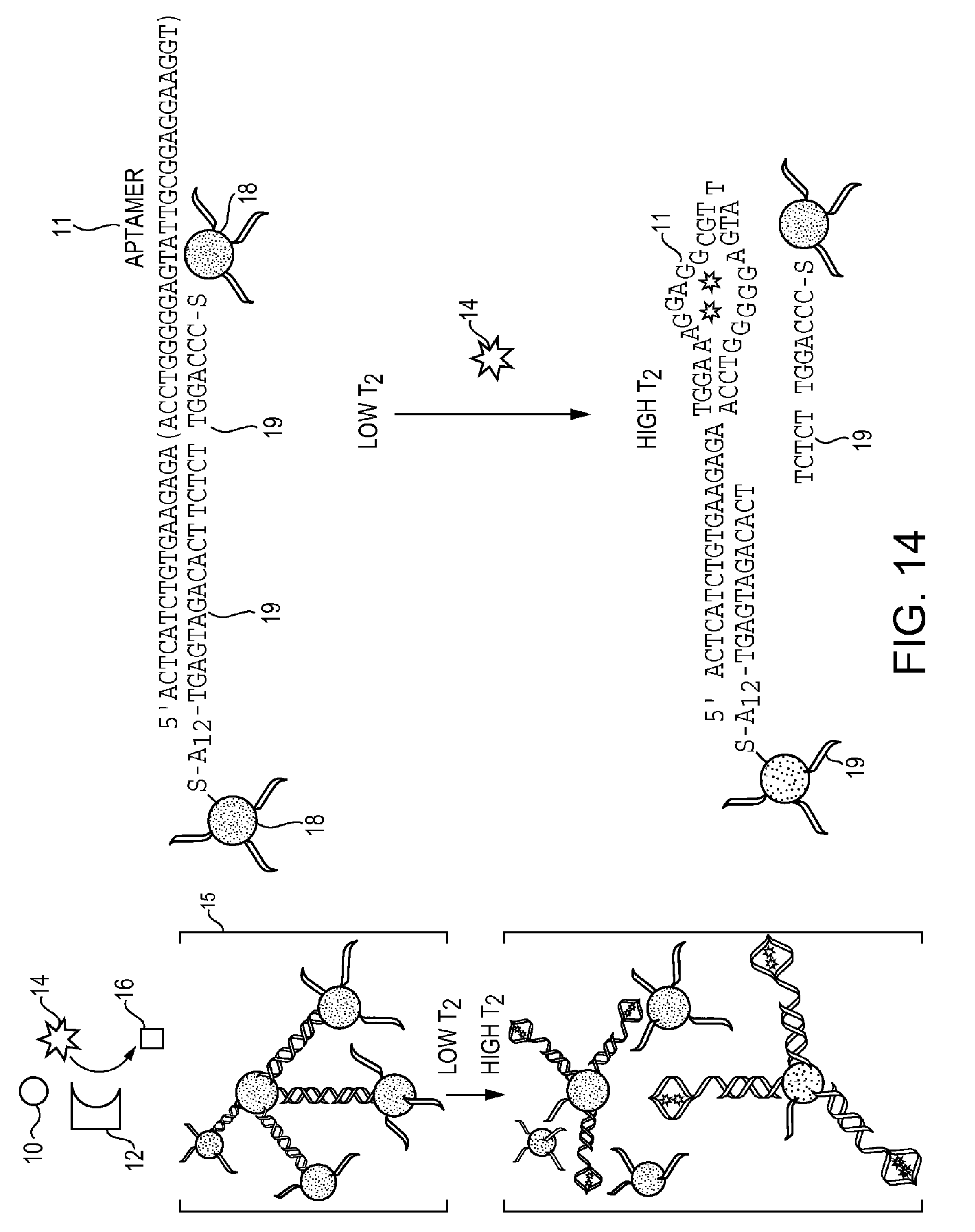
FIG. 14 illustrates the screening of molecules with an aptamer system. Figure discloses SEQ ID NOS 3, 4, 3, 1 and 2, respectively, in order of appearance.

FIG. 14 illustrates the screening of enzyme inhibitors by means of an aptamer assaying system. Molecule 10 is screened as an inhibitor of test enzyme 12, which catalyzes the conversion of substrate 14 to product 16. Whereas substrate 14 binds to aptamer 11, product 16 does not.

Particles 18 are attached to oligonucleotides 19, and the aptamer 11 is present in the mixture. If the molecule 10 is not effective in inhibiting test enzyme 12, substrate 14 is transformed into product 16, and the complementary portions of the oligonucleotides 19 are hybridized to the aptamer, thus resulting in the aggregation of the particles into aggregate 15. If the molecule is effective as inhibitor of the test enzyme, then substrate 14 remains present and binds to the aptamer 11, thereby inducing structure switching of the aptamer. The resulting dehybridization leads to the deaggregation of the clusters.

Alternatively, aptamer 11 may be chosen so that it binds to product 16 and not to substrate 14. In this case, a molecule effective in inhibiting test enzyme 12 will lead to the formation of aggregates, and vice versa.

If the MRI contrast agent particles are T2 contrast agents, the aggregated state changes the magnetic relaxivity of nearby atoms, for instance protons in the vicinity. Conversely, the deaggregation of the clusters leads to an increase in the T2 relaxation time, which can be imaged as an increase in brightness via MRI. In addition, the deaggregation of the clusters can be used to produce an increase in T1 relaxation time which may also be imaged via MRI.

Accordingly, the efficacy of the molecule as an inhibitor can be detected by an increased brightness measured via MRI.

Enzyme System

The enzyme system comprises:

(i) MRI contrast agent particles;

(ii) oligonucleotides, attached to the particles;

(iii) bridges, each comprising a substrate for an enzyme, or (iii) first and second substrates for the enzyme that will form bridges; and (iv) enzymes, the enzymes responsive to an effector.

The enzyme cleaves the bridges when the effector is present, or forms the bridges from the first and second substrates, when the effector is present. Example enzymes include nucleic acid enzymes, aptazymes and protein enzymes.

Figure 2:
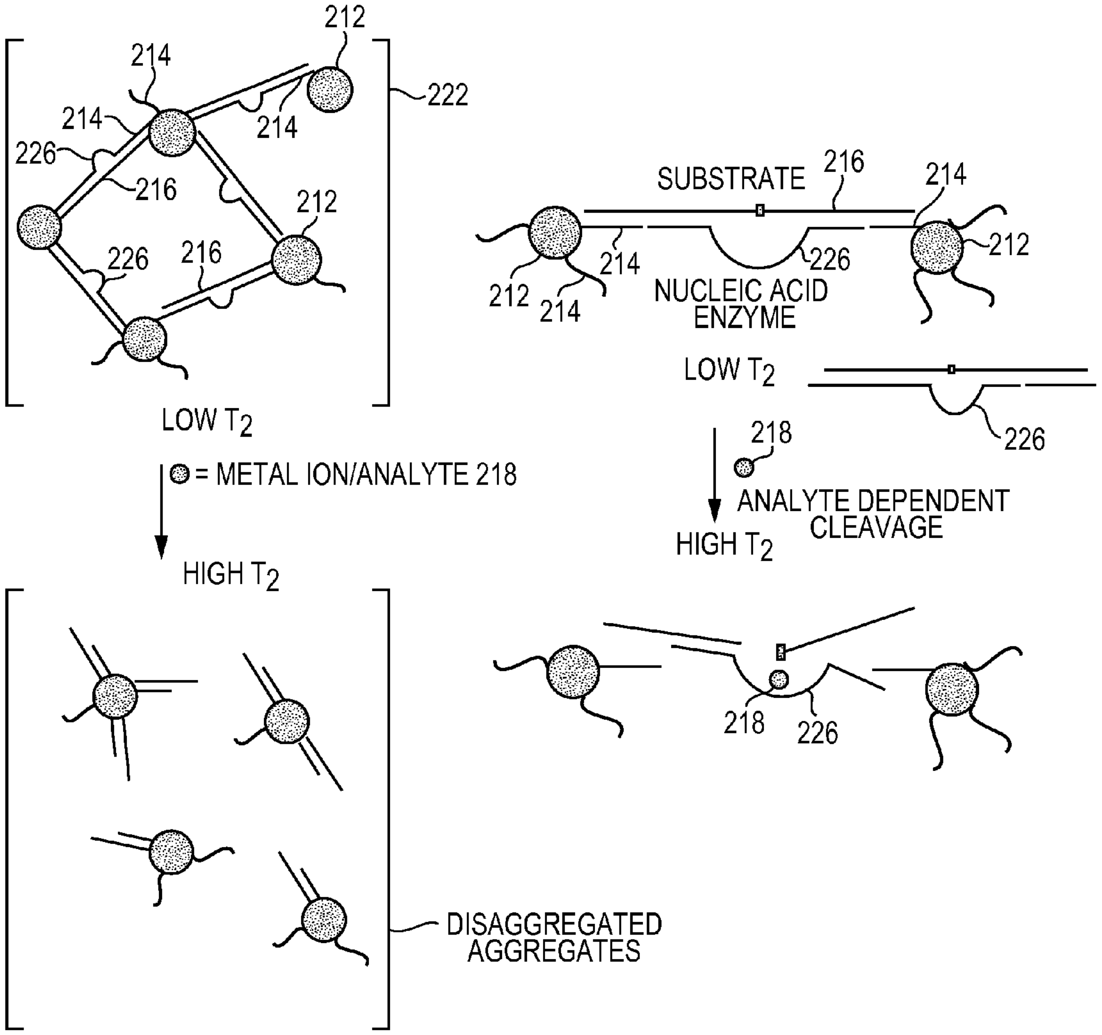
FIG. 2 illustrates an example of a nucleic acid enzyme system.

FIG. 2 illustrates an enzyme system featuring a nucleic acid enzyme as the enzymes, and the bridges are substrates for the enzymes. The oligonucleotides 214, attached to the particles 212, are hybridized to the bridges (substrates) 216. The nucleic acid enzymes 226 are also hybridized to the bridges 216. The particles, the oligonucleotides, the bridges and the enzymes form aggregates 222. If the effector 218 is absent, the nucleic acid enzymes are either inactive or show substantially reduced activity, resulting in little or no substrate cleavage, and thus the particles remain aggregated. If the effector is present, the enzymes are actived, and cleave the bridges, causing disaggregation of the aggregates because the link between the particles is broken. The presence of the effector thus results in disaggregation, causing the brightness change measured by MRI.

Figure 3:
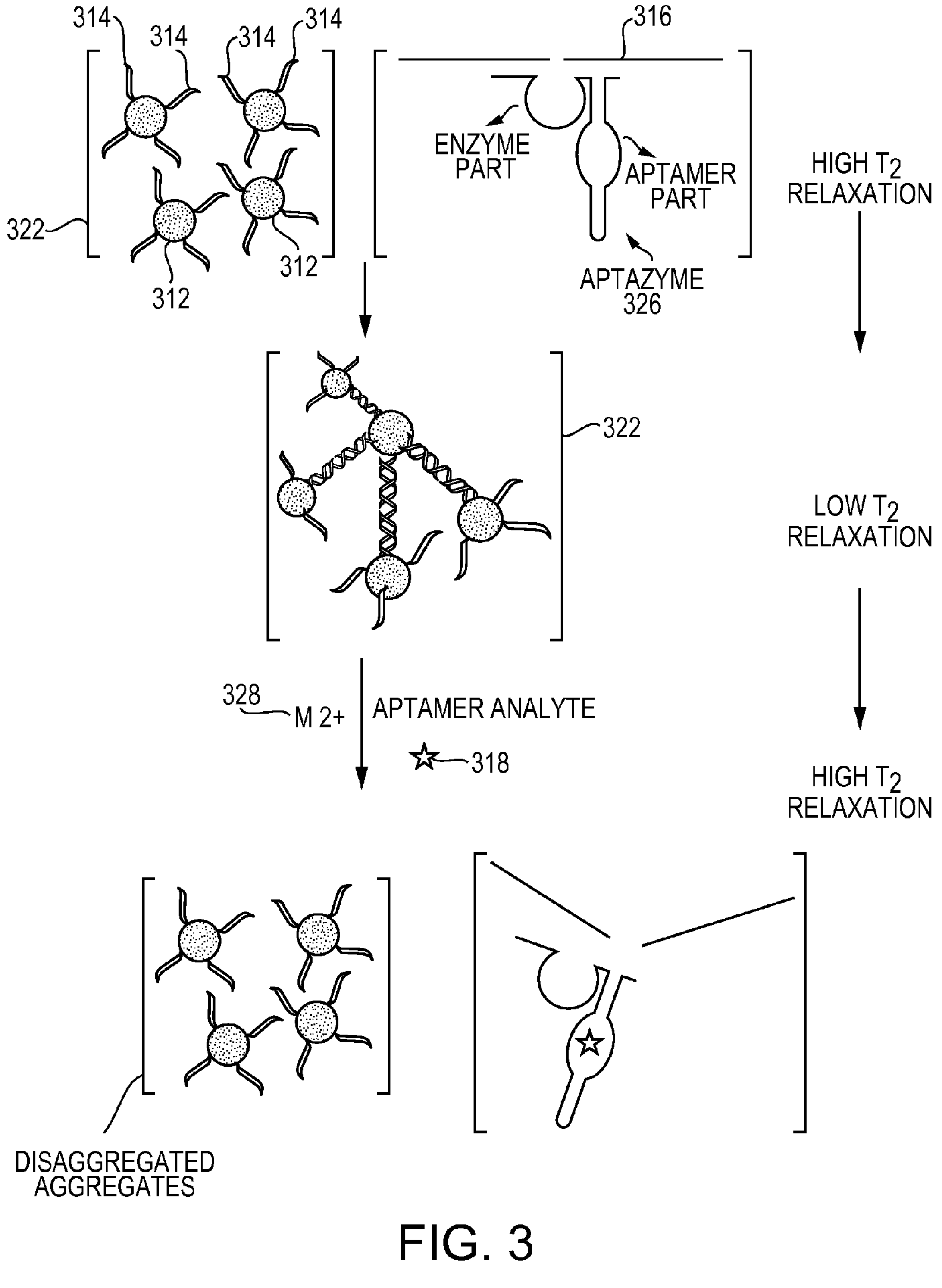
FIG. 3 illustrates an example of an aptazyme system.

FIG. 3 illustrates an enzyme system featuring an aptazyme as the enzymes, and the bridges are substrates for the enzymes. The oligonucleotides 314, attached to the particles 312, are hybridized to the bridges (substrates) 316. The aptazymes 326 are also hybridized to the bridges 316. The particles, the oligonucleotides, the bridges and the aptazymes form aggregates 322. If the effector 318 is absent (and/or any necessary co-factor 328), the aptazymes are either inactive or show substantially reduced activity, resulting in little or little substrate cleavage, and thus the particles remain aggregated. If the effector is present (and any necessary co-factor), the enzymes are active and cleave the bridges, causing disaggregation of the aggregates because the link between the particles is broken. Accordingly, the presence of the effector causes a change in brightness measured by MRI.

The enzyme system can be used in an assaying enzyme MRI sensor system for the high-throughput screening of enzyme inhibitors ("assaying enzyme system"). The assaying enzyme system comprises:

(i) MRI contrast agent particles;

(ii) oligonucleotides, attached to the particles;

(iii) bridges, comprising a substrate for an assaying enzyme, or substrates for an assaying enzyme that will form bridges;

(iv) assaying enzyme, the enzyme having an effector binding site.

(v) test enzyme; and (vi) a corresponding substrate for the test enzyme.

The assaying enzyme cleaves the bridges when the effector is present, or forms the bridges from substrates when the effector is present. Examples of assaying enzymes include nucleic acid enzymes, aptazymes and protein enzymes.

Figure 15:
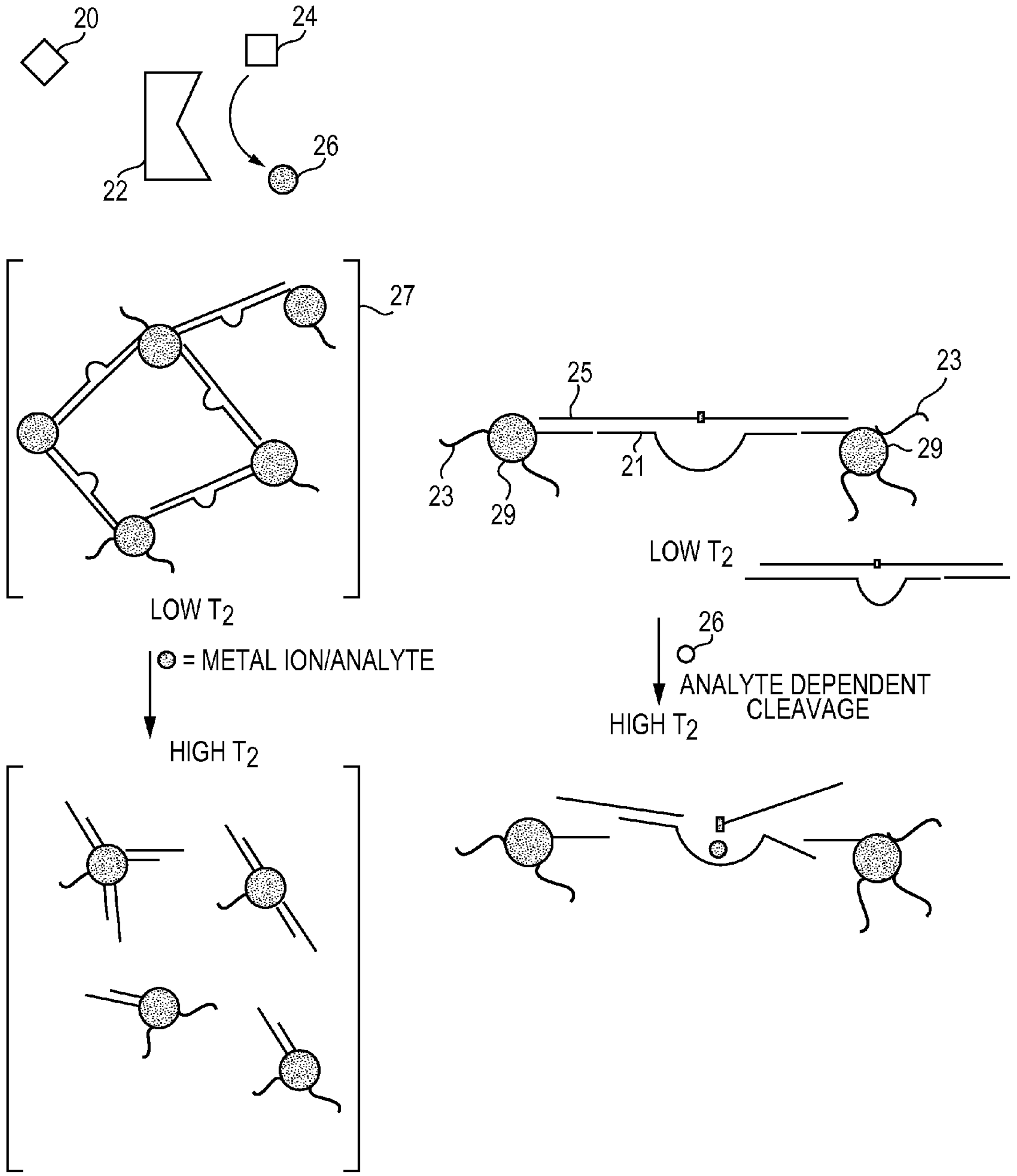
FIG. 15 illustrates the screening of molecules with an assaying enzyme system.

FIG. 15 illustrates the screening of inhibitors of a test enzyme by means of an assaying enzyme system. Molecule 20 is screened as an inhibitor of test enzyme 22, which catalyzes the conversion of substrate 24 to product 26. Product 26 is an effector of the assaying enzyme, whereas substrate 24 is not.

The complementary portions of polynucleotides 23 (the polynucleotides attached to the particles 29) are hybridized to bridge 25 in the presence of a sample containing molecule 20, substrate 24, and enzyme 22. The assaying enzyme 21 is also hybridized to the bridge 25. The particles, the bridges, the substrates and the assaying enzymes thereby form aggregate 27.

If molecule 20 is active as an inhibitor of the test enzyme 22, substrate 24 is not converted into product 26. As product 26 is absent, the assaying enzyme is either inactive or shows substantially reduced activity, resulting in little or no substrate cleavage, and thus the particles remain aggregated. If molecule 20 is inactive as an inhibitor of test enzyme 22, product 26 is formed. Consequently, the assaying enzyme 21 is activated and cleaves the bridge 25, causing deaggregation of the aggregate 27 because the link between the particles is broken by the cleavage of the bridge. The inactivity of molecule 20 thus results in deaggregation, causing the brightness change measured by MRI.

Alternatively, assaying enzyme 21 may be chosen so that substrate 24 is an effector of the assaying enzyme, whereas product 26 is not. In this case, a molecule effective in inhibiting test enzyme 20 will lead to the formation of aggregates.

Figure 16:
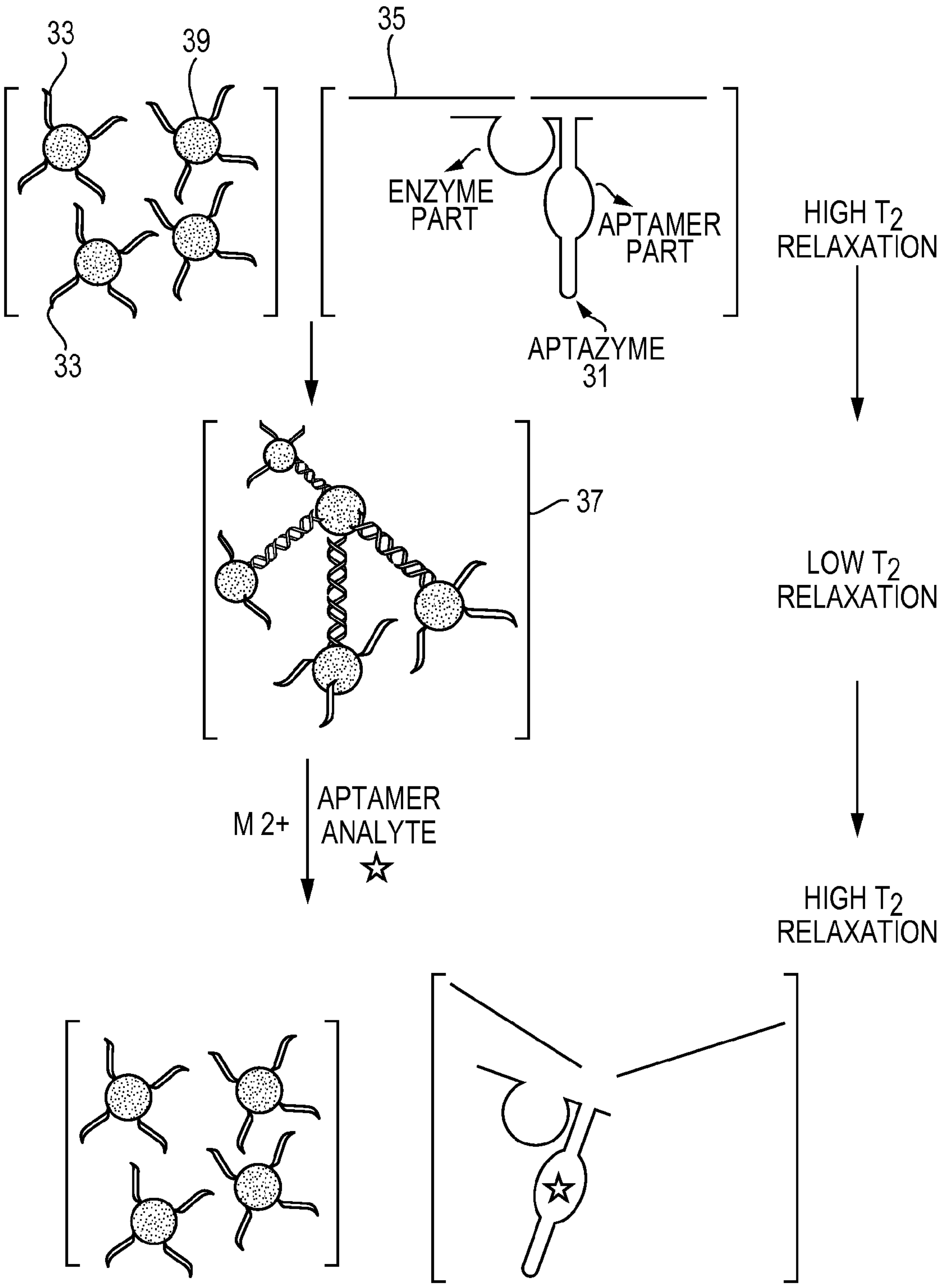
FIG. 16 illustrates the screening of molecules with an assaying enzyme system, where the assaying enzyme is an aptazyme.

FIG. 16 illustrates the screening of inhibitors of a test enzyme by means of the assaying enzyme system, where the assaying enzyme is an aptazyme and an oligonucleotide is the bridge. Molecule 30 is screened as an inhibitor of test enzyme 32, which catalyzes the conversion of substrate 34 to product 36. Product 36 is an effector of the assaying enzyme, whereas substrate 34 is not.

The complementary portions of the polynucleotide 33 (the polynucleotides attached to the particles 39) are hybridized to bridge 35 in the presence of a sample containing molecule 30, test enzyme 32 and the bridge. The assaying aptazyme 31 is also hybridized to the bridge 35. The particles, the bridges, the substrates and the enzymes thus form aggregate 37.

If molecule 30 is active as an inhibitor of the test enzyme 32, substrate 34 is not converted into product 36. In the absence of 36, the assaying aptazyme is either inactive or shows substantially reduced activity, resulting in little or no substrate cleavage, and thus the particles remain aggregated. If molecule 30 is inactive as an inhibitor of test enzyme 32, product 36 is formed. Consequently, the assaying aptazyme 31 is active and cleaves the bridge 35, causing deaggregation of the aggregate 37 because the link between the particles is broken by the cleavage of the bridge. The inactivity of molecule 30 thus results in deaggregation, causing a change in MRI brightness.

Alternatively, assaying aptazyme 31 may be chosen so that substrate 34 is an effector of the assaying enzyme, whereas product 36 is not. In this case, a molecule effective in inhibiting test enzyme 30 will lead to the formation of aggregates.

Accordingly, the presence of the effector causes an increased brightness as measured by MRI. By including an aptamer recognizing a desired effector, MRI contrast agents for any desired effector can be easily made and used.

Multi-Epitope Effector System

The multi-epitope effector system comprises:

(i) MRI contrast agent particles;

(ii) oligonucleotides, attached to the particles, each oligonucleotide comprising one of at least two aptamers, wherein each of the at least two aptamers binds an effector at different binding sites.

Figure 9:
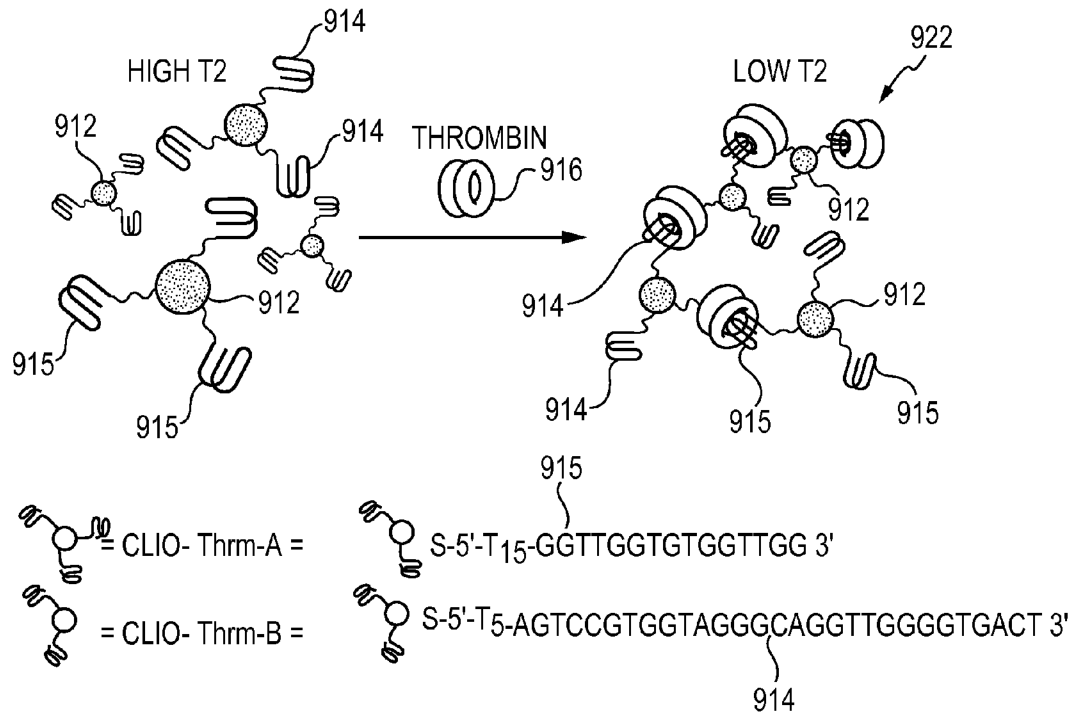
FIG. 9 illustrates a multi-epitope effector system for the detection of thrombin. Figure discloses SEQ ID NOS 5-6, respectively, in order of appearance.

FIG. 9 illustrates a multi-epitope effector system, featuring thrombin as the effector (which acts as the bridge), and CLIO-Thrm-A and CLIO-Thrm-B, two different aptamers of thrombin, as the oligonucleotides. The oligonucleotides, which are two different aptamers 914 and 915, are attached to the particles 912. If the effector 916 is absent, the particles and the oligonucleotides remain disaggregated. If the effector is present, it acts as a bridge, and the aptamers each attached to different sites (epitopes) of the effector, causing aggregation to form aggregates 922. Accordingly, the presence of the effector causes a change in brightness measured by MRI.

The particles are attached to one of at least two aptamers. Each particle may be linked to each of the aptamers, resulting in one type of particle. Alternatively, a first subset of the particles is attached to first aptamers, and a second subset of the particles is attached to second aptamers, etc., resulting in more than one types of particle. Finally, a mixture of the two systems, as well as a random distribution between the two systems may also be used.

The multi-epitope effector system can be used in a multi-epitope MRI sensor system for the high-throughput screening of enzyme inhibitors ("multi-epitope effector assaying system"). The multi-epitope effector assaying system comprises:

(i) MRI contrast agent particles;

(ii) oligonucleotides, attached to the particles, wherein the oligonucleotides comprise a first aptamer that binds to a first binding site on an effector;

(iii) a second aptamer linked to at least one of the particles, wherein the second aptamer binds to a second binding site on the effector;

(iv) test enzyme; and (v) a corresponding substrate for the test enzyme.

The particles are linked to the first aptamer and the second aptamer. Alternatively, a first subset of the particles is attached to the first aptamer, and a second subset of the particles is attached to the second aptamer.

Figure 17:
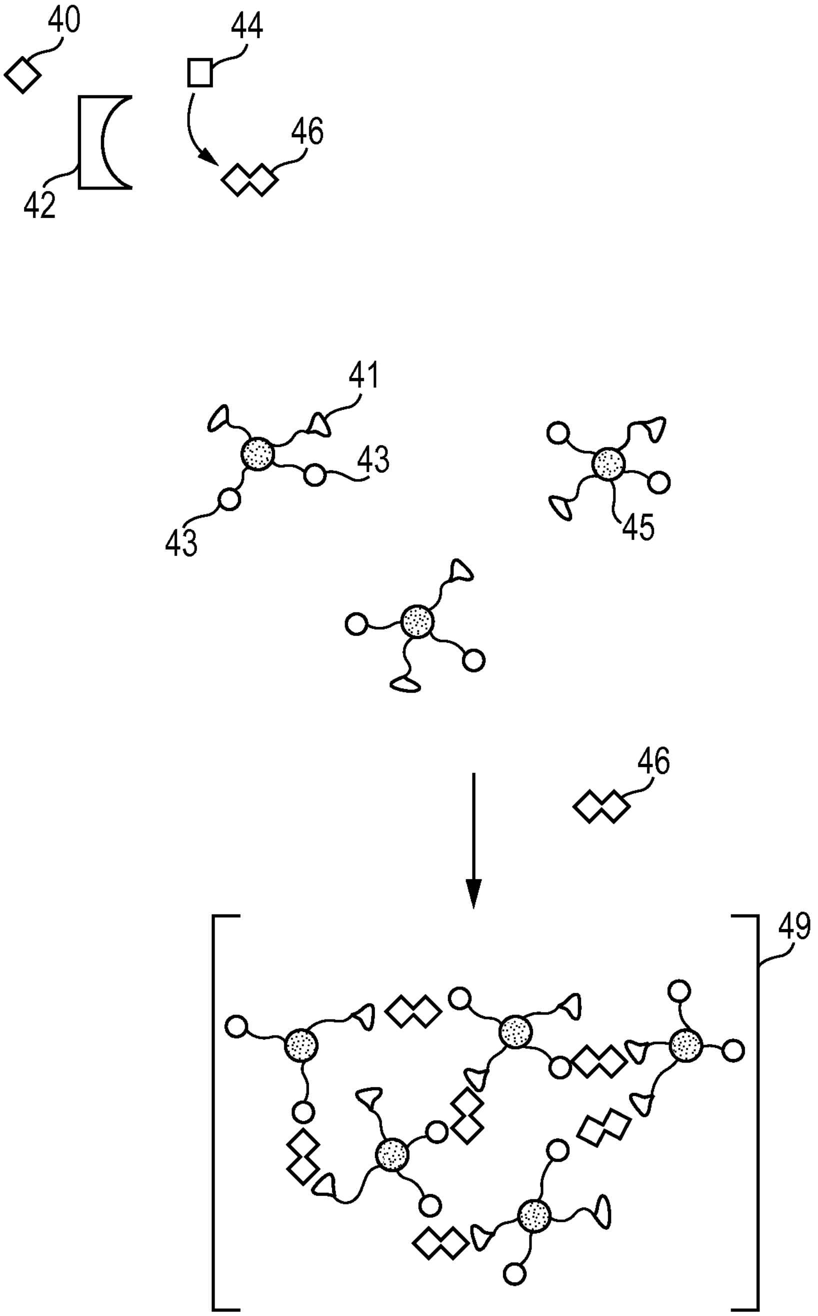
FIG. 17 illustrates the screening of molecules with a multi-epitope effector system.

FIG. 17 illustrates the screening of inhibitors of a test enzyme by means of the multi-epitope effector assaying system. Molecule 40 is screened as an inhibitor of test enzyme 42, which catalyzes the conversion of substrate 44 to product 46. Product 46 is an effector of the first aptamer 41 and second aptamer 43, whereas substrate 44 is not.

If molecule 40 is an effective inhibitor of test enzyme 42, no product 46 is formed and the particles 45 are dispersed in solution. If molecule 40 is not an inhibitor of the enzyme, product 46 is formed and the aptamers bind thereto, leading to the aggregation of the particles to form aggregate 49. This will lead to a corresponding change in MRI brightness.

Alternatively, the first aptamer and the second aptamer may be chosen so that substrate 44 is an effector of the assaying enzyme, whereas product 46 is not. In this case, a molecule effective in inhibiting test enzyme 42 will lead to the formation of aggregates.

In vitro selection of aptamers, nucleic acid enzymes and aptazymes

Aptamers and aptazymes that bind a desired effector can be isolated by in vitro selection. In vitro selection is a technique in which RNA or DNA molecules with certain functions are isolated from a large number of sequence variants through multiple cycles of selection and amplification [42, 43]. DNAzymes and RNAzymes with maximized activities or novel catalytic abilities, as well as aptamers, can be obtained using, for example, the technique of systematic evolution of ligands by exponential enrichment (SELEX) [44].

In vitro selection is typically initiated with a large collection (pool) of randomized sequences, usually containing $10^{13}$-$10^{15}$ sequence variants. Chemical synthesis of a set of degenerated polynucleotides using standard phosphoramidite chemistry can be used to generate such randomized pools. The 3'-phosphoramidite compounds of the four nucleosides (adenosine, cytosine, guanine, thymidine) are premixed and used to synthesize the polynucleotides; randomness is generated by controlling the ratio of the four phosphoroamidites. Biases can also be achieved, as well as holding a phosphoramidite constant at a specific position. Other strategies for creating randomized DNA libraries include mutagenic polymerase chain reaction (PCR) and template-directed mutagenesis [45, 46, 47]. If in vitro selection of RNA molecules is desired, randomized DNA libraries are first converted to an RNA library by in vitro transcription.

The randomized libraries are then screened for molecules possessing a desired function, such as binding an effector, and are isolated. Separation may be achieved using affinity column chromatography (using, for example, the effector), gel electrophoresis, or selective amplification of a tagged reaction intermediate. The selected molecules are amplified, using, for example, PCR for DNA, or isothermal amplification reaction for RNA. These selected, amplified molecules are then mutated (reintroducing diversity) using, for example, mutagenic PCR to attempt to select for molecules with yet higher activity. These three steps, selection, amplification and mutation, are repeated, often with increasing selection stringency, until sequences with the desired activity dominate the pool.

Novel nucleic acid enzymes isolated from random sequences in vitro have extended the catalytic repertoire of RNA and DNA. Deoxyribozymes catalyze fewer types of reactions compared to ribozymes. The catalytic rate ($k_{cat}$) of most deoxyribozymes is comparable to that of ribozymes catalyzing the same reaction. In certain cases, the catalytic efficiency ($k_{cat}/K_m$) of nucleic acid enzymes even exceeds protein enzyme catalytic efficiency.

In vitro selection can be used to change the ion specificity or binding affinity of existing nucleic acid enzymes, or to obtain nucleic acid enzymes specific for desired substrates. For example, the $Mg^{2+}$ concentration required for optimal hammerhead ribozyme activity has been lowered using in vitro selection to improve the enzyme performance under physiological conditions [48, 49].

Often nucleic acid enzymes developed for a specific effector by in vitro selection will have activity in the presence of other molecules. For example, 17E deoxyribozyme was developed by in vitro selection for activity in the presence of $Zn^{2+}$. However, the enzyme showed greater activity in the presence of $Pb^{2+}$ than $Zn^{2+}$. Although produced in a process looking for $Zn^{2+}$-related activity, 17E may be used as a sensitive and selective sensor for $Pb^{2+}$. To produce nucleic acid enzymes with greater selectivity, a negative selection step may be introduced.

Other polynucleotide sequences are useful, including those described in U.S. Pat. No. 6,706,474 [50]. Representative aptazymes and methods for making aptazymes and attaching them to particles are described, for example, in U.S. Publ. Pat. No. 20040175693 [63].

MRI Contrast Agent Particles

Acceptable MRI contrast agent particles comprise paramagnetic materials, such as solid compounds of gadolinium, manganese or iron, or any other paramagnetic material. Examples include superparamagnetic iron oxide (SPIO) and ultrasmall superparamagnetic iron oxide (USPIO), gadonanotubes (a gadolinium contrast agent trapped within a $C_{60}$ or carbon nanotubes), Quantum dots coated or doped with a paramagnetic material [67], or silicates, phosphates, and carbonates of gadolinium, manganese or iron, as well as their complex oxides, or any other silicate, phosphate and carbonate that may be doped with gadolinium, manganese or iron. Furthermore, any existing MRI contrast agent based on paramagnetic compounds may be attached to the surface of a particle, such as alumina or silica, thereby transforming the particle in an MRI contrast agent particle.

In the case where the MRI contrast agent particles are T2 contrast agents, the aggregated state changes the magnetic relaxivity of nearby atoms, for instance protons in the vicinity. Conversely, the disaggregation of aggregates leads to an increase in the T2 relaxation time, which can be imaged as an increase in brightness by MRI. In addition, the disaggregation of the clusters can be used to produce an increase in T1 relaxation time which may also be imaged by MRI.

In order to attach polynucleotides to the particles, the particles, polynucleotides or both are first derivatized. For instance, if the particles are covered with a thin layer of gold, such as by sputtering, polynucleotides derivatized with alkanethiols at their 3'- or 5'-termini readily attach to gold surfaces [51]. A method of attaching 3' thiol DNA to gold surfaces can also be used to attach polynucleotides to the particles [52]. Alkanethiol-derivatized particles can be used to attach polynucleotides. Other functional groups for attaching polynucleotides to solid surfaces include phosphorothioates to attach polynucleotides to gold surfaces [53], as well as substituted alkylsiloxanes, aminoalkylsiloxanes and mercaptoaklylsiloxanes, for binding polynucleotides to oxides such as ceramics, or metals that form an oxide surface coat in air [54]. Polynucleotides terminating in a 5'-thionucleoside or a 3'-thionucleoside may also be used for attaching polynucleotides to solid surfaces. Some methods of attaching polynucleotides are presented in Table 1.

TABLE 1

Systems for attaching polynucleotides to particles

| System | Reference |
| --- | --- |
| biotin-streptavidin | [55] |
| Carboxylic acids on aluminum | [56] |
| disulfides on gold | [57] |
| Carboxylic acids on oxides | [58, 59] |
| Carboxylic acids on platinum | [60] |
| aromatic ring compounds on platinum | [61] |
| silanes on oxides | [62] |

Substrates for aptazymes and nucleic acid enzymes

The substrates for the aptazymes and the nucleic acid enzymes comprises three portions. The first and second portions of the substrate are separated by the third portion that is cleaved by the enzyme in the presence of the effector. When the substrate is a polynucleotide, it is usually modified by extension of the 3'- and 5'-ends by a number of bases which act as "sticky ends" for facilitating hybridization to complementary portions of oligonucleotides attached to the particles. Substrate modification allows complexes comprising substrate-linked particles to be formed without inhibiting the enzyme/substrate interaction. However, where the substrate contains regions not critical for interaction with the nucleic acid enzyme or aptazyme, modification may not be necessary.

Kits

The invention also provides kits for producing an MRI contrast agent, or for producing an MRI image. The kit may comprise, in separate containers, each of the components of the MRI contrast agent. For example, the aptamer system could be supplied in a kit, with the MRI contrast agent particles, with the attached oligonucleotides, in a first container, and the bridges in a second container; optionally, a third container could contain solvent (such as sterile water). For the enzyme system supplied as a kit, for example, the MRI contrast agent particles, with the attached oligonucleotides, may be supplied in a first container, the bridges in a second container (or the first and second substrates supplied in one or two containers), and the enzymes supplied in a last container. For the multi-epitope effector system, for example, the MRI contrast agent particles, with the attached oligonucleotides, may be supplied in a first container, with a second container containing solvent (such as sterile water).

The MRI contrast agent may be ready to administer, being supplied in a unit dosage form, and in a form ready for administer, with or without a pharmaceutically acceptable carrier. For example, the MRI contrast agent may be supplied in a pre-measured syringe, in sterile form, already mixed with a pharmaceutically acceptable carrier, such as a saline solution. When a kit is supplied, the different components of the composition may be packaged in separate containers and admixed immediately before use. Such packaging of the components separately may permit long-term storage of the active components.

The reagents included in the kits can be supplied in containers of any sort such that the life of the different components are preserved and are not adsorbed or altered by the materials of the container. For example, sealed glass ampules may contain one of more of the reagents, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

The kits may also contain other reagents and items. The reagents may include standard solutions containing known quantities of the effector, dilution and other buffers, pretreatment reagents, etc. Other items which may be provided as part of the kit include syringes, pipettes and containers.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

The present invention is similar to sensor systems for detection of an analyte, which use the aggregation of disaggregation of particles to cause a color change, such as those described in WO2005/100602, and U.S. Publ. Pat. Nos. 20030215810, 20040175693, 20060166222 and 20070037171. The systems described in these references may be used as MRI contrast agents, if the particles used for color change are replaced with MRI contrast agent particles.

An aptazyme designed for the directed assembly of gold particles for calorimetric detection and quantification of adenosine may be used as a starting point, by replacing the gold particles with MRI contrast agent particles. By replacing the aptamer domain that recognizes adenosine in the exemplary adenosine biosensor with other aptamer domains recognizing pre-selected effectors, colorimetric sensors for any desired effector can be easily made and used. Furthermore, by replacing the catalytic core (the 8-17 motif in this case) with other catalytic cores, similar aptazymes may be engineered.

Example 1

Figure 4:
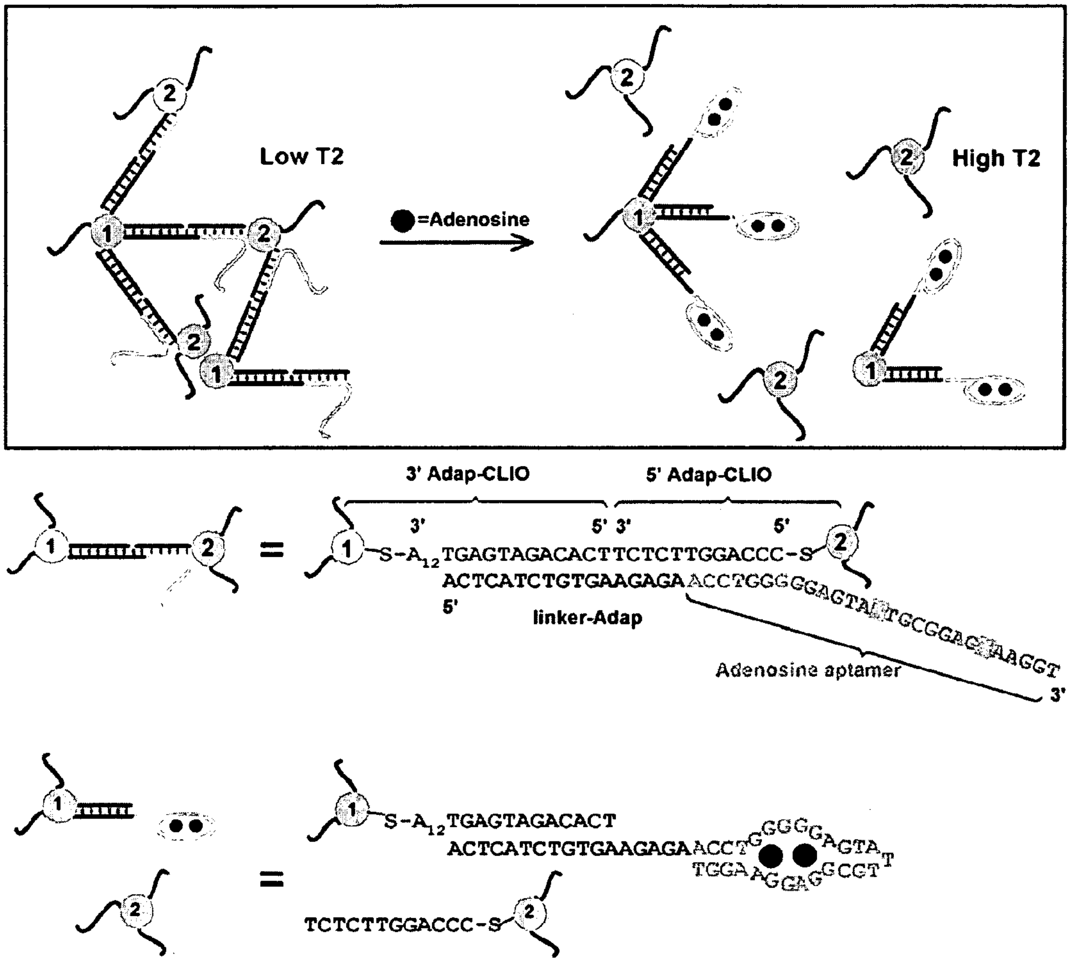
FIG. 4 illustrates an aptamer system for the detection of adenosine. Figure discloses SEQ ID NOS 4, 3, 1, 3 and 2, respectively, in order of appearance.

SPIO nanoparticles were chosen as the contrast agents to functionalize by aptamers since it is efficient at dephasing the spins of neighboring water protons, leading to change in T2 [36, 37]. It has also been shown that oligonucleotide functionalized cross-linked dextran coated superparamagnetic iron oxide nanoparticles (CLIOs) form clusters when linked with a complementary sequence [38]. The CLIOs were combined with an adenosine aptamer as shown in FIG. 4. The adenosine sensor comprised CLIO aggregates that are prepared using three components: CLIO functionalized with 3'- or 5'-thiol modified DNA, called 3'Adap-CLIO and 5'Adap-CLIO respectively and a linker DNA, called linker-Adap that can hybridize to both the 3'- and 5'Adap-CLIOs, leading to the formation of clusters.

One segment of the linker is the sequence for the adenosine aptamer. Seven bases of this aptamer are involved in the hybridization with the 5'Adap-CLIO. In the presence of adenosine the aptamer undergoes structure switching in order to form the adenosine binding pocket [17, 29, 39, 40], which results in disruption of base pairing interactions with 5'Adap-CLIO. The five remaining base pairs between the linker-Adap and the 5'Adap-CLIO are not enough to hold them together at room temperature leading to disassembly of clusters. The dispersed nanoparticles result in a higher T2 as compared to the clusters; and thus the adenosine induced disassembly can be monitored as an increase in T2 values and enhancement in brightness of T2 weighted MRI images.

A mutated, non-adenosine binding mutated linker was also prepared. The two nucleobases highlighted in grey in the adenosine aptamer segment of linker-Adap are the points of mutation (T→A, G→C) in the mutated linker sequence.

Figure 5:
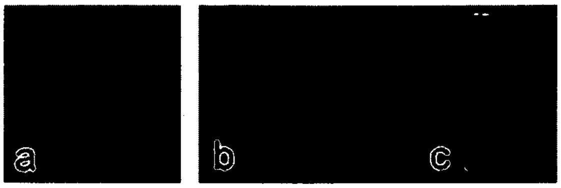
FIG. 5 illustrates the aptamer system of FIG. 4 in the presence of the linker (FIG. 5C), with no linker (FIG. 5A), and in the presence of a non-complementary sequence linker (FIG. 5B).

CLIO was synthesized according to literature procedures and functionalized with N-Succinimidyl 3-(2-pyridyldithio)-propionate (SPDP) which could be readily coupled to thiol modified DNA (3'Adap or 5'Adap) [38, 41]. Equimolar mixture of 3'Adap-CLIO and 5'Adap-CLIO (both at 100 μg Fe $ml^{-1}$) were incubated with the linker-Adap which lead to the formation of big clusters of nanoparticles that precipitate out of solution (FIG. 5C). The same effect was not observed when no linker (FIG. 5A) or a non-complementary sequence was used (FIG. 5B).

Figure 6:
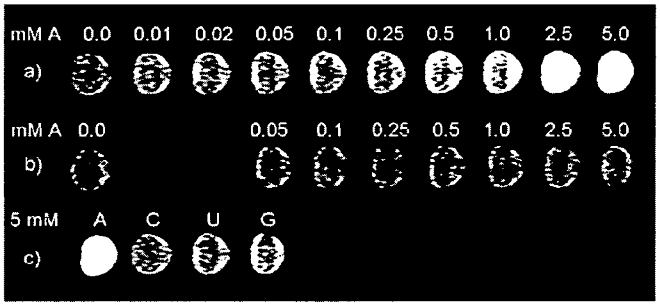
FIG. 6 illustrates the MRI brightness of the aptamer system of FIG. 4 in the presence of adenosine and controls.

In order to measure T2, lower concentrations of CLIO-DNA conjugates (~20 μg Fe $ml^{-1}$) were mixed with linker-Adap so that the sensor clusters do not precipitate out of solution. The prepared sensor was then aliquoted into the wells of a microplate, with progressively increasing amount of adenosine and a T2 weighted MRI image was obtained. An increase in adenosine concentration led to an increase in the brightness of the image, as illustrated in line a) of FIG. 6. This increase was attributed to the increase in T2 due to disassembly of CLIO clusters into smaller particles. It is worth noting that even at 10 μM adenosine a detectable change in contrast was observed.

To ensure that the observed effect is solely due to specific binding of adenosine by the aptamer rather than other non-specific effects, the above non-adenosine binding mutated linker was used as a control. This mutated linker has been shown not to bind adenosine[17, 29] As was expected, no change in brightness was observed with increasing adenosine concentration, as illustrated in line b) of FIG. 6. In a separate control aimed at investigating the selectivity of the system, the sensor was incubated with 5 mM of cytidine, uridine or guanosine. As seen in line c) of FIG. 6, a significant change in contrast was not observed in any of these three cases.

Figure 7:
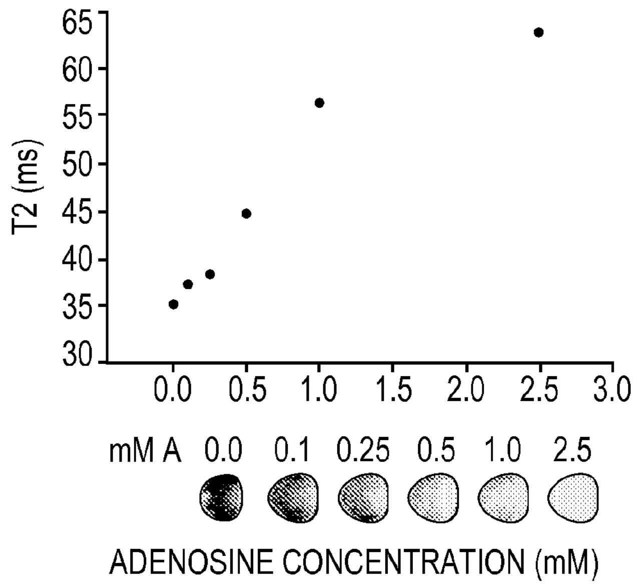
FIG. 7 illustrates the changes in T2 relaxation time (spin relaxation time) of the aptamer system of FIG. 4 in the presence of different concentrations of adenosine.
Figure 8:
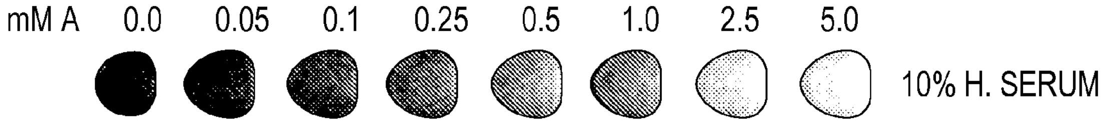
FIG. 8 illustrates the MRI brightness of the aptamer system of FIG. 4 in the presence of 10% human serum and different concentrations of adenosine.

Quantitative analysis was performed by measuring the T2 relaxation times of samples with varying adenosine concentration. A clear increase in T2 values was observed from 36 to 63 ms as the adenosine concentration increased from 0 to 2.5 Mm, as illustrated in FIG. 7. To demonstrate utility and stability of the current system in vivo, the sensor was prepared in the presence of 10% human serum. The activity of the sensor is retained in the presence of serum. Upon addition of adenosine the contrast within the concentration gradient increases (FIG. 8).

Experimental Section of Example 1

Materials: All DNA samples were purchased from Integrated DNA Technologies Inc. (Coralville, Iowa). The linker DNA molecules were purified by HPLC, whereas the thiol-modified DNA molecules were purified by the standard desalting method. Adenosine, cytidine, uridine and guanosine were purchased from Aldrich (St. Louis, Mo.). Cross-linked dextran coated superparamagnetic iron oxide nanoparticles (CLIO, 500 μg Fe ml-1) were synthesized and coupled to N-Succinimidyl 3-(2-pyridyldithio)-propionate (SPDP) according to literature procedure and purified with PD-10 column. [41] Thiol modified DNA (3'Adap and 5'Adap) was activated by incubating with eight equivalent of tris(2-carboxyethyl) phosphine hydrochloride (TCEP). Excess TCEP was removed by desalting using a SepPak C-18 cartridge. TCEP-activated thiol modified DNA (50 uM final concentration) was mixed with CLIO-SPDP (400 μg Fe ml-1) in 100 mM phosphate buffer pH 8.0 overnight. Excess DNA was removed by magnetic separation column (Miltenyi Biotec, Auburn, Calif.) from CLIO-DNA conjugates.

Aggregation of CLIO-DNA: 2 μl of 1 mM linker-Adap is added into 200 μl equimolar mixture of 3'Adap-CLIO and 5'Adap-CLIO (100 μg Fe ml-1) in 200 mM NaCl and 100 mM phospate buffer at pH 7.4. The solution was heated to 65° C. and cooled slowly to room temperature. The precipitation occurred within an hour. A non-complementary DNA was used as the linker for the control experiment.

Sensor preparation and MRI detection: 12 μl of 100 μM linker-Adap was added into 4 ml of 3'Adap-CLIO and 5'Adap-CLIO (20 μg Fe ml-1) in 300 mM NaCl and 25 mM tris-acetate buffer at pH 8.0. The solution was heated to 65° C. and cooled to room temperature overnight. 250 μl of sample was aliquoted into the wells of a microplate and varying amounts of adenosine was added in each well. The samples with serum were prepared by adding 10% human serum. Volume change was compensated by addition of distilled water.

T2 weighted MR images were obtained on a 4.7 T NMR instrument using a spin echo pulse sequence with variable echo time (TE=50–100 ms) and repetition time (TR) of 3000 ms. Relaxation times were measured on the same instrument with the Carr-Purcell-Meiboom-Gill (CPMG) pulse sequence.

Example 2

Thrombin is a serine protease which plays a key role in procoagulant and anticoagulant functions. To demonstrate the aptamer functionalized CLIO nanoparticles for an analyte detection thrombin was chosen to be detected via MRI with the use of aptamers where we combined the CLIO nanoparticles with thrombin aptamers, Thrm-A which binds to the fibrinogen-recognition exosite of thrombin and Thrm-B which binds to the heparin-binding exosite of thrombin, as shown in FIG. 9 [69, 70]. The contrast agent designed for thrombin detection was composed of 1:1 mixture of Thrm-A and Thrm-B functionalized CLIO nanoparticles (CLIO-Thrm-A and CLIO-Thrm-B, respectively) in aqueous solution. In the presence of thrombin, aptamer sequences fold into G-quadruplex arrangement in order to bind to thrombin [70-72]. After attachment of the CLIO nanoparticles to thrombin molecule the disperse nanoparticles assembled into aggregates changing the magnetic relaxation properties of nearby water protons, reducing the T2 relaxation time. This event could be monitored as a decrease in brightness of T2-weighted MRI image of the solution via MRI.

Figure 10:
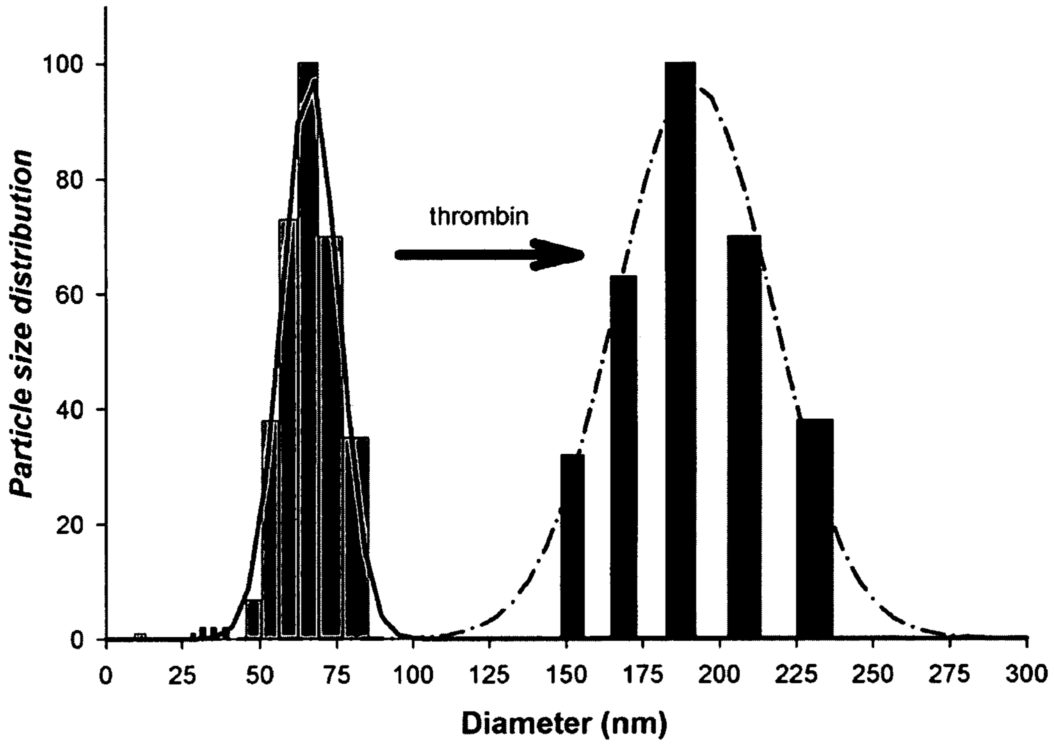
FIG. 10 illustrates the intensity weighted particle size distribution of CLIO nanoparticles with dynamic light scattering (DLS).
Figure 11:
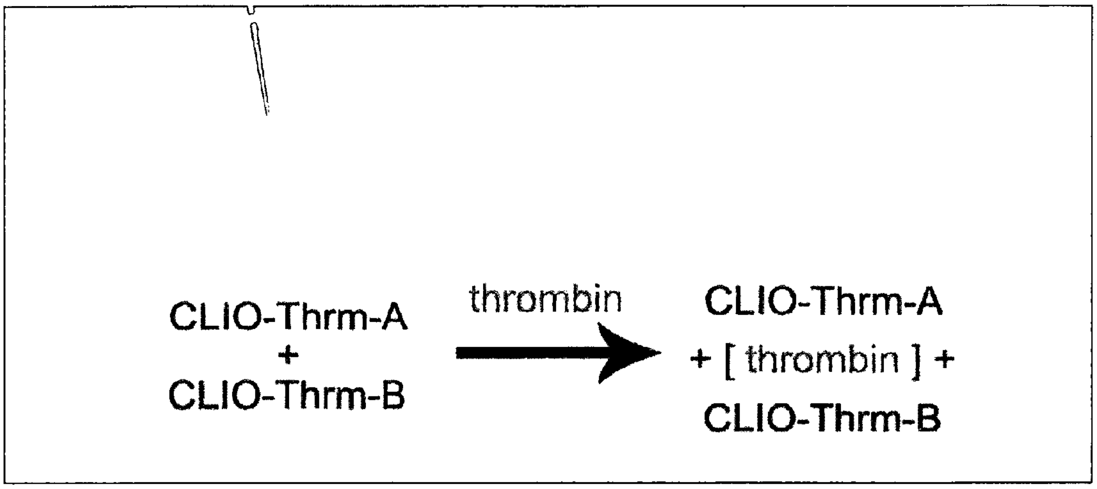
FIG. 11 illustrates the aggregation of the functionalized particles of the system of FIG. 9 in the presence of thrombin.

To confirm that the aptamers functionalized nanoparticles bind to thrombin molecules, 1 μM thrombin was added into the 1:1 homogenous mixture of CLIO-Thrm-A and CLIO-Thrm-B (150 μg Fe $ml^{-1}$), which resulted in rapid precipitation in seconds (FIG. 11). Similar behavior was not observed when BSA or streptavidin used as an effector. This result indicates that the precipitation of nanoparticles is due to the binding event of an effector and its aptamer. The particle size analysis also showed that upon addition of 50 nM thrombin into mixture of CLIO-Thrm-A and CLIO-Thrm-B (12 μg Fe $ml^{-1}$), the average diameter of CLIO nanoparticles immediately increased from 66.1±9.1 nm to 190.1±24.8. FIG. 10 shows the intensity weighted particle size distribution of CLIO nanoparticles with dynamic light scattering (DLS) which indicates that the nanoparticles were cross-linked by thrombin molecules therefore increasing the average diameter. At this CLIO nanoparticle concentration no precipitation of nanoparticles was observed. These results strongly suggest that the thrombin binding to aptamers on CLIO nanoparticles induces the assembly of nanoparticles.

Figure 12:
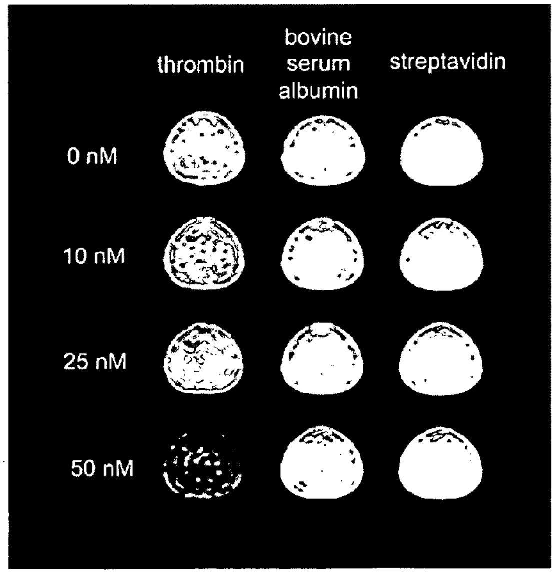
FIG. 12 illustrates the MRI brightness of the system of FIG. 9 in the presence of thrombin and controls.

This assembly decreased the T2 relaxation time of the neighboring water protons in the medium. Different thrombin concentrations from 0 to 50 nM were tested. A decrease in brightness of the MRI image of the samples was observed as the concentration of thrombin increased (FIG. 12) which was attributed to decrease in T2 relaxation time. A noticeable change in contrast was observed at as low as 10 nM thrombin and a significant change was observed at 50 nM thrombin.

Figure 13:
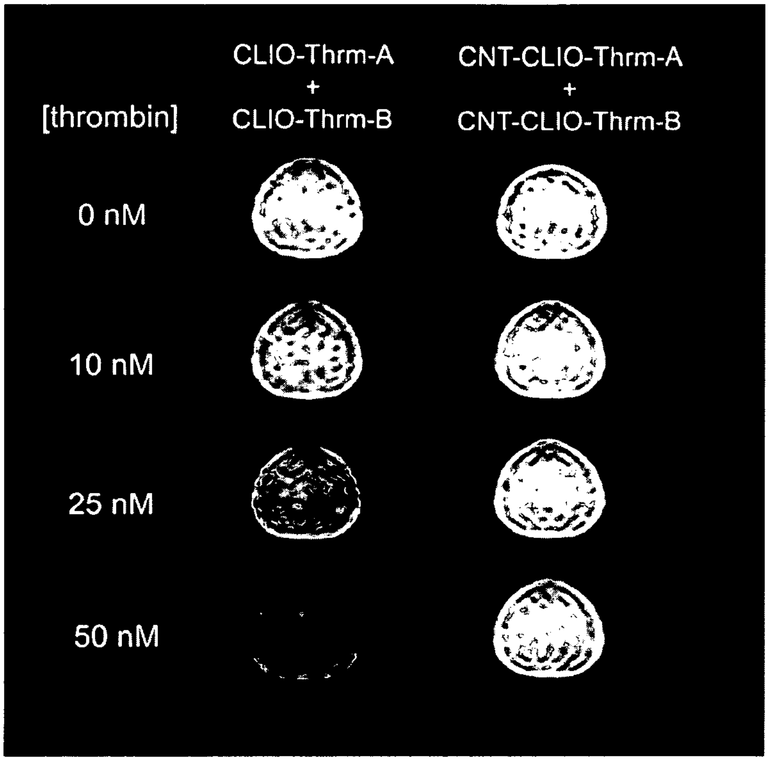
FIG. 13 illustrates the MRI brightness of the system of FIG. 9 and of a control system with particles that do not bind to thrombin.

To ensure that the contrast is solely due to binding event but not any other artifact the system was tested with bovine serum albumin (BSA) and streptavadin. The MRI images obtained with these two analytes showed no difference in contrast as their concentrations increased from 0 to 50 nM. This result suggests that the change in contrast is due to thrombin but not any other effect. In order to check if the change in contrast is due to aptamer and effector binding but not the thrombin molecule itself, inactive variants of the thrombin aptamer that had random DNA sequences and were different in length, were also tested. To do so a 1:1 mixture of inactive DNA aptamers (CNT-Thrm-A and CNT-Thrm-B) functionalized CLIO nanoparticles (CNT-CLIO-Thrm-A and CNT-CLIO-Thrm-B) was prepared. The prepared samples were subjected to same procedure in preparing the CLIO-Thrm-A and CLIO-Thrm-B and then placed into wells of a microplate. Thrombin was added into both systems with an increasing concentration from 0 to 50 nM. The obtained MR images showed that there was change in brightness of the MRI images of samples with CLIO-Thrm-A and CLIO-Thrm-B but no change with CNT-CLIO-Thrm-A and CNT-CLIO-Thrm-B (FIG. 13).

This result strongly suggests that the change in the MRI signal is due to the active aptamers but not any other non-specific interaction of DNA with thrombin. These two control experiments together strongly indicate that the change in MRI signal is solely due to the binding event of thrombin to the aptamers which then results in assembling CLIO nanoparticles into clusters decreasing the T2 relaxation time of the environment. The system demonstrated here is a strong potent aptamer-CLIO nanoparticle conjugate design for in vivo applications since (1) the CLIO nanoparticles are directly functionalized with aptamers, (2) the binding event is rapid, happening in seconds, (3) The required amount of CLIO nanoparticle for detection is as low as 12 μg Fe ml-1 (4) The MRI signal is due to binding of the aptamers to the target but not disassembly of the clustered CLIO nanoparticles into disperse ones, (5) The average diameter of CLIO nanoparticles is small enough to penetrate into tissue cells which can then carry on and bind to the target tissue, and last but not the least, (6) CLIO nanoparticles and DNA molecules are biocompatible and biodegradable in vivo. The system can be used for real target tissues for in vivo applications such as, prostate-membrane specific antigen (PMSA), which is an enzyme made on the surface of prostate cancer cells, can be targeted by PMSA functionalized CLIO nanoparticles and can be imaged by MRI.

Example 3

Screening of Inhibitors of Adenosine Deaminase (ADA)

ADA is an enzyme converting adenosine into inosine molecule. The screening of ADA inhibitors can be monitored with an aptamer system whereby an MRI signal is generated when a molecule inhibits the ADA.

For example, an aggregate of paramagnetic particles can be used to monitor the screening. To this end, a mixture including paramagnetic particles that are attached to oligonucleotides is prepared. A bridge including an aptamer that binds adenosine is also present in the mixture. If the tested molecule is not effective in inhibiting ADA, adenosine is transformed into inosine, and the complementary portions of the oligonucleotides are hybridized to the bridge. Aggregation of the particles into an aggregate follows, and an increase in MRI contrast is not observed.

Figure 18:
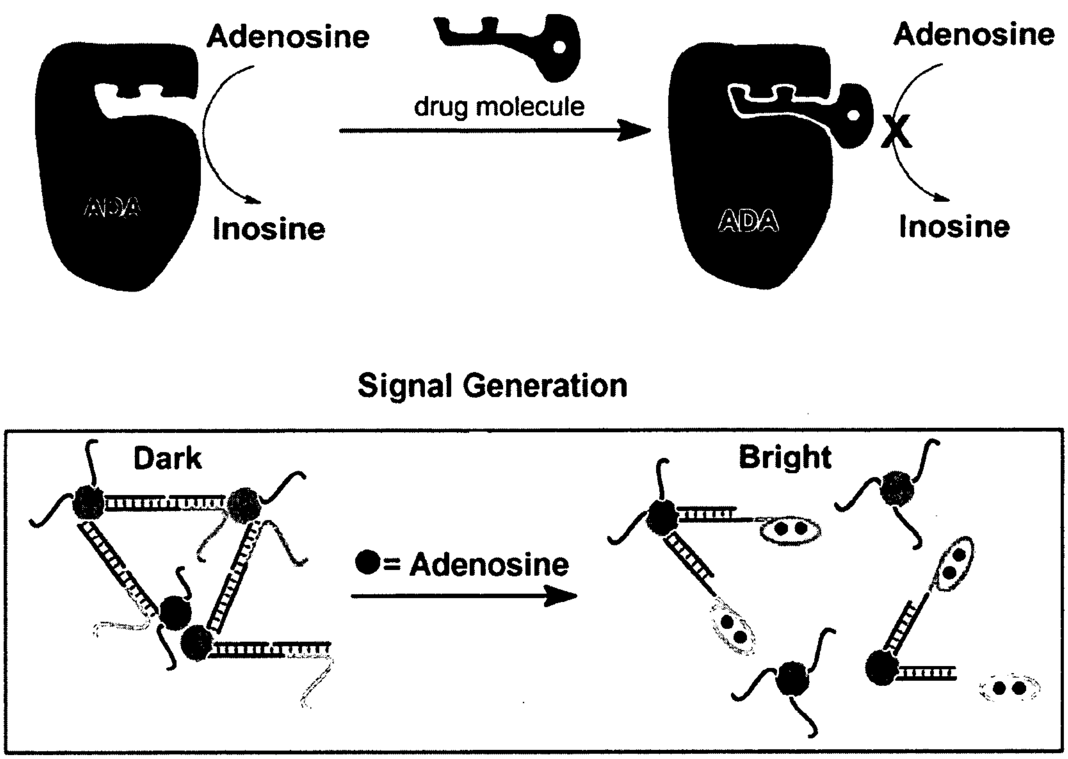
FIG. 18 illustrates the screening of ADA inhibitors with an aptamer system.

If the molecule is effective as inhibitor of ADA, then adenosine remains present, and its binding to the aptamer leads to structure switching of the aptamer. The resulting dehybridization leads to deaggregation of the aggregate, generating an MRI signal (FIG. 18).

Figure 19:
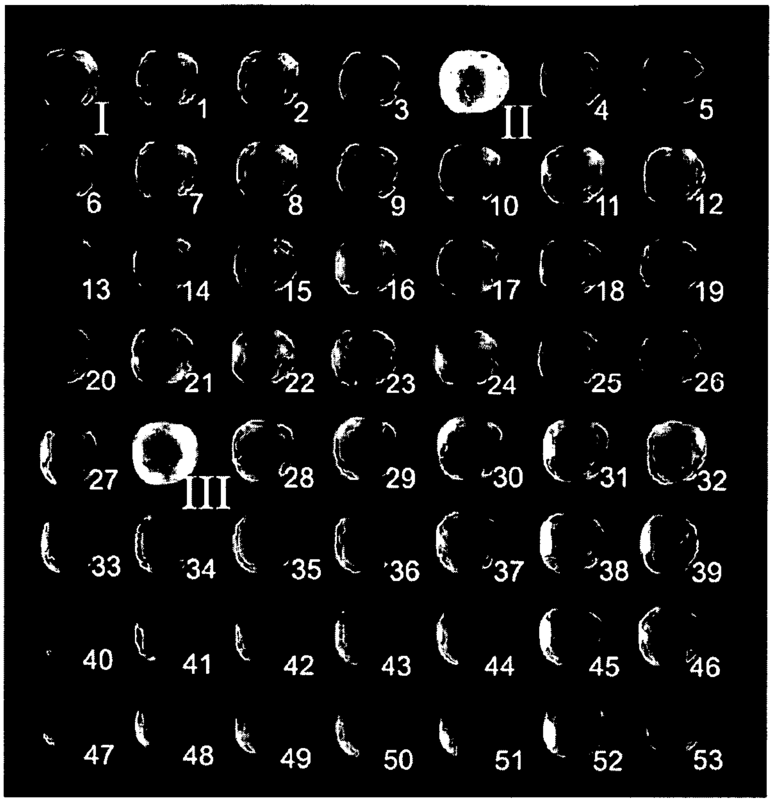
FIG. 19 illustrates the MRI brightness of an aptamer system according to FIG. 18 in the presence of adenosine and controls, in a tris-acetate buffer.
Figure 20:
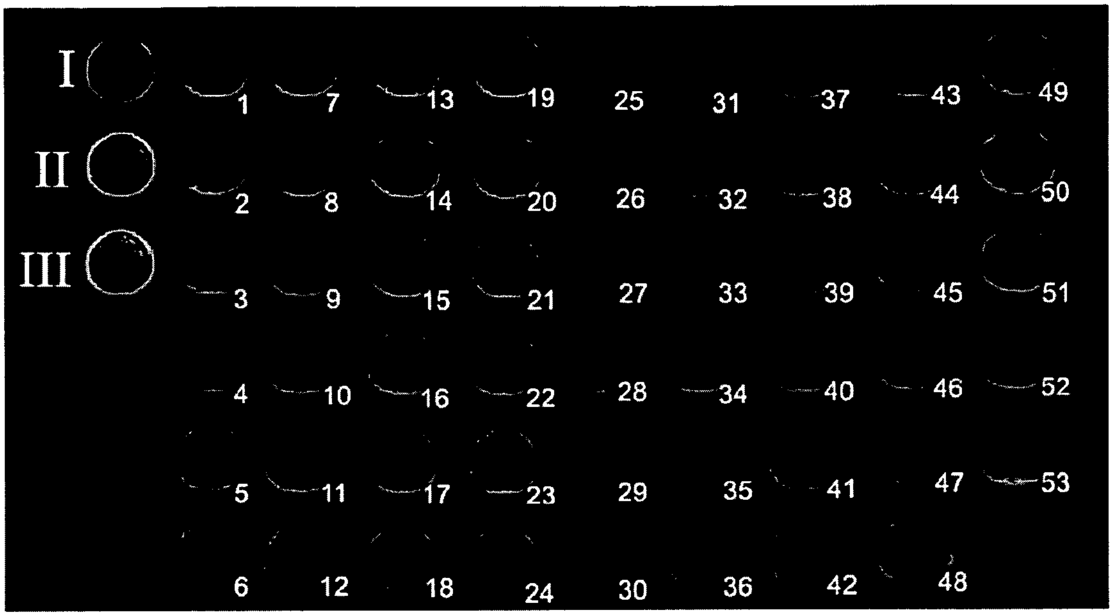
FIG. 20 illustrates the MRI brightness of an aptamer system according to FIG. 18 in the presence of adenosine and controls, in a human serum buffer.

FIGS. 19 and 20 feature MRI images of the screening of 50 molecules as ADA inhibitors. The screening was monitored by incubating with aggregates that included CLIO nanoparticles attached to polynucleotides and a bridge comprising an ADA-binding aptamer. The screening of FIG. 19 was carried out in the presence of tris-acetate buffer at pH 8.0. The screening of FIG. 20 was performed in human serum.

Sample I included ADA and adenosine but none of the screened molecules. Sample II included adenosine but no ADA, thereby resulting in an increase in MRI brightness when the aggregates were added.

Sample III included ADA, erythro-9-(2-hydroxy-3-nonyl) adenine hydrochloride (EHNA), a known ADA inhibitor, and adenosine. As expected, the EHNA of sample III inhibited the conversion of adenosine into inosine, and the aggregates underwent deaggregation, resulting in a bright MRI image. By contrast, control molecules 1 to 49, listed in Table 2, none of which was known to inhibit ADA, did not induce deaggregation or an increase in MRI signal.

TABLE 2

| | Compounds tested as ADA inhibitors |
|---|---|
| 1 | Nitrilotriacetic acid |
| 2 | PIPES |
| 3 | Boric acid |
| 4 | MES-Na Salt |
| 5 | Vanillin |
| 6 | Thiourea |
| 7 | Formic acid |
| 8 | 2,4,6 Trihydroxyacetophenone monohydrate |
| 9 | Sucrose |
| 10 | TRIS |
| 11 | L-leucine |
| 12 | N-Lauroyl sarcosine |
| 13 | Deoxycholic acid |
| 14 | Taurocholic acid |
| 15 | L-tyrosine |
| 16 | L-histidine |
| 17 | L-lysine dihydrochloride |
| 18 | L-valine |
| 19 | L-tryptophan |
| 20 | L-glutamine |
| 21 | L-arginine |
| 22 | L-Aspartic acid |
| 23 | L-methionine |
| 24 | L-serine |
| 25 | L-cysteine |
| 26 | L-Asparagine |
| 27 | L-isoleucine |
| 28 | D-xylose |
| 29 | (−)-Ephedrine hydrochloride |
| 30 | Citric acid |
| 31 | meso-2,3-dimercaptosuccinic acid |
| 32 | Thiosemicarbazide |
| 33 | Tetrabutylammonium fluoride hydrate |
| 34 | Uracil |
| 35 | Imidazole |
| 36 | 2,4-Dihydroxylbenzaldehyde |
| 37 | Cytidine |
| 38 | Ethylene diamine dihydrochloride |
| 39 | Ethylene diamine tetraacetic acid |
| 40 | Dextose |
| 41 | Propyl gallate |
| 42 | L-arginineamide |
| 43 | Inosine |
| 44 | d-Biotin |
| 45 | HEPES |
| 46 | Phenol |
| 47 | 5-amino-1-pentanol |
| 48 | Cystamine dihydrochloride |
| 49 | (−)-Riboflavin |
| 50 | BLANK |
| 51 | BLANK |
| 52 | BLANK |
| 53 | BLANK |

Experimental

DNA samples were purchased from Integrated DNA Technologies Inc. (Coralville, Iowa). The linker DNA was purified by HPLC and the thiol-modified DNA molecules were purified by the standard desalting method. Adenosine, EHNA and ADA were purchased from Sigma-Aldrich (St. Louis, Mo.). Cross-linked, dextran coated superparamagnetic iron oxide nanoparticles (CLIO, 500 μg Fe $ml^{-1}$) were prepared and coupled to N-Succinimidyl 3-(2-pyridyldithio)-propionate (SPDP) and purified with a PD-10 column (Amersham; Piscataway, N.J.). The thiol modified oligos, 3' Adap (5'TCACAGATGAGT-A12-SH 3'(SEQ ID NO: 1)) and 5' Adap (5'SH-CCCAGGTTCTCT 3'(SEQ ID NO: 2)) were incubated with eight equivalents of tris(2-carboxyethyl) phosphine hydrochloride (TCEP) in order to reduce the disulfide bond on thiol modifications. Excess TCEP was removed by desalting using a Sep-Pak C-18 catridge (Waters; Milford, Mass.). TCEP-activated thiol modified DNA (50 μM final concentration) was mixed with CLIO-SPDP (400 μg Fe $ml^{-1}$) in 100 mM phosphate buffer at pH 8.0 overnight. Excess DNA was removed by magnetic separation column (Miltenyi Biotec; Auburn, Calif.) from the CLIO-DNA conjugates.

Aptamer-functionalized CLIO nanoparticle aggregates were prepared by adding 27 μl of 100 μM linker-Adap to 8 ml of 3' Adap-CLIO and 5'Adap-CLIO (10 μg Fe $ml^{-1}$) in 300 mM NaCl and 25 mM tris-acetate buffer at pH 8.0. The resulting solution was heated to 65° C. and cooled to room temperature overnight.

The ADA solution was prepared by diluting 75 μl of an ADA stock solution in 6 ml of 300 mM NaCl and 25 mM tris-acetate buffer at pH 8.0, obtaining a final ADA concentration of 500 nM. The molecules to be tested were dissolved in water to a 5 mM final concentration. 50 μl of ADA solution were placed into the wells of a microplate and 4 μl of the solution of a molecule were added to the ADA solution and left to incubate for 30 minutes. 20 μl of 50 mM adenosine were then added to each well and the resulting solutions were incubated for 90 minutes. 150 μl of nanoparticle suspension were then added to each well. After incubating for 60 minutes, MRI images were taken. The samples in serum were prepared by adding 20 μl human serum to 50 μl of the ADA solution before aliquoting into the wells of microplate, and then incubating with the molecules. Volume differences in samples with no ADA were compensated by the addition of 300 mM NaCl and 25 mM tris-acetate buffer.

T2-weighted MRI images were obtained on a 4.7 T NMR instrument using a spin echo pulse sequence with variable echo time (TE=20–100 ms) and a repetition time (TR) of 2000 ms. Relaxation times were measured on the same instrument with the Carr-Purcell-Meiboom-Gill (CPMG) pulse sequence.

References

[1] A. D. Ellington, J. W. Szostak, Nature 1990, 346, 818.

[2] C. Tuerk, L. Gold, Science 1990, 249, 505.

[3] D. S. Wilson, J. W. Szostak, Annu. Rev. Biochem. 1999, 68, 611.

[4] M. Famulok, G. Mayer, M. Blind, Acc. Chem. Res. 2000, 33, 591.

[5] D. W. Drolet, L. Moon-McDermott, T. S. Romig, Nat. Biotechnol. 1996, 14, 1021.

[6] Y. Wang, J. Killian, K. Hamasaki, R. R. Rando, Biochemistry 1996, 35, 12338.

[7] S. D. Jayasena, Clin. Chem. 1999, 45, 1628.

[8] M. Liss, B. Petersen, H. Wolf, E. Prohaska, Anal. Chem. 2002, 74, 4488.

[9] R. Yamamoto, T. Baba, P. K. Kumar, Genes Cells 2000, 5, 389.

[10] S. D. Jhaveri, R. Kirby, R. Conrad, E. J. Maglott, M. Bowser, R. T. Kennedy, G. Glick, A. D. Ellington, J. Am. Chem. Soc. 2000, 122, 2469.

[11] M. N. Stojanovic, P. de Prada, D. W. Landry, J. Am. Chem. Soc. 2000, 122, 11547.

[12] J. Li, Y. Lu, J. Am. Chem. Soc. 2000, 122, 10466.

[13] N. Hamaguchi, A. Ellington, M. Stanton, Anal. Biochem. 2001, 294, 126.

[14] X. Fang, Z. Cao, T. Beck, W. Tan, Anal. Chem. 2001, 73, 5752.

[15] M. N. Stojanovic, P. P. de, D. W. Landry, J Am Chem Soc 2001, 123, 4928.

[16] J. J. Li, X. Fang, W. Tan, Biochem. Biophys. Res. Commun. 2002, 292, 31.

[17] R. Nutiu, Y. Li, J. Am. Chem. Soc. 2003, 125, 4771.

[18] R. Nutiu, Y. Li, Chem. Eur. J. 2004, 10, 1868.

[19] Y. Chen, M. Wang, C. Mao, Angew. Chem. Int. Ed. 2004, 43, 3554.

[20] Y. Liu, C. Lin, H. Li, H. Yan, Angew. Chem. Int. Ed. 2005, 44, 4333.

[21] Y. Tian, C. Mao, Talanta 2005, 67, 532.

[22] N. K. Navani, Y. Li, Curr. Opin. Chem. Biol. 2006, 10, 272.

[23] M. N. Stojanovic, D. W. Landry, J. Am. Chem. Soc. 2002, 124, 9678.

[24] J. Liu, Y. Lu, J. Am. Chem. Soc. 2003, 125, 6642.

[25] V. Pavlov, Y. Xiao, B. Shlyahovsky, I. Willner, J. Am. Chem. Soc. 2004, 126, 11768.

[26] J. Liu, Y. Lu, Anal. Chem. 2004, 76, 1627.

[27] H.-A. Ho, M. Leclerc, J. Am. Chem. Soc. 2004, 126, 1384.

[28] C.-C. Huang, Y.-F. Huang, Z. Cao, W. Tan, H.-T. Chang, Anal. Chem. 2005, 77, 5735.

[29] J. Liu, Y. Lu, Angew. Chem. Int. Ed. 2006, 45, 90.

[30] D. Xu, D. Xu, X. Yu, Z. Liu, W. He, Z. Ma, Anal. Chem. 2005, 77, 5107.

[31] Y. Xiao, B. D. Piorek, K. W. Plaxco, A. J. Heeger, J. Am. Chem. Soc. 2005, 127, 17990.

[32] Y. Xiao, A. A. Lubin, A. J. Heeger, K. W. Plaxco, Angew. Chem. Int. Ed. 2005, 44, 5456.

[33] A.-E. Radi, J. L. Acero Sanchez, E. Baldrich, C. K. O'Sullivan, J. Am. Chem. Soc. 2006, 128, 117.

[34] M. J. Allen, T. J. Meade, Met. Ions Biol. Syst. 2004, 42, 1.

[35] D. E. Sosnovik, R. Weissleder, Curr. Opin. Biotechnol. 2007, 18, 4.

[36] L. Josephson, J. Lewis, P. Jacobs, P. F. Hahn, D. D. Stark, Magn. Reson. Imaging 1988, 6, 647.

[37] T. Shen, R. Weissleder, M. Papisov, A. Bogdanov, Jr, T. J. Brady, Magn. Reson. Med. 1993, 29, 599.

[38] L. Josephson, J. M. Perez, R. Weissleder, Angew. Chem. Int. Ed. 2001, 40, 3204.

[39] C. H. Lin, D. J. Patel, Chem. Biol. 1997, 4, 817.

[40] T. Hermann, D. J. Patel, Science (Washington, D.C.) 2000, 287, 820.

[41] L. Josephson, C.-H. Tung, A. Moore, R. Weissleder, Bioconjugate Chem. 1999, 10, 186.

[42] K. B. Chapman, J. W. Szostak, Curr. Opin. Struct. Biol. 1994, 4, 618.

[43] G. F. Joyce, Curr. Opin. Struct. Biol. 1994, 4, 331.

[44] C. Tuerk, L. Gold L, Science 1990, 249, 505.

[45] R. C. Cadwell, G. F. Joyce, PCR Methods Appl. 1992, 2, 28.

[46] R. C. Cadwell, G. F. Joyce G F, PCR Methods Appl. 1994, 33, 136.

[47] J. Tsang, G. F. Joyce, In vitro evolution of randomized ribozymes. Methods Enzymol. 1996, 267, 410.

[48] J. Conaty, P. Hendry, T. Lockett, Nucleic Acids Res. 1999, 27, 2400.

[49] M. Zillmann, S. E. Limauro, J. Goodchild, RNA 1997, 3, 734.

[50] Y. Lu and J. Li, U.S. Pat. No. 6,706,474.

[51] Whitesides, Proceedings of the Robert A. Welch Foundation 39th Conference On Chemical Research Nanophase Chemistry, 1995, Houston, Tex.

[52] R. Mucic, M. Herrlein, C. A. Mirkin, R. Letsinger, Chem. Commun. 1996, 555.

[53] T. Beebe, C. Rabke-Clemmer, U.S. Pat. No. 5,472, 881.

[54] K. Grabar, R. Freeman, M. Hommer, M. Natan, 1995, 67, 735.

[55] W. L. Shaiu, D. D. Larson, J. Vesenka, E. Henderson, Nucleic Acids Res. 1993, 21, 99.

[56] D. Allara, R. Nuzzo, Langmuir 1985, 1, 45.

[57] R. Nuzzo, F. Fusco, D. Allara, J. Am. Chem. Soc. 1987, 109, 2358.

[58] Iler R., 1979 Chapter 6. In: anonymous (eds) The chemistry of silica. Wiley, New York.

[59] H. Tompkins, D. Allara, J. Colloid and Interface Sci., 1974, 49410.

[60] Timmons, Zisman, J. Phys. Chem. 1965, 69, 984.

[61] M. Soriaga, A. Hubbard, J. Am. Chem. Soc., 1982, 104.

[62] R. Maoz, J. Sagiv, Langmuir, 1987, 3, 1034.

[63] Y. Lu, J. Liu, U.S. Publ. Pat. No. 2004/0175693.

[64] M. Zhao, L. Josephson, Y. Tang, R. Weissleder, Angew. Chem. Int. Ed. 2003, 42, 1375.

[65] L. Josephson, J. M. Perez, R. Weissleder, Angew. Chem. Int. Ed. 2001, 40, 3204.

[66] E. Taboada et al., Langmuir 2007, 23, 4583.

[67] S. Wang et al., J. Am. Chem. Soc. 2007, 129, 3848.

[68] P. S. Pendergrast et al., J. of Biomol. Techn., 2005, 16, 224.

[69] L. C. Bock et al., Nature 1992, 355, 564.

[70] D. M. Tasset et al., Mol. Biol. 1997, 272, 688.

[71] R. F. Macaya et al., Proc. Natl. Acad. Sci. U.S.A. 1993, 90, 3745.

[72] K. Padmanabhan, J. Biol. Chem. 1993, 268, 17651.

[73] D. H. Carr et al., AJR Amer. J. Roentgenol. 1984, 143, 215.

[74] G. Kabalka et al., Radiology 1987, 163, 255.

[75] R. Weissleder et al., AJR Amer. J. Roentgenol. 1987, 149, 723.

[76] L. Josephson et al., Magn. Reson. Imaging 1988, 6, 647.

[77] M. Saeed et al., Radiology 1989, 172, 59.

[78] W. Li, J. Am. Chem. Soc. 1999, 121, 1413.

[79] M. G. Harisinghani et al., New. England. J. Med. 2003, 348, 2491.

[80] J. Lee et al., J. Am. Chem. Soc. 2005, 127, 13164.

[81] L. Frullano et al., Inorg. Chem. 2006, 45, 8489.

[82] M. Kresse et al., Magn. Reson. Med. 1998, 40, 236.

[83] W. S. Enochs et al., J. Magn. Reson. Imaging 1999, 9, 228.

[84] C. H. Dodd et al., J. Immunol. Methods 2001, 256, 89.

[85] M. E. Kooi et al., Circulation 2003, 107, 2453.

[86] D. Artemov et al., Magn. Reson. Med. 2003, 49, 403.

[87] C. Corot et al., Invest. Radiol. 2004, 39, 619.

[88] N. Nitin et al., J. Biol. Inorg. Chem. 2004, 9, 706.

[89] L. Josephson et al., Bioconjugate Chem. 1999, 10, 186.

[90] M. Lewin et al., Nat. Biotechnol. 2000, 18, 410.

[91] L. Josephson et al., Angew. Chem. Int. Ed. 2001, 40, 3204.

[92] J. M. Perez et al., Chem Bio Chem 2004, 5, 261.

[93] M. Zhao et al., Bioconjugate Chem. 2002, 13, 840.

[94] M. Zhao et al., Angew. Chem. Int. Ed. 2003, 42, 1375.

[95] J. M. Perez et al, J. Am. Chem. Soc. 2003, 125, 10192.

[96] A. Tsourkas et al., Angew. Chem. Int. Ed. 2004, 43, 2395.

[97] R. Nutiu et al., Pure Appl. Chem. 2004, 76, 1547.

[98] F. Hoppe-Seyler et al., Curr. Mol. Med. 2004, 4, 529.

[99] K. Nagel-Wolfrum et al., Mol. Cancer. Res. 2004, 2, 170.

[100] C. Buerger et al., J. Cancer Clin. Oncol., 2003, 129 (12), 669.

[101] C. Buerger et al., J. Biol. Chem. 2003, 278(39), 37610.

[102] PCT Pat. Publ. No. WO2005/100602.

[103] U.S. Publ. Pat. No. 20030215810.

[104] U.S. Publ. Pat. No. 20060166222.

[105] U.S. Publ. Pat. No. 20070037171.

What is claimed is:

1. An MRI contrast agent, comprising:

(i) MRI contrast agent particles that are biocompatible and biodegradable in vivo, (ii) oligonucleotides, attached to the particles, wherein the oligonucleotides have one end attached to the particles and a second free end; and (iii) an aptamer comprising an oligonucleotide sequence that is complementary to the free end of two oligonucleotides attached to different particles, wherein the aptamer is hybridized to the free end of the two oligonucleotides thereby forming a bridge between the particles, wherein the particles, the oligonucleotides, and the aptamer, together form aggregates in absence of the effector and wherein the aptamer, specific for an effector, undergoes a conformational change when bound to the effector, causing the particles to disaggregate.

2. The MRI contrast agent of claim 1, wherein the MRI contrast agent particles comprise gadolinium, manganese, iron, superparamagnetic iron oxide (SPIO), oral SPIO, ultrasmall superparamagnetic iron oxide (USPIO), paramagnetic fullerene pipes, fullerene nanoparticles, nanotubes, gadonanotubes, quantum dots coated or doped with a paramagnetic material, paramagnetic liposomes, a paramagnetic material or perfluorocarbon particles.

3. The MRI contrast agent of claim 1, wherein the effector is adenosine or a metal ion.

4. An MRI contrast agent, comprising:

MRI contrast agent particles that are biocompatible and biodegradable in vivo;

oligonucleotides, attached to the particles, wherein the oligonucleotides have one end attached to the particles and a second free end; and a nucleic acid enzyme specific for an effector, comprising (a) an oligonucleotide substrate strand comprising an oligonucleotide sequence that is complementary to the free end of two oligonucleotides attached to different particles, wherein the oligonucleotide substrate strand is hybridized to the free end of the two oligonucleotides thereby forming a bridge between the particles, and (b) an oligonucleotide enzyme strand which is hybridized to the oligonucleotide substrate strand, wherein the particles, the oligonucleotides, the oligonucleotide substrate strand and the oligonucleotide enzyme strand, together form aggregates in absence of the effector; and wherein the oligonucleotide enzyme strand cleaves the oligonucleotide substrate strand in the presence of the effector, causing the particles to disaggregate.

5. The MRI contrast agent of claim 4, wherein the oligonucleotide substrate strand comprises:

first and second portions, hybridized to the free end of the two oligonucleotides attached to the different particles, and wherein the first and second portions are cleaved by the oligonucleotide enzyme strand in the presence of the effector.

6. A method of forming an MRI image of a sample, comprising:

mixing the sample with the MRI contrast agent of claim 1; and imaging the sample by MRI.

7. An MRI sensor system for screening a molecule against a test enzyme, comprising:

the MRI contrast agent of claim 1, and a test enzyme, wherein the test enzyme reacts with a corresponding substrate to form a product, and wherein the substrate binds to the aptamer but the product does not or wherein the substrate does not bind to the aptamer but the product does.

8. An MRI sensor system for screening a molecule against a test enzyme, comprising:

the MRI contrast agent of claim 4, and a test enzyme that catalyzes conversion to the effector, wherein the bridge is cleaved in the presence of the effector.

9. An MRI sensor system for screening a molecule against a test enzyme, comprising:

the MRI contrast agent of claim 4, and a test enzyme that catalyzes conversion of a corresponding substrate to a product, wherein the corresponding substrate is the effector, wherein the bridge is cleaved in the presence of the corresponding substrate.

10. An MRI sensor system for screening a molecule against a test enzyme, comprising:

the MRI contrast agent of claim 5 an assay enzyme, and a test enzyme, wherein the first and second portions are ligated by the assay enzyme in the presence of an effector, the test enzyme reacts with a corresponding substrate to form a product, and the corresponding substrate or the product is the effector.

11. The MRI sensor system of claim 7, wherein the MRI contrast agent particles comprise a paramagnetic material.

12. The MRI sensor system of claim 7, wherein the MRI contrast agent particles comprise at least one member selected from the group consisting of gadolinium, manganese, iron, SPIO, oral SPIO, USPIO, paramagnetic fullerene pipes, fullerene nanoparticles, nanotubes, gadonanotubes, quantum dots coated or doped with a paramagnetic material, paramagnetic liposomes and perfluorocarbon particles.

13. The MRI sensor system of claim 8, wherein the MRI contrast agent particles comprise a paramagnetic material.

14. A method of producing an MRI image in vivo, comprising:

administering the MRI contrast agent of claim 1 to a subject; and imaging the subject by MRI.

15. A method of producing an MRI image in vivo, comprising:

administering the MRI contrast agent of claim 4 to a subject; and imaging the subject by MRI.

16. An MRI contrast agent, comprising:

MRI contrast agent particles that are biocompatible and biodegradable in vivo;

oligonucleotides, attached to the particles, wherein the oligonucleotides have one end attached to the particles and a second free end; and an aptazyme specific for an effector and a co-factor, comprising (a) an oligonucleotide substrate strand comprising an oligonucleotide sequence that is complementary to the free end of two oligonucleotides attached to different particles wherein the oligonucleotide substrate strand is hybridized to the free end of the two oligonucleotides thereby forming a bridge between the particles, and (b) an oligonucleotide enzyme strand hybridized to the oligonucleotide substrate strand, wherein the oligonucleotide enzyme strand comprises (i) an aptamer portion comprising a binding site for the effector, and (ii) an enzyme portion comprising a binding site for the co-factor when hybridized to the oligonucleotide substrate strand, wherein the particles, the oligonucleotides, the oligonucleotide substrate strand and the oligonucleotide enzyme strand, together form aggregates in absence of the effector and the co-factor; and wherein the oligonucleotide enzyme strand cleaves the oligonucleotide substrate strand in the presence of the effector and the co-factor, causing the particles to disaggregate.

17. A method of producing an MRI image in vivo, comprising:

administering the MRI contrast agent of claim 16 to a subject; and imaging the subject by MRI.

18. The MRI contrast agent of claim 1, wherein the effector is a cancer antigen, growth factor, nucleic acid binding protein, anthrax, small pox, a pollutant, cocaine, or human immuno-deficiency virus (HIV).

19. The MRI contrast agent of claim 4, wherein the effector is a cancer antigen, growth factor, nucleic acid binding protein, anthrax, small pox, a pollutant, cocaine, adenosine, a metal ion, or human immuno-deficiency virus (HIV).

20. The MRI contrast agent of claim 16, wherein the effector is a cancer antigen, growth factor, nucleic acid binding protein, anthrax, small pox, a pollutant, cocaine, adenosine, or human immuno-deficiency virus (HIV).

21. The MRI contrast agent of claim 1, wherein the effector is prostate specific membrane antigen (PSMA), tenasin-C, basic fibroplastic growth factor, platelet derived growth factor (PDGF), nuclear factor kB, transcription factor E2F, or gonadotropin-releasing hormone.

22. The MRI contrast agent of claim 4, wherein the effector is prostate specific membrane antigen (PSMA), tenasin-C, basic fibroplastic growth factor, platelet derived growth factor (PDGF), nuclear factor kB, transcription factor E2F, or gonadotropin-releasing hormone.

23. The MRI contrast agent of claim 16, wherein the effector is prostate specific membrane antigen (PSMA), tenasin-C, basic fibroplastic growth factor, platelet derived growth factor (PDGF), nuclear factor kB, transcription factor E2F, or gonadotropin-releasing hormone.

24. The MRI contrast agent of claim 4, wherein the MRI contrast agent particles comprise gadolinium, manganese, iron, superparamagnetic iron oxide (SPIO), oral SPIO, ultrasmall superparamagnetic iron oxide (USPIO), paramagnetic fullerene pipes, fullerene nanoparticles, nanotubes, gadonanotubes, quantum dots coated or doped with a paramagnetic material, paramagnetic liposomes, a paramagnetic material or perfluorocarbon particles.

25. The MRI contrast agent of claim 16, wherein the MRI contrast agent particles comprise gadolinium, manganese, iron, superparamagnetic iron oxide (SPIO), oral SPIO, ultrasmall superparamagnetic iron oxide (USPIO), paramagnetic fullerene pipes, fullerene nanoparticles, nanotubes, gadonanotubes, quantum dots coated or doped with a paramagnetic material, paramagnetic liposomes, a paramagnetic material or perfluorocarbon particles.

26. The MRI contrast agent of claim 1, wherein the MRI contrast agent particles comprise a paramagnetic material.

27. The MRI contrast agent of claim 4, wherein the MRI contrast agent particles comprise a paramagnetic material.

28. The MRI contrast agent of claim 16, wherein the MRI contrast agent particles comprise a paramagnetic material.

29. The MRI contrast agent of claim 1, wherein the effector is thrombin.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

tcacagatga gtaaaaaaaa aaaa                                            24


<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

cccaggttct ct                                                         12


<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

actcatctgt gaagagaacc tgggggagta ttgcggagga aggt                      44


<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

cccaggttct cttcacagat gagtaaaaaa aaaaaa                               36


<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

tttttttttt tttttggttg gtgtggttgg                                      30


<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 6

tttttagtcc gtggtagggc aggttggggt gact                          34
```